(12) United States Patent
Baynes et al.

(10) Patent No.: US 7,030,146 B2
(45) Date of Patent: Apr. 18, 2006

(54) METHODS FOR TREATING DIABETIC NEUROPATHY

(75) Inventors: John W. Baynes, Columbia, SC (US); Suzanne R. Thorpe, Columbia, SC (US); Thorsten P. Degenhardt, Durham, NC (US); Raja G. Khalifah, Overland Park, KS (US); Billy G. Hudson, Lenexa, KS (US); Nathan Alderson, West Columbia, SC (US)

(73) Assignees: University of South Carolina, Columbia, SC (US); Kansas University Medical Center, Kansas City, KS (US)

(*) Notice: Subject to any disclaimer, the term of this patent is extended or adjusted under 35 U.S.C. 154(b) by 20 days.

(21) Appl. No.: 10/355,442

(22) Filed: Jan. 30, 2003

(65) Prior Publication Data

US 2003/0181492 A1 Sep. 25, 2003

Related U.S. Application Data

(63) Continuation of application No. 09/422,615, filed on Oct. 21, 1999, now Pat. No. 6,740,668, and a continuation-in-part of application No. 08/971,285, filed on Nov. 17, 1997, now Pat. No. 6,228,858, and a continuation-in-part of application No. 08/711,555, filed on Sep. 10, 1996, now Pat. No. 5,985,857.

(60) Provisional application No. 60/105,182, filed on Oct. 22, 1998.

(51) Int. Cl.
*A61K 31/4415* (2006.01)

(52) U.S. Cl. .................................... 514/351; 514/345
(58) Field of Classification Search ............ 514/351, 514/345
See application file for complete search history.

(56) References Cited

U.S. PATENT DOCUMENTS

| 5,288,716 | A | 2/1994 | Speck | 514/89 |
|---|---|---|---|---|
| 5,985,857 | A | 11/1999 | Hudson et al. | 514/89 |
| 6,228,858 | B1 | 5/2001 | Hudson et al. | 514/247 |
| 6,436,969 | B1 | 8/2002 | Khalifah et al. | 514/345 |
| 6,472,400 | B1 | 10/2002 | Hudson et al. | 514/277 |
| 6,472,411 | B1 | 10/2002 | Hudson et al. | 514/345 |
| 6,521,645 | B1 | 2/2003 | Voziyan et al. | 514/351 |
| 6,746,678 | B1 * | 6/2004 | Shapiro | 424/400 |
| 6,750,209 | B1 * | 6/2004 | Hudson et al. | 514/89 |
| 2002/0128295 | A1 | 9/2002 | Baynes et al. | 514/349 |
| 2003/0013746 | A1 | 1/2003 | Hudson et al. | 514/345 |
| 2003/0017995 | A1 | 1/2003 | Khalifah et al. | 514/23 |

FOREIGN PATENT DOCUMENTS

| CA | 2 055 990 | 5/1992 |
|---|---|---|
| DE | 19 15 497 | 11/1970 |
| DE | 24 61 742 | 7/1976 |
| DE | 37 05 549 | 9/1988 |
| EP | 0 474 874 | 3/1992 |
| FR | 2 349 330 | 11/1997 |
| GB | 1 093 546 | 12/1967 |
| GB | 1 478 560 | 7/1977 |
| JP | 221473 | 8/1997 |
| JP | 158244 | 6/1998 |
| JP | 175954 | 6/1998 |
| WO | WO 92/02216 | 2/1992 |
| WO | WO 97/09981 | 3/1997 |
| WO | WO 99/25690 | 5/1999 |

OTHER PUBLICATIONS

Noma, et al., (1973), Clin. Chim. Acta, 43: pp. 317-320.
Bergman, et al., (1974), Assay of Glycerol-Phosphate Dehydrogenase. In Methods of Enzymatic Analysis, vol. 3. Bergman, H.V. Berlin: Verlag Chemie. pp. 1404-1408.
Li, et al., (1980), Clin. Chem, 26: pp. 1713-1717.
Weibel and Gomez, (1962), J. Appl. Physiol, 17: pp. 343-348.
Jensen, et al., (1979), J. Microscopy, 115: pp. 19-33.
Williamson, et al., (1993), Diabetes, 42: pp. 801-813.
Mayrovitz and Larsen, (1996), Microvasc. Res, 52: pp. 115-126.
Tesfaye, et al., (1994), Diabetologia, 37: pp. 847-854.
Ellis and Good, (1991), Metabolism, 40: pp. 1016-1019.
Oturai, et al., (1996), APMIS, 104: pp. 259-264.
Soulis-Liparota, et al., (1991), Diabetes, 40: pp. 1328-1334.
Yamauchi, et al., (1997), Diab. Res. Clin. Pract, 34: pp. 127-133.
Bucala, et al., (1994), Proc. Natl. Acad. Sci, 91: pp. 9441-9445.

(Continued)

*Primary Examiner*—Phyllis G. Spivack
(74) *Attorney, Agent, or Firm*—McDonnell Boehnen Hulbert & Berghoff LLP

(57) ABSTRACT

A method for treating diabetic neuropathy is disclosed consisting of administering pyridoxamine or a salt thereof.

2 Claims, 57 Drawing Sheets

OTHER PUBLICATIONS

Cameron and Cotter, (1994), Diav. Metab. Rev, 10: pp. 189-224.
Boulton and Malik, (1999), Organ Specific Vascular Changes. In Diabetic Angiopathy. Took, J.E., editor. New York: Oxford University Press. pp. 267-275.
Pyke, et al., (1999), Diabetes 48 (Suppl. 1) 593(Abstr.)).
Fu, et al., (1996), J. Biol. Chem, 271: pp. 9982-9986.
Litchfield, et al., (1999), Int. J. Biochem., 31: pp. 1297-1305.
Oda and Keane, (1997), Kidney Internat. 52, Suppl. 2: S36-S38.
Smulders, et al., (1997), Eur. J. Clin. Invest, 27: pp. 997-1002.
Guijarro and Keane, (1993), Curr. Opin. Nephrol. Hypertens, 2: pp. 372-379.
Saito, T., (1997), Tohoku J. Exp. Med, 181: pp. 321-337.
Picard, et al., (1992), Proc. Natl. Acad. Sci. USA, 89: pp. 6876-6880.
Giardino, et al., (1998), Diabetes, 47: pp. 1114-1120.
Andrus, et al., (1998), J. Neurochem, 71: pp. 2041-2048.
Hall, et al, (1998), J. Neurosci, Res, 53: pp. 66-77.
Smith, et al., (1998), J. Histochem. Cytochem, 46: pp. 731-735.
Smith, et al., (1998), J. Neurochem, 70: pp. 2212-2215.
Russell, et al, (1999), Arch. Biochem. Biophys, 370: pp. 236-239.
Flowers and Zimmerman, (1998), New Horizons, 6: pp. 169-180.
Piedimonte, et al., (1997), J. Infect. Disease, 176: pp. 655-664.
Colaco and Harrington, (1994), NeuroReport, 5: pp. 859-861.
Vlassara, Bucala & Striker, (1994), Lab. Invest, 70: pp. 138-151.
Vlassara, et al., (1994), PNAS (USA), 91: pp. 11704-11708.
Daniels & Hauser, (1992), Diabetes, 41: pp. 1415-1421.
Brownlee, (1994), Diabetes, 43: pp. 836-841.
Cohen, et al., (1994), Kidney Int, 45: pp. 1673-1679.
Brett, et al., (1993), Am. J. Path, 143: pp. 1699-1712.
Yan, et al., (1994), PNAS (USA), 91: pp. 7787-7791.
Harding, (1985), Adv. Protein Chem, 37: pp. 248-334.
Monnier & Baynes eds., (1989), The Maillard Reaction in Aging, Diabetes, and Nutrition (Alan R. Liss, New York). pp. 43-67.
Finot, et al., (1990), eds. The Maillard Reaction in Food Processing, Human Nutrition and Physiology (Birkhauser Verlag, Basel). pp. 259-272.
Means & Chang, (1982), Diabetes, 31, Suppl. 3: pp. 1-4.
Sell and Monnier, (1989), J. Biol. Chem, 264: pp. 21597-21602.
Ahmed, et al., (1986), J. Biol. Chem, 261: pp. 4889-4894.
Nakayama, et al., (1989), Biochem. Biophys. Res. Comm, 162: pp. 740-745.
Nakayama, et al., (1991), J. Immunol. Methods, 140: pp. 119-125.
Horiuchi, et al., (1991), J. Biol. Chem, 266: pp. 7329-7332.
Araki, et al., (1992), J. Biol. Chem, 267: pp. 10211-10214.
Makita, et al., (1992), J. Biol. Chem, 267: pp. 5133-5138.
(1990), The Pharmacological Basis of Therapeutics, 8th edition, ed. Gilman, Rall, Nies, and Taylor (Pergamon Pres, New York, pp. 1293-4; pp. 1523-1540.
Reddy, et al., (1995), Biochem, 34: pp. 10872-10878.
Engvall, (1981), Methods Enzymol, 70: pp. 419-439.
(1988), Kemeny & Challacombe, ELISA and Other Solid Phase Immunoassays, John Wiley & Sons, Chichester, U.K.
Khalifah, et al., (1996), Biochemistry, 35(15): pp. 4645-4654.
Odetti, et al., (1992), Diabetes, 441: pp. 153-159.
Grandhee & Monnier, (1991), J. Biol. Chem, 266: pp. 11649-11653.
Dyer, et al., (1991), J. Biol. Chem, 266: pp. 11654-11660.
Bunn and Higgins, (1981), Science, 213: pp. 222-224.
Smith and Thornalley, (1992), Eur. J. Biochem, 210: pp. 729-739.
Cervantes-Laurean, et al., (1993), Biochemistry, 32: pp. 1528-1534.
Lowery, et al., (1985), J. Biol. Chem, 260: pp. 11611-11618.
Khatami, et al., (1988), Life Sci, 43: pp. 1725-1731.
Hirsch, et al., (1995), Carbohyd. Res, 267: pp. 17-25.
Chen & Cerami, (1993), J. Carbohyd. Chem, 12: pp. 731-742.
Hirsch, et al., (1992), Carbohyd. Res, 232: pp. 125-130.
Ou & Wolff, (1993), Biochem. Pharmacol, 46: No. 7 pp. 1139-1144.
Wolff & Dean, (1987), Biochem. J. Pharmacol, 245: No. 8 pp. 243-250.
Wells-Knecht, et al., (1995), Biochemistry, 34: pp. 3702-3709.
Neglia, et al., (1983), J. Biol. Chm, 258: pp. 14279-14283.
Neglia, et al., (1985), J. Biol. Chem, 260: pp. 5406-5410.
Raetz and Auld, (1972), Biochemistry, 11: pp. 2229-2236.
(1992), Merck Manual of Diagnosis and Therapy, 16th edition (Merck & Co., Rathaway, N.J.), pp. 938-939.
Booth, et al., (1996) Biochemical and Biophysical Research Communications, US, Academic Press Inc., Orlando, Florida, 220:(1) pp. 113-119.
Williamson, et al., (1993), Diabetics, 42:pp. 801-8013.
Mayrovitz and Larsen, (1996), Microvasc. Res, 52:pp. 115-126.
Tesfaye, et al., (1994), Diabetologia, 37: pp. 847-854.
Ellis and Good, (1991), Metabolism, 40: pp. 1016-1019.
Oturai, et al., (1996), APMIS, 104: pp. 259-264.
Soulis-Liparota, et al., (1991), Diabetes, 40: pp. 1328-1334.
Yamauchi, et al., (1997), Diab. Res. Clin. Pract, 34: pp. 127-133.
Bucala, et al., (1994), Proc. Natl. Acad.Sci, 91:pp. 9441-9445.
Cameron and Cotter, (1994), Diav. Metab. Rev, 10: pp. 189-224.
Boulton and Malik, (1999), Organ Specific Vascular Changes. In Diabetic Angiopathy. Took, J.E., editor. New York: Oxford University Press. pp. 267-275.
Pyke, et al., (1999), Diabetes 48 (Suppl.I) 593(Abstr.)).
Fu, et al., (1996), J. Biol. Chem, 271: pp. 9982-9986.
Litchfield, et al., (1999), Int. J. Biochem, 31: pp. 1297-1305.
Oda and Keane, (1997), Kidney Internat. 52, Suppl. 2: S36-S38.
Smulders, et al., (1997), Eur. J. Clin. Invest, 27: pp. 997-1002.
Guijarro and Keane, (1993), Curr. Opin. Nephrol. Hypertens, 2: pp. 372-379.
Saito, T., (1997), Tohoku J. Exp. Med, 181: pp. 321-337.
Picard, et al., (1992), Proc. Natl. Acad. Sci. USA, 89: pp. 6876-6880.
Giardino, et al., (1998), Diabetes, 47: pp. 1114-1120.
Andrus, et al., (1998), J. Neurochem, 71: pp. 2041-2048.
Hall, et al, (1998), J. Neurosci. Res, 53: pp. 66-77.

Smith, et al., (1998), J. Histochem. Cytochem, 46: pp. 731-735.
Smith, et al., (1998), J. Neurochem, 70: pp. 2212-2215.
Cohen et al., J. Am. Soc. Nephrol. (7) 183-190.
(1990), The Pharmacological Basis of Therapeutics, 8th edition, ed. Gilman, Rall, Nies, and Taylor (Pergamon Pres, New York, pp. 1293-1294; pp. 1523-1540.
Reddy, et al., (1995), Biochem, 34: pp. 10872-10878.
Engvall, (1981), Methods Enzymol, 70: pp. 419-439.
(1998), Kemeny & Challacombe, ELISA and Other Solid Phase Immunoassays, John Wiley & Sons, Chichester, U.K.
Khalifah, et al., (1996), Biochemistry, 35(15): pp. 4645-4654.
Odetti, et al., (1992), Diabetes, 441: pp. 153-159.
Grandhee & Monnier, (1991), J. Biol. Chem, 266: pp. 11649-11653.
Dyer, et al., (1991), J. Biol. Chem, 266: pp. 11654-11660.
Bunn and Higgins, (1981), Science, 213: pp. 222-224.
Smith and Thornalley, (1992), Eur. J. Biochem, 210: pp. 729-739.
Cervantes-Laurean, et al., (1993), Biochemistry, 32: pp. 1528-1534.
Lowery, et al., (1985), J. Biol. Chem, 260: pp. 11611-11618.
Khatami, et al., (1988), Life Sci, 43: pp. 1725-1731.
Hirsch, et al., (1995), Carbohyd. Res, 267: pp. 17-25.
Chen & Cerami, (1993), J. Carbohyd. Chem, 12: pp. 731-742.
Hirsch, et al., (1992), Carbohyd. Res, 232: pp. 125-130.
Ou & Wolff, (1993), Biochem. Pharmacol, 46: No. 7 pp. 1139-1144.
Wolff & Dean, (1987), Biochem. J. Pharmacol, 245: No. 8 pp. 243-250.
Wells-Knechi, et al., (1995), Biochemistry, 34: pp. 3702-3709.
Neglia, et al., (1983), J. Biol. Chm, 258: pp. 14279-14283.
Neglia, et al., (1985), J. Biol. Chem, 260: pp. 5406-5410.
Raetz and Auld, (1972), Biochemistry, 11: pp. 2229-2236.
(1992), Merck Manual of Diagnosis and Therapy, 16th edition (Merck & Co., Rathaway, N.J.), pp. 938-939.
Khalifah, et al., (1999) Biochemical and Biophysical Research Communications, 257:(2) pp. 251-258.
Bucala, et al., (1994) Proceedings of the National Academy of Sciences of the United States of America, 91:(20) pp. 9441-9445.
Baynes, et al., (1998) Journal of the American Society of Nephrology, vol. 9, No. Program and Abstract, Issue pp. 628A.
Khalifah, et al., (1997) Journal of the American Society of Nephrology, 8: supp. S!, pp. A2988-A2988.
"The Merck Manual", (1987), Merck Sharp & Dohme Research Laboratories, Rahway, N.J., "Complications of Diabetes Mellitus", p. 2081.
Booth, et al., (1997) Journal of Biological Chemistry, US, American Society of Biological Chemists, Baltimore, MD, 272:(9) pp. 5430-5437.
Rath, et al., (1996) Journal of Applied Nutrition, 48/3, (68-78), Abstract, p. 68, figures 2-4 and p. 76, paragraph 2.
Jackson, et al., (1993) Biochemical Society Transactions, GB, Colchester, Essex, 21:(3) pp. 650-651.

* cited by examiner

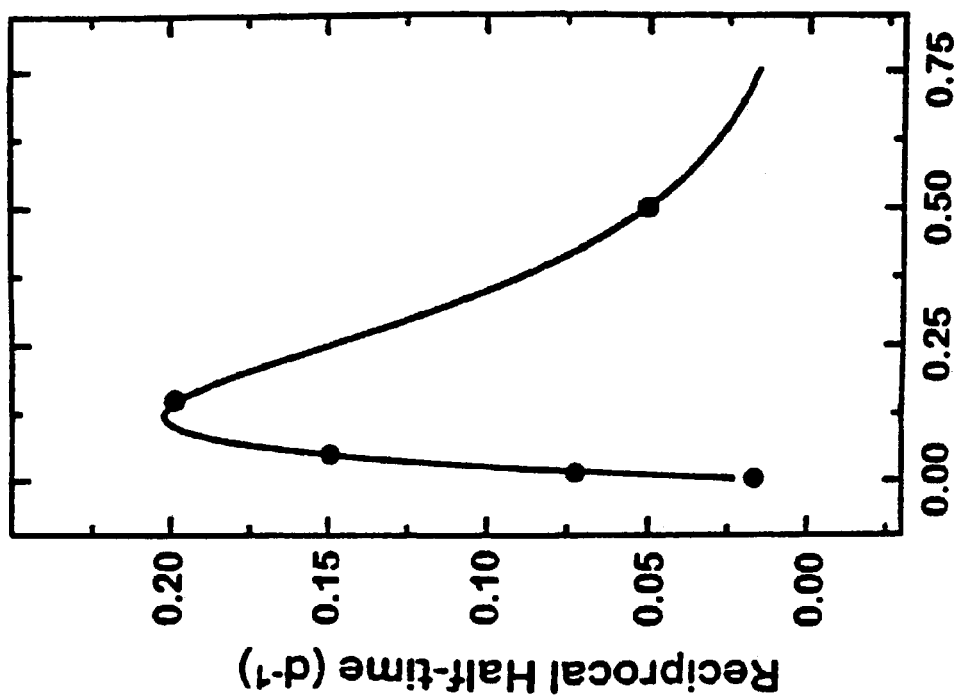
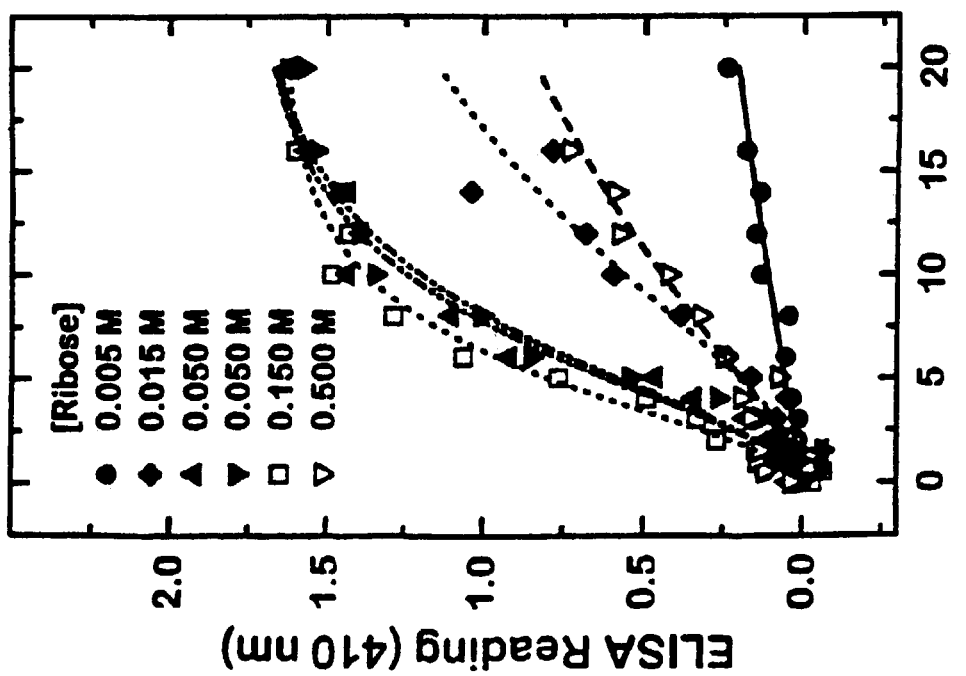
FIG. 6B
FIG. 6A

Scheme 2

Aminoguanidine

Scheme 3

Thiamine

Thiamine-5'-Phosphate

Thiamine Pyrophosphate

Scheme 4

Pyridoxine

Pyridoxamine

Pyridoxal-5'-Phosphate

Pyridoxal

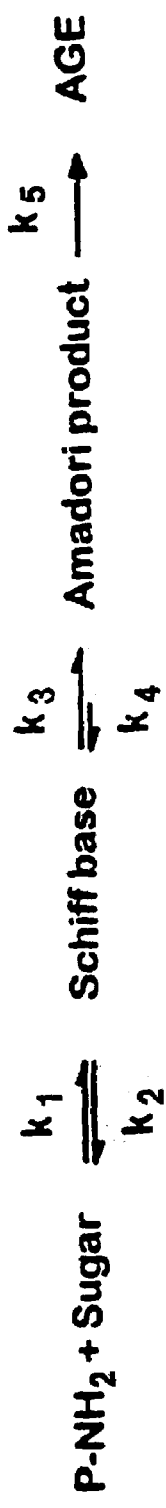
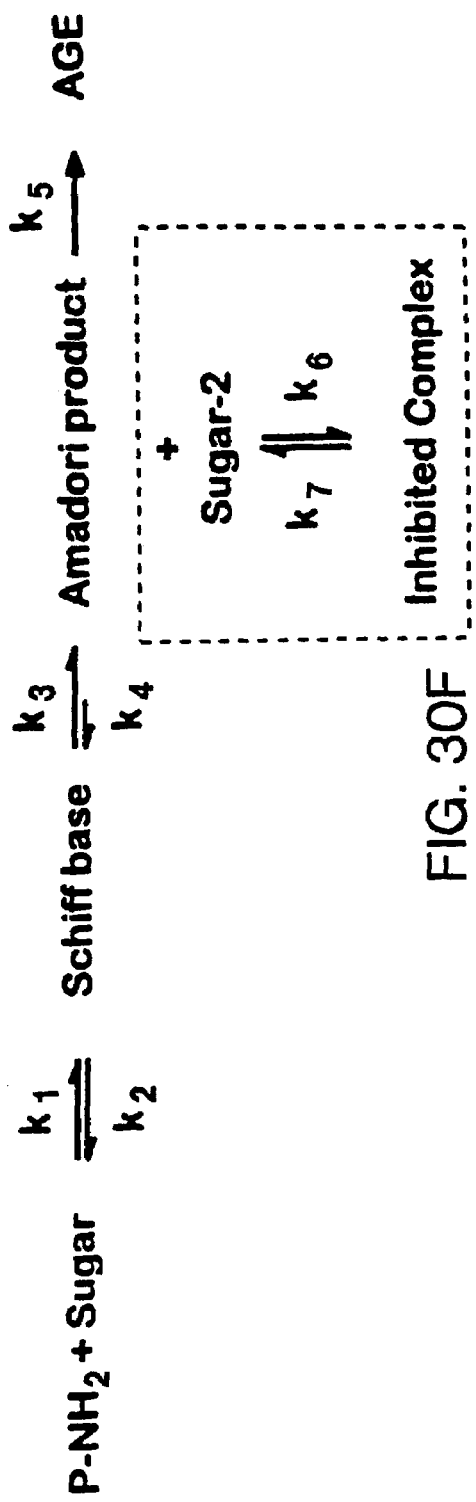
FIG. 30E
FIG. 30F

METHODS FOR TREATING DIABETIC NEUROPATHY

CROSS REFERENCE

This application is a continuation-in-part of U.S. Patent Applications, Ser. Nos. 60/105,182 filed Oct. 22, 1998; 08/971,285 filed Nov. 17, 1997 and 08/711,555, filed Sep. 10, 1996, and claims priority to U.S. Provisional Application for Patent Ser. No. 60/003,268, filed Sep. 12, 1995, the contents of each of which are hereby incorporated by reference in their entirety.

STATEMENT OF GOVERNMENT RIGHTS

Some of the work disclosed has been supported in part by NIH Grant DK 43507 1, therefore, the United States Government may have certain rights in the invention.

BACKGROUND OF THE INVENTION

The instant invention is in the field of Advanced Glycation End-products (AGEs), their formation, detection, identification, inhibition, and inhibitors thereof.

Protein Aging and Advanced Glycosylation End-Products

Nonenzymatic glycation by glucose and other reducing sugars is an important post-translational modification of proteins that has been increasingly implicated in diverse pathologies. Irreversible nonenzymatic glycation and crosslinking through a slow, glucose-induced process may mediate many of the complications associated with diabetes. Chronic hyperglycemia associated with diabetes can cause chronic tissue damage which can lead to complications such as retinopathy, nephropathy, and atherosclerotic disease. (Cohen and Ziyadeh, 1996, *J. Amer. Soc. Nephrol.* 7:183–190). It has been shown that the resulting chronic tissue damage associated with long-term diabetes mellitus arise in part from in situ immune complex formation by accumulated immunoglobulins and/or antigens bound to long-lived structural proteins that have undergone Advanced Glycosylation End-product (AGE) formation. via non-enzymatic glycosylation (Brownlee et al., 1983, *J. Exp. Med.* 158:1739–1744). The primary protein target is thought to be extra-cellular matrix associated collagen. Nonenzymatic glycation of proteins, lipids, and nucleic acids may play an important role in the natural processes of aging. Recently protein advanced glycation has been associated with β-amyloid deposits and formation of neurofibrillary tangles in Alzheimer disease, and possibly other neurodegenerative diseases involving amyloidosis (Colaco and Harrington, 1994, *NeuroReport* 5: 859–861). Glycated proteins have also been shown to be toxic, antigenic, and capable of triggering cellular injury responses after uptake by specific cellular receptors (see for example, Vlassara, Bucala & Striker, 1994, *Lab. Invest.* 70:138–151; Vlassara et al., 1994, *PNAS(USA)* 91:11704–11708; Daniels & Hauser, 1992, *Diabetes* 41:1415–1421; Brownlee, 1994, *Diabetes* 43:836–841; Cohen et al., 1994, *Kidney Int.* 45:1673–1679; Brett et al., 1993, *Am. J. Path.* 143:1699–1712; and Yan et al., 1994, *PNAS(USA)* 91:7787–7791).

The appearance of brown pigments during the cooking of food is a universally recognized phenomenon, the chemistry of which was first described by Maillard in 1912, and which has subsequently led to research into the concept of protein aging. It is known that stored and heat-treated foods undergo nonenzymatic browning that is characterized by crosslinked proteins which decreases their bioavailibility. It was found that this Maillard reaction occurred in vivo as well, when it was found that a glucose was attached via an Amadori rearrangement to the amino-terminal of the a-chain of hemoglobin.

The instant disclosure teaches previously unknown, and unpredicted mechanism of formation of post-Amadori advanced glycation end products (Maillard products; AGEs) and methods for identifying and characterizing effective inhibitors of post-Amadori AGE formation. The instant disclosure demonstrates the unique isolation and kinetic characterization of a reactive protein intermediate competent in forming post-Amadori AGEs, and for the first time teaching methods which allow for the specific elucidation and rapid quantitative kinetic study of "late" stages of the protein glycation reaction.

In contrast to such "late" AGE formation, the "early" steps of the glycation reaction have been relatively well characterized and identified for several proteins (Harding, 1985, *Adv. Protein Chem.* 37:248–334; Monnier & Baynes eds., 1989, *The Maillard Reaction in Aging. Diabetes, and Nutrition* (Alan R. Liss, New York); Finot et al., 1990, eds. *The Maillard Reaction in Food Processing, Human Nutrition and Physiology* (Birkhauser Verlag, Basel)). Glycation reactions are known to be initiated by reversible Schiff-base (aldimine or ketimine) addition reactions with lysine side-chain ε-amino and terminal α-amino groups, followed by essentially irreversible Amadori rearrangements to yield ketoamine products e.g. 1-amino-1-deoxy-ketoses from the reaction of aldoses (Baynes et al., 1989, in *The Maillard Reaction in Aging Diabetes, and Nutrition*, ed. Monnier and Baynes, (Alan R. Liss, New York, pp 43–67). Typically, sugars initially react in their open-chain (not the predominant pyranose and furanose structures) aldehydo or keto forms with lysine side chain ε-amino and terminal α-amino groups through reversible Schiff base condensation (Scheme I). The resulting aldimine or ketimine products then undergo Amadori rearrangements to give ketoamine Amadori products, i.e. 1-amino-1-deoxy-ketoses from the reaction of aldoses (Means & Chang, 1982, *Diabetes* 31, Suppl. 3:1–4; Harding, 1985, *Adv. Protein Chem.* 37:248–334). These Amadori products then undergo, over a period of weeks and months, slow and irreversible Maillard "browning" reactions, forming fluorescent and other products via rearrangement, dehydration, oxidative fragmentation, and cross-linking reactions. These post-Amadori reactions, (slow Maillard "browning" reactions), lead to poorly characterized Advanced Glycation End-products (AGEs).

As with Amadori and other glycation intermediaries, free glucose itself can undergo oxidative reactions that lead to the production of peroxide and highly reactive fragments like the dicarbonyls glyoxal and glycoaldehyde. Thus the elucidation of the mechanism of formation of a variety of AGEs has been extremely complex since most in vitro studies have been carried out at extremely high sugar concentrations.

In contrast to the relatively well characterized formation of these "early" products, there has been a clear lack of understanding of the mechanisms of forming the "late" Maillard products produced in post-Arnadori reactions, because of their heterogeneity, long reaction times, and complexity. The lack of detailed information about the chemistry of the "late" Maillard reaction stimulated research to identify fluorescent AGE chromophores derived from the reaction of glucose with amino groups of polypeptides. One such chromophore, 2-(2-furoyl)-4(5)-(2-furanyl)-1H-imidazole (FFI) was identified after nonenzymatic browning of bovine serum albumin and polylysine with glucose, and postulated to be representative of the chromophore present in the intact polypeptides. (Pongor et al., 1984, *PNAS(USA)* 81:2284–2688). Later studies established FFI to be an artifact formed during acid hydrolysis for analysis.

A series of U.S. Patents have issued in the area of inhibition of protein glycosylation and cross-linking of protein sugar amines based upon the premise that the mechanism of such glycosylation and cross-linking occurs via saturated glycosylation and subsequent cross-linking of protein sugar amines via a single basic, and repeating reaction. These patents include U.S. Pat. Nos. 4,665,192; 5,017,696; 4,758,853; 4,908,446; 4,983,604; 5,140,048; 5,130,337; 5,262,152; 5,130,324; 5,272,165; 5,221,683; 5,258,381; 5,106,877; 5,128,360; 5,100,919; 5,254,593; 5,137,916; 5,272,176; 5,175,192; 5,218,001; 5,238,963; 5,358,960; 5,318,982; and 5,334,617. (All U.S. Patents cited are hereby incorporated by reference in their entirety).

The focus of these U.S. Patents, are a method for inhibition of AGE formation focused on the carbonyl moiety of the early glycosylation Amadori product, and in particular the most effective inhibition demonstrated teaches the use of exogenously administered aminoguanidine. The effectiveness of aminoguanidine as an inhibitor of AGE formation is currently being tested in clinical trials.

Inhibition of AGE formation has utility in the areas of, for example, food spoilage, animal protein aging, and personal hygiene such as combating the browning of teeth. Some notable, though quantitatively minor, advanced glycation end-products are pentosidine and $N^\epsilon$-carboxymethyllysine (Sell and Monnier, 1989, *J. Biol. Chem.* 264:21597–21602; Ahmed et al., 1986, *J. Biol. Chem.* 261:4889–4894).

The Amadori intermediary product and subsequent post-Amadori AGE formation, as taught by the instant invention, is not fully inhibited by reaction with aminoguanidine. Thus, the formation of post-Amadori AGEs as taught by the instant disclosure occurs via an important and unique reaction pathway that has not been previously shown, or even previously been possible to demonstrate in isolation. It is a highly desirable goal to have an efficient and effective method for identifying and characterizing effective post-Amadori AGE inhibitors of this "late" reaction. By providing efficient screening methods and model systems, combinatorial chemistry can be employed to screen candidate compounds effectively, and thereby greatly reducing time, cost, and effort in the eventual validation of inhibitor compounds. It would be very useful to have in vivo methods for modeling and studying the effects of post-Amadori AGE formation which would then allow for the efficient characterization of effective inhibitors.

Inhibitory compounds that are biodegradeble and/or naturally metabolized are more desirable for use as therapeutics than highly reactive compounds which may have toxic side effects, such as aminoguanidine.

SUMMARY OF THE INVENTION

In accordance with the present invention, a stable post-Amadori advanced glycation end-product (AGE) precursor has been identified which can then be used to rapidly complete the post-Amadori conversion into post-Amadori AGEs. This stable product is a presumed sugar saturated Amadori/Schiff base product produced by the further reaction of the early stage protein/sugar Amadori product with more sugar. In a preferred embodiment, this post-Amadori/Schiff base intermediary has been generated by the reaction of target protein with ribose sugar.

The instant invention provides for a method of generating stable protein-sugar AGE formation intermediary precursors via a novel method of high sugar inhibition. In a preferred embodiment the sugar used is ribose.

The instant invention provides for a method for identifying an effective inhibitor of the formation of late Maillard products comprising: generating stable protein-sugar post-Amadori advanced glycation end-product intermediates by incubating a protein with sugar at a sufficient concentration and for sufficient length of time to generate stable post-Amadori AGE intermediates; contacting said stable protein-sugar post-Amadori advanced glycation end-product intermediates with an inhibitor candidate; identifying effective inhibition by monitoring the formation of post-Amadori AGEs after release of the stable protein-sugar post-Amadori advanced glycation end-product intermediates from sugar induced equilibrium. Appropriate sugars include, and are not limited to ribose, lyxose, xylose, and arabinose. It is believed that certain conditions will also allow for use of glucose and other sugars. In a preferred embodiment the sugar used is ribose.

The instant invention teaches that an effective inhibitor of post-Amadori AGE formation via "late" reactions can be identified and characterized by the ability to inhibit the formation of post-Amadori AGE endproducts in an assay comprising; generating stable protein-sugar post-Amadori advanced glycation end-product intermediates by incubating a protein with sugar at a sufficient concentration and for sufficient length of time to generate stable post-Amadori AGE intermediates; contacting said stable protein-sugar post-Amadori advanced glycation end-product intermediates with an inhibitor candidate; identifying effective inhibition by monitoring the formation of post-Amadori AGEs after release of the stable protein-sugar post-Amadori advanced glycation end-product intermediates from sugar induced equilibrium. In a preferred embodiment the assay uses ribose.

Thus the methods of the instant invention allow for the rapid screening of candidate post-Amadori AGE formation inhibitors for effectiveness, greatly reducing the cost and amount of work required for the development of effective small molecule inhibitors of post-Amadori AGE formation. The instant invention teaches that effective inhibitors of post-Amadori "late" reactions of AGE formation include derivatives of vitamin $B_6$ and vitamin $B_1$, in the preferred embodiment the specific species being pyridoxamine and thiamine pyrophosphate.

The instant invention teaches new methods for rapidly inducing diabetes like pathologies in rats comprising administering ribose to the subject animal. Further provided for is the use of identified inhibitors pyridoxamine and thiamine pyrophosphate in vivo to inhibit post-Amadori AGE induced pathologies.

The present invention encompasses compounds for use in the inhibition of AGE formation and post-Amadori AGE pathologies, and pharmaceutical compositions containing

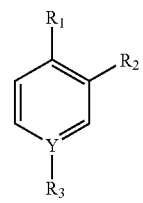

such compounds of the general formula:
Formula I
wherein $R_1$ is $CH_2NH_2$, $CH_2SH$, $COOH$, $CH_2CH_2NH_2$, $CH_2CH_2SH$, or $CH_2COOH$;
$R_2$ is OH, SH or $NH_2$;
Y is N or C, such that when Y is N $R_3$ is nothing, and when Y is C, $R_3$ is $NO_2$ or another electron withdrawing group; and salts thereof.

The present invention also encompasses compounds of the general formula

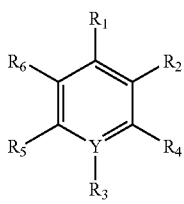

Formula II wherein $R_1$ is $CH_2NH_2$, $CH_2SH$, $COOH$, $CH_2CH_2NH_2$, $CH_2CH_2SH$, or $CH_2COOH$;

$R_2$ and $R_6$ is H, OH, SH, $NH_2$, C 1–18 alkyl alkoxy or alkene;

$R_4$ and $R_5$ are H, C 1–18 alkyl, alkoxy or alkene;

Y is N or C, such that when Y is N $R_3$ is nothing, and when Y is C, $R_3$ is $NO_2$ or another electron withdrawing group, and salts thereof In a preferred embodiment at least one of $R_4$, $R_5$ and $R_6$ are H.

In addition, the instant invention also envisions compounds of the formulas

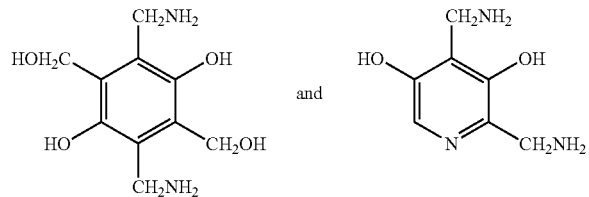

The compounds of the present invention can embody one or more electron withdrawing groups, such as and not limited to $-NH_2$, $-NHR$, $-NR_2$, $-OH$, $-OCH_3$, $-OCR$, and $-NH-COCH$ where R is C 1–6 alkyl.

The instant invention encompasses pharmaceutical compositions which comprise one or more of the compounds of the present invention, or salts thereof, in a suitable carrier. The instant invention encompasses methods for administering pharmaceuticals of the present invention for therapeutic intervention of pathologies which are related to AGE formation in vivo. In one preferred embodiment of the present invention the AGE related pathology to be treated is related to diabetic nephropathy.

The instant invention also teaches methods to treat or prevent diabetes associated hyperlipidemia, cellular redox imbalances, hypercholesterolemia, hypertriglyceridemia, and atherosclerosis, comprising administering the compounds of the invention to a mammal in need thereof.

BRIEF DESCRIPTION OF THE DRAWINGS

FIG. 1 is a series of graphs depicting the effect of vitamin $B_6$ derivatives on AGE formation in bovine serum albumin (BSA).

FIG. 2 is a series of graphs depicting the effect of vitamin $B_1$ derivatives and aminoguanidine (AG) on AGE formation in bovine serum albumin.

FIG. 3 is a series of graphs depicting the effect of vitamin $B_6$ derivatives on AGE formation in human methemoglobin (Hb).

FIG. 2C thiamine (T)

FIG. 6A is a graph of the kinetics of glycation of RNase A (10 mg/mL) by ribose as monitored by ELISA. FIG. 6B is a graph showing the dependence of reciprocal half-times on ribose concentration at pH 7.5.

FIG. 8 are two graphs showing kinetics of pentosidine fluorescence (arbitrary units) increase during uninterrupted and interrupted ribose glycation of RNase.

FIG. 10 are graphs of Post-Amadori inhibition of AGE formation by ribose.

FIG. 13 is a series of graphs depicting the effect of vitamin $B_6$ derivatives on AGE formation during uninterrupted glycation of ribonuclease A (RNase A) by ribose.

FIG. 14 is a series of graphs depicting the effect of vitamin $B_1$ derivatives and aminoguanidine (AG) on AGE formation during uninterrupted glycation of ribonuclease A (RNase A) by ribose.

FIG. 15 is a series of graphs depicting the effect of vitamin $B_6$ derivatives on AGE formation during uninterrupted glycation of bovine serum albumin (BSA) by ribose.

FIG. 16 is a series of graphs depicting the effect of vitamin $B_1$ derivatives and aminoguanidine (AG) on AGE formation during uninterrupted glycation of bovine serum albumin (BSA) by ribose.

FIG. 17 is a series of graphs depicting the effect of vitamin $B_6$ derivatives on AGE formation during uninterrupted glycation of human methemoglobin (Hb) by ribose.

Pyridoxamine (PM)

FIG. 18 is a series of graphs depicting the effect of vitamin $B_6$ derivatives on post-Amadori AGE formation after interrupted glycation by ribose.

FIG. 30E depicts Scheme 5, kinetics representation of AGE formation. FIG. 30F depicts Scheme 6, kinetics representation of AGE formation and intermediate formation.

DETAILED DESCRIPTION

Animal Models for Protein Aging

Figure 1A:
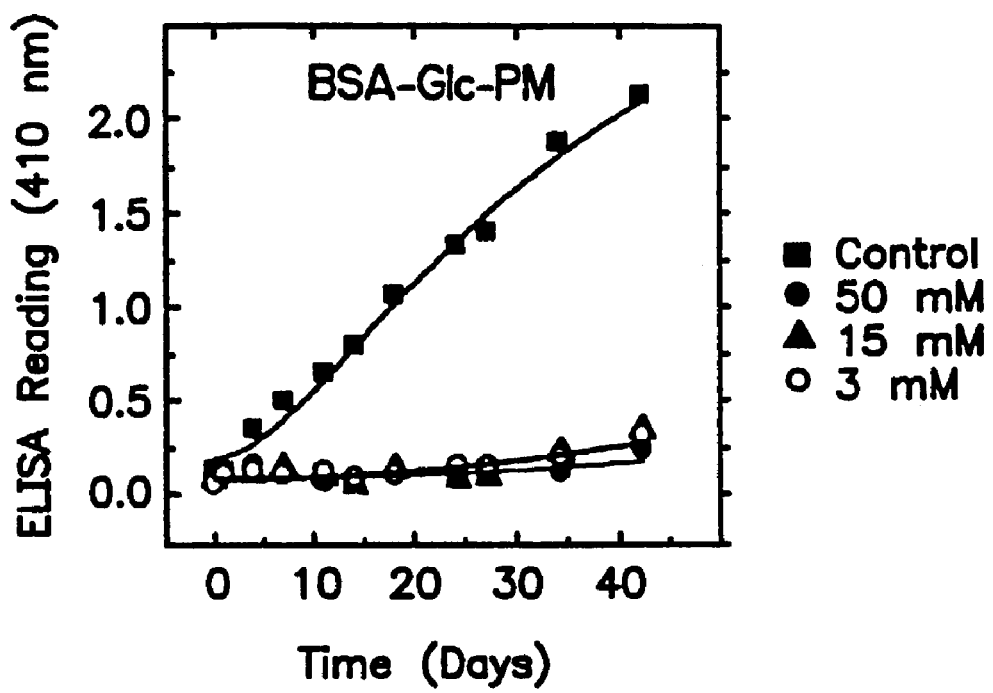
FIG. 1A Pyridoxamine (PM)
Figure 1B:
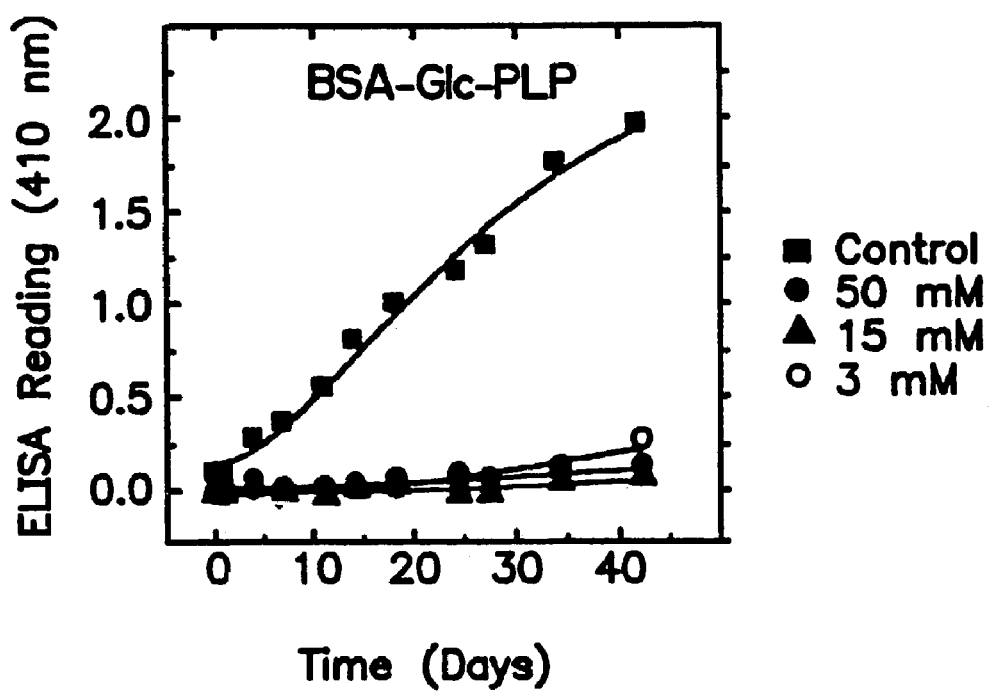
FIG. 1B pyridoxal phosphate (PLP)
Figure 1C:
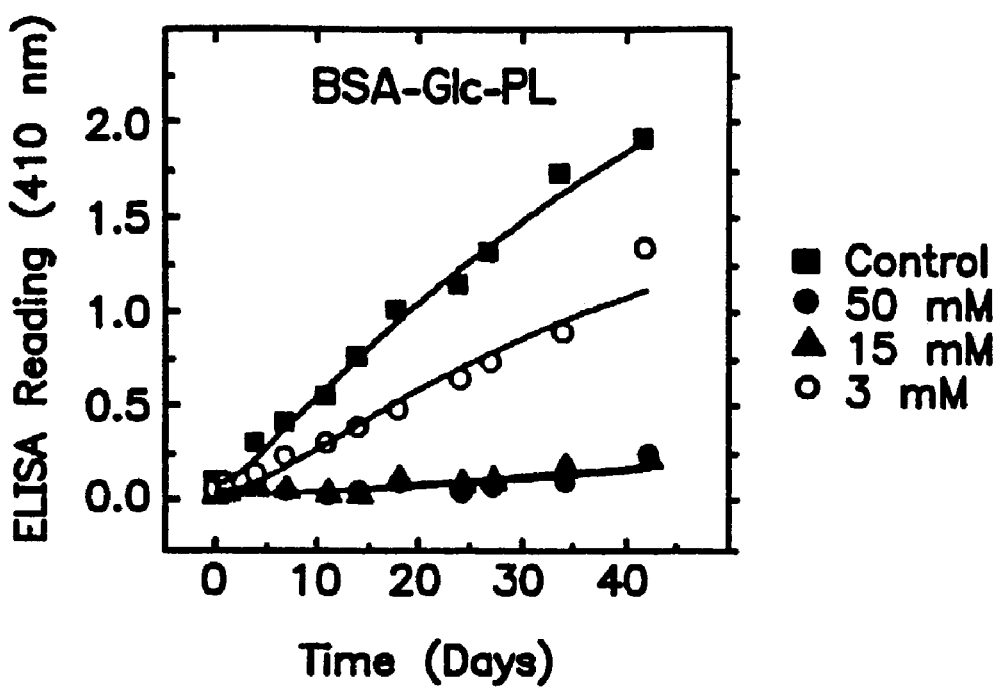
FIG. 1C pyridoxal (PL)
Figure 1D:
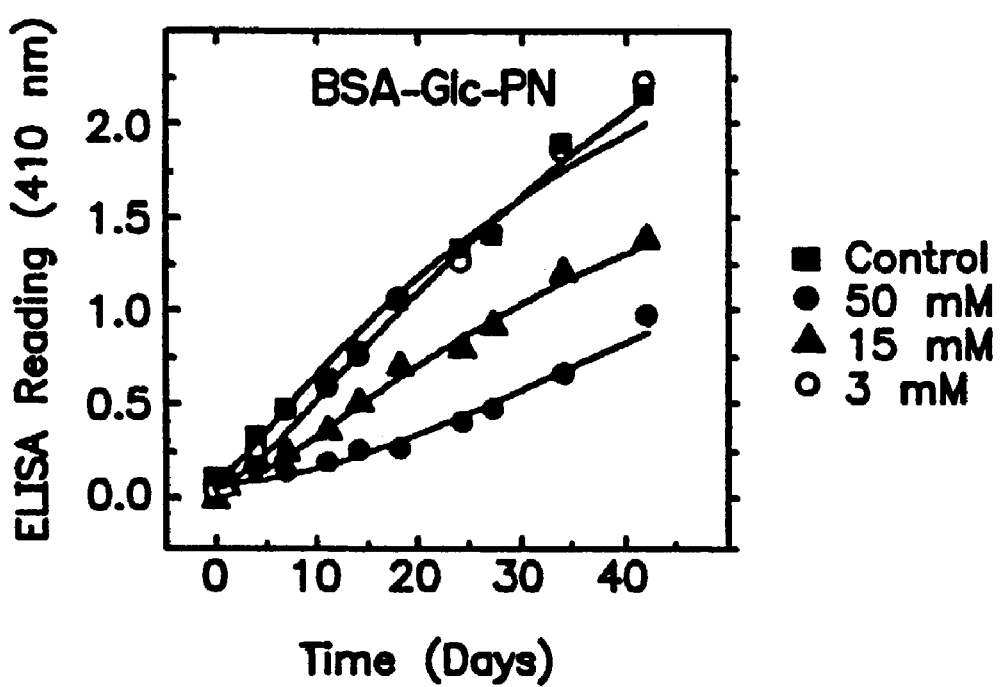
FIG. 1D pyridoxine (PN).
Figure 2A:
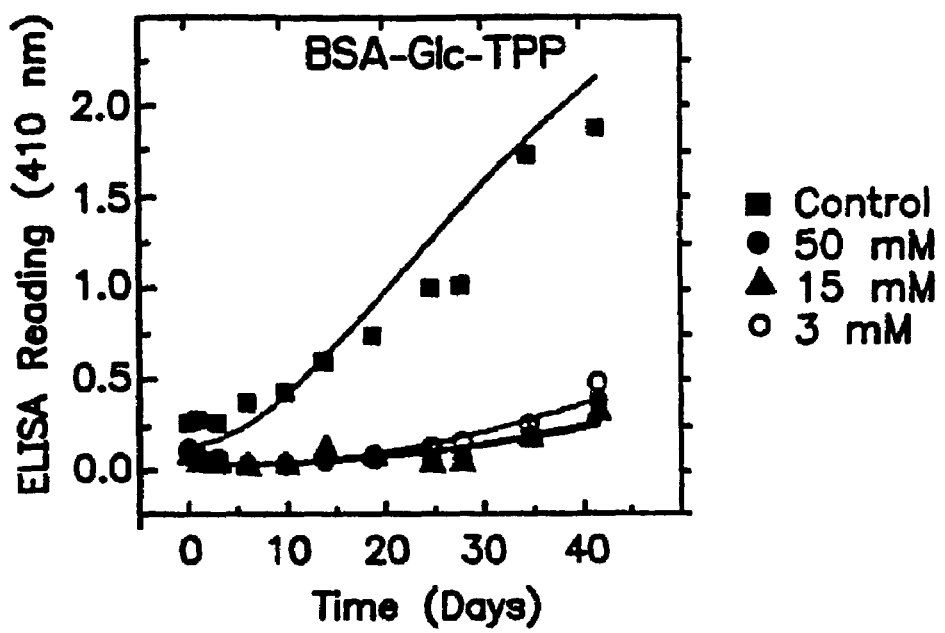
FIG. 2A Thiamine pyrophosphate (TPP)
Figure 2B:
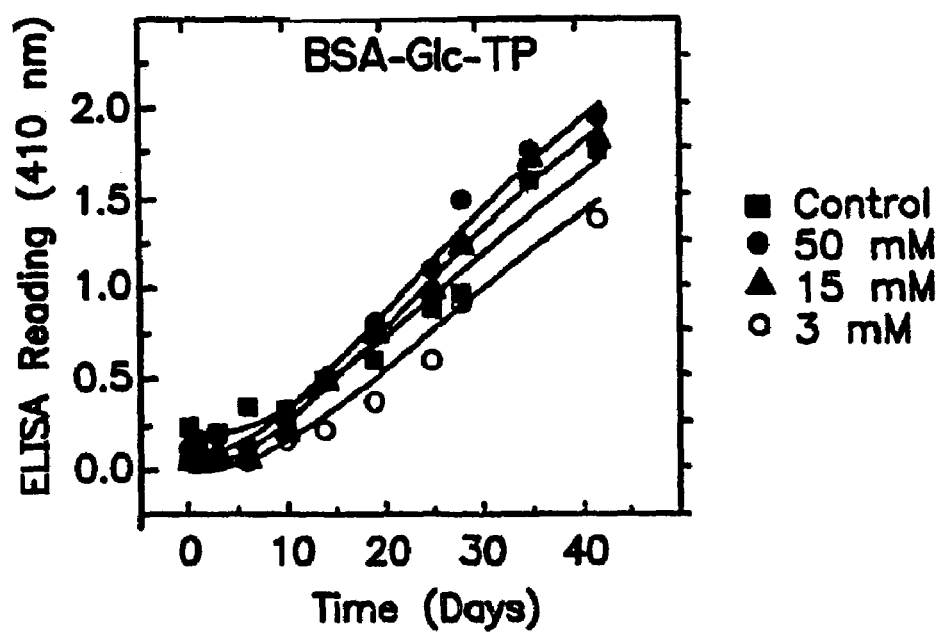
FIG. 2B thiamine monophosphate (TP)
Figure 2C:
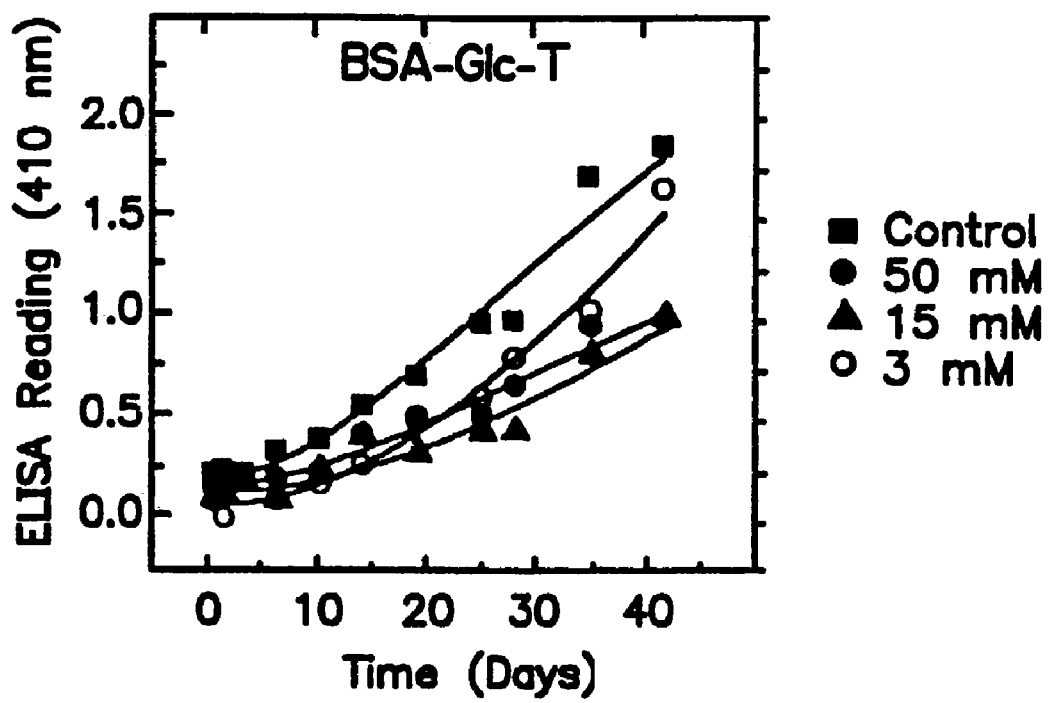
FIG. 2C thiamine (T)
Figure 2D:
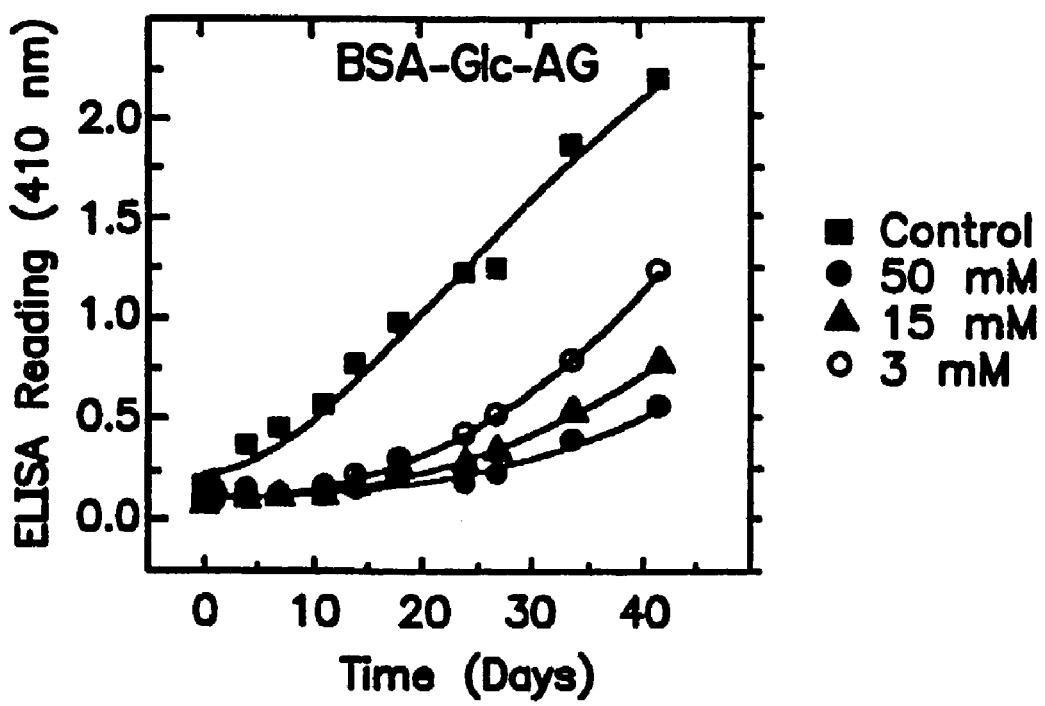
FIG. 2D aminoguanidine (AG).
Figure 3A:
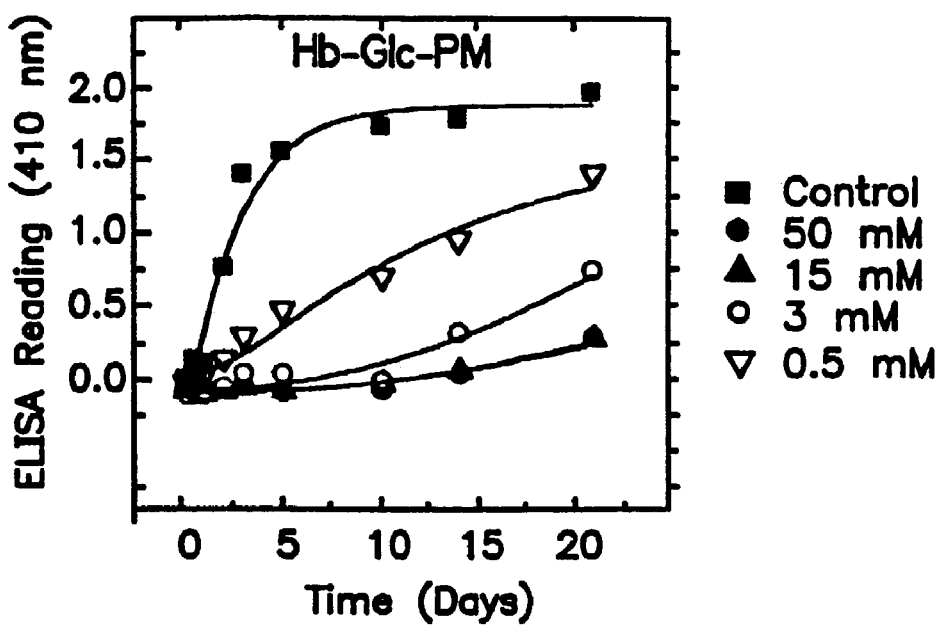
FIG. 3A Pyridoxamine (PM)
Figure 3B:
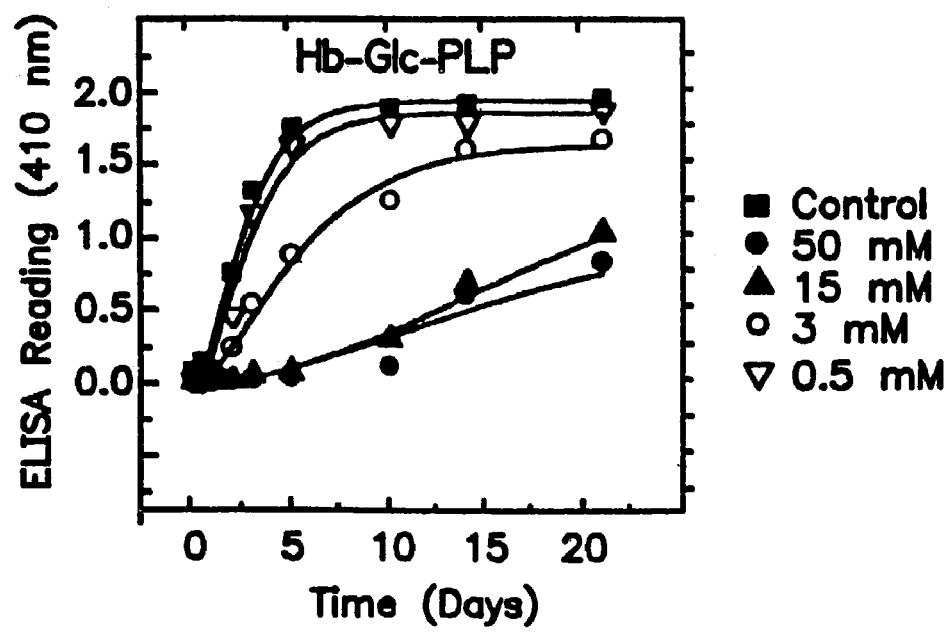
FIG. 3B pyridoxal phosphate (PLP)
Figure 3C:
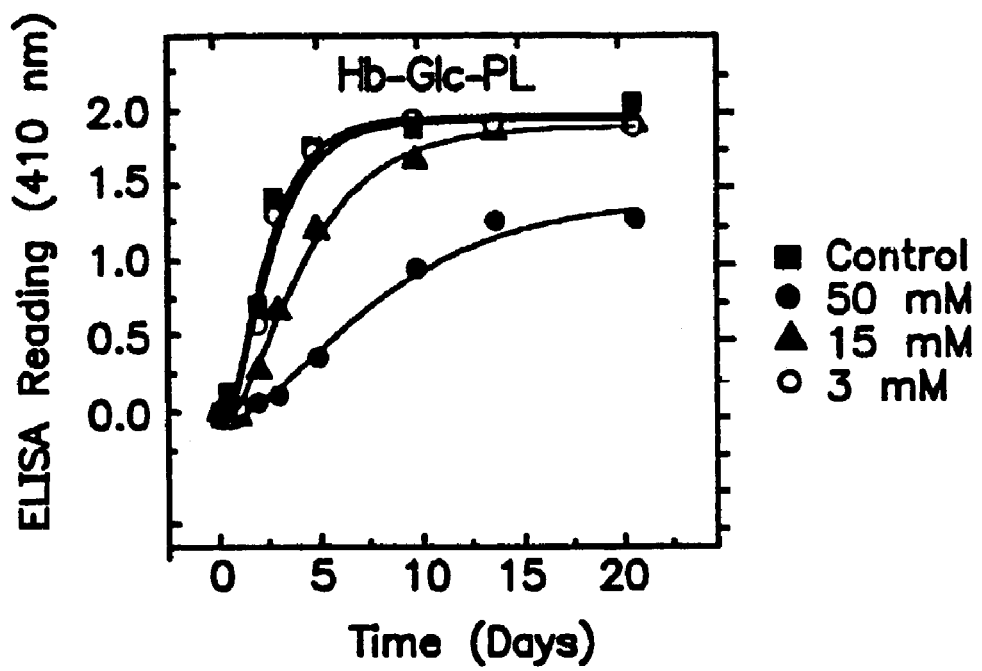
FIG. 3C pyridoxal (PL)
Figure 3D:
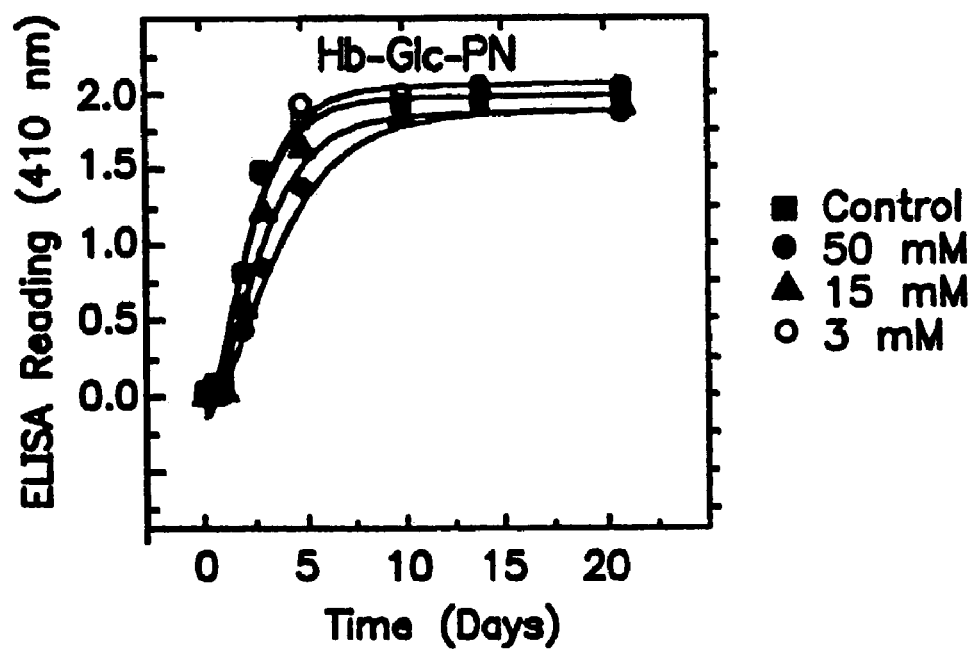
FIG. 3D pyridoxine (PN).

Alloxan induced diabetic Lewis rats have been used as a model for protein aging to demonstrate the in vivo effectiveness of inhibitors of AGE formation. The correlation being demonstrated is between inhibition of late diabetes related pathology and effective inhibition of AGE formation (Brownlee, Cerami, and Vlassara, 1988, *New Eng. J. Med.* 318(20):1315–1321). Streptozotocin induction of diabetes in Lewis rats, New Zealand White rabbits with induced diabetes, and genetically diabetic BB/Worcester rats have also been utilized, as described in, for example, U.S. Pat. No. 5,334,617 (incorporated by reference). A major problem with these model systems is the long time period required to demonstrate AGE related injury, and thus to test compounds for AGE inhibition. For example, 16 weeks of treatment was required for the rat studies described in U.S. Pat. No. 5,334,617, and 12 weeks for the rabbit studies. Thus it would be highly desirable and useful to have a model system for AGE related diabetic pathology that will manifest in a shorter time period, allowing for more efficient and expeditious determination of AGE related injury and the effectiveness of inhibitors of post-Amadori AGE formation.

Antibodies to AGEs

An important tool for studying AGE formation is the use of polyclonal and monoclonal antibodies that are specific for AGEs elicited by the reaction of several sugars with a variety of target proteins. The antibodies are screened for resultant specificity for AGEs that is independent of the nature of the protein component of the AGE (Nakayama et al., 1989, *Biochem. Biophys. Res. Comm.* 162: 740–745; Nakayama et al., 1991, *J. Immunol. Methods* 140: 119–125; Horiuchi et al., 1991, *J. Biol. Chem.* 266: 7329–7332; Araki et al., 1992, *J. Biol. Chem.* 267: 10211–10214; Makita et al., 1992, *J. Biol. Chem.* 267: 5133–5138). Such antibodies have been used to monitor AGE formation in vivo and in vitro.

Thiamine—Vitamin $B_1$

The first member of the Vitamin B complex to be identified, thiamine is practically devoid of pharmacodynamic actions when given in usual therapeutic doses; and even large doses were not known to have any effects. Thiamine pyrophosphate is the physiologically active form of thiamine, and it functions mainly in carbohydrate metabolism as a coenzyme in the decarboxylation of α-keto acids. Tablets of thiamine hydrochloride are available in amounts ranging from 5 to 500 mg each. Thiamine hydrochloride injection solutions are available which contain 100 to 200 mg/ml.

For treating thiamine deficiency, intravenous doses of as high as 100 mg/L of parenteral fluid are commonly used, with the typical dose of 50 to 100 mg being administered. GI absorption of thiamine is believed to be limited to 8 to 15 mg per day, but may be exceed by oral administration in divided doses with food.

Repeated administration of glucose may precipitate thiamine deficiency in under nourished patients, and this has been noted during the correction of hyperglycemia.

Surprisingly, the instant invention has found, as shown by in vitro testing, that administration of thiamine pyrophosphate at levels above what is normally found in the human body or administered for dietary therapy, is an effective inhibitor of post-Amadori antigenic AGE formation, and that this inhibition is more complete than that possible by the administration of aminoguanidine.

Pyridoxine—Vitamin $B_6$

Vitamin $B_6$ is typically available in the form of pyridoxine hydrochloride in over-the-counter preparations available from many sources. For example Beach pharmaceuticals Beelith Tablets contain 25 mg of pyridoxine hydrochloride that is equivalent to 20 mg of $B_6$, other preparations include Marlyn Heath Care Marlyn Formula 50 which contain 1 mg of pyridoxine HCl and Marlyn Formula 50 Mega Forte which contains 6 mg of pyridoxine HCl, Wyeth-Ayerst Stuart Prenatal® tablets which contain 2.6 mg pyridoxine HCl, J&J-Merck Corp. Stuart Formula % tablets contain 2 mg of pyridoxine HCl, and the CIBA Consumer Sunkist Children's chewable multivitamins which contain 1.05 mg of pyridoxine HCl, 150% of the U.S. RDA for children 2 to 4 years of age, and 53% of the U.S. RDA for children over 4 years of age and adults. (Physician's Desk Reference for nonprescription drugs, 14th edition (Medical Economics Data Production Co., Montvale, N.J., 1993).

There are three related forms of pyridoxine, which differ in the nature of the substitution on the carbon atom in position 4 of the pyridine nucleus: pyridoxine is a primary alcohol, pyridoxal is the corresponding aldehyde, and pyridoxamine contains an aminomethyl group at this position. Each of these three forms can be utilized by mammals after conversion by the liver into pyridoxal-5'-phosphate, the active form of the vitamin. It has long been believed that these three forms are equivalent in biological properties, and have been treated as equivalent forms of vitamin $B_6$ by the art. The Council on Pharmacy and Chemistry has assigned the name pyridoxine to the vitamin.

The most active antimetabolite to pyridoxine is 4-deoxypyridoxine, for which the antimetabolite activity has been attributed to the formation in vivo of 4-deoxypyridoxine-5-phosphate, a competitive inhibitor of several pyridoxal phosphate-dependent enzymes. The pharmacological actions of pyridoxine are limited, as it elicits no outstanding pharmacodynamic actions after either oral or intravenous administration, and it has low acute toxicity, being water soluble. It has been suggested that neurotoxicity may develop after prolonged ingestion of as little as 200 mg of pyridoxine per day. Physiologically, as a coenzyme, pyridoxine phosphate is involved in several metabolic transformations of amino acids including decarboxylation, transamination, and racemization, as well as in enzymatic steps in the metabolism of sulfur-containing and hydroxy-amino acids. In the case of transamination, pyridoxal phosphate is aminated to pyridoxamine phosphate by the donor amino acid, and the bound pyridoxamine phosphate is then deaminated to pyridoxal phosphate by the acceptor α-keto acid. Thus vitamin B complex is known to be a necessary dietary supplement involved in specific breakdown of amino acids. For a general review of the vitamin B complex see *The Pharmacological Basis of Therapeutics*, 8th edition, ed. Gilman, Rall, Nies, and Taylor (Pergamon Press, New York, 1990, pp. 1293–4; pp. 1523–1540).

Surprisingly, the instant invention has discovered that effective dosages of the metabolically transitory pyridoxal amine form of vitamin $B_6$ (Pyridoxamine), at levels above what is normally found in the human body, is an effective inhibitor of post-Amadori antigenic AGE formation, and that this inhibition may be more complete than that possible by the administration of aminoguanidine.

Formation of Stable Amadori/Schiff Base Intermediary

The typical study of the reaction of a protein with glucose to form AGEs has been by ELISA using antibodies directed towards antigenic AGEs, and the detection of the production of an acid-stable fluorescent AGE, pentosidine, by HPLC following acid hydrolysis. Glycation of target proteins (i.e. BSA or RNase A) with glucose and ribose were compared by monitoring ELISA reactivity of polyclonal rabbit anti-Glucose-AGE-RNase and anti-Glucose-AGE-BSA antibodies. The antigen was generated by reacting 1 M glucose with RNase for 60 days and BSA for 90 days. The antibodies (R618 and R479) were screened and showed reactivity with only AGEs and not the protein, except for the carrier immunogen BSA.

EXAMPLE 1

Thiamine Pyrophosphate and Pyridoxamine Inhibit the Formation of Antigenic Advanced Glycation End-Products from Glucose: Comparison with Aminoguanidine Some $B_6$ vitamers, especially pyridoxat phosphate (PLP), have been previously proposed to act as "competitive inhibitors" of early glycation, since as aldehydes they themselves can form Schiff bases adducts with protein amino groups (Khatami et al., 1988, *Life Sciences* 43:1725–1731) and thus limit the amount of amines available for glucose attachment. However, effectiveness in limiting initial sugar attachment is not a predictor of inhibition of the conversion of any Amadori products formed to AGEs. The instant invention describes inhibitors of "late" glycation reactions as indicated by their effects on the in vitro formation of antigenic AGEs (Booth et al., 1996, *Biochem. Biophys. Res. Com.* 220: 113–119).

Chemicals Bovine pancreatic ribonuclease A (RNase) was chromatographically pure, aggregate-free grade from Worthington Biochemicals. Bovine Serum albumin (BSA; fraction V, fatty-acid free), human methemoglobin (Hb), D-glucose, pyridoxine, pyridoxal, pyridoxal 5'phosphate, pyridoxamine, thiamine, thiamine monophosphate, thiamine pyrophosphate, and goat alkaline phosphatase-conjugated anti-rabbit IgG were all from Sigma Chemicals. Aminoguanidine hydrochloride was purchased from Aldrich Chemicals.

Uninterrupted Glycation with Glucose Bovine serum albumin, ribonuclease A, and human hemoglobin were incubated with glucose at 37° C. in 0.4 M sodium phosphate buffer of pH 7.5 containing 0.02% sodium azide. The protein, glucose (at 1.0 M), and prospective inhibitors (at 0.5, 3, 15 and 50 mM) were introduced into the incubation mixture simultaneously. Solutions were kept in the dark in capped tubes. Aliquots were taken and immediately frozen until analyzed by ELISA at the conclusion of the reaction. The incubations were for 3 weeks (Hb) or 6 weeks (RNase, BSA).

Preparation of Polyclonal Antibodies to AGE Proteins

Immunogen preparation followed earlier protocols (Nakayama et al., 1989, *Biochem. Biophys. Res. Comm.* 162: 740–745; Horiuchi et al., 1991, *J. Biol. Chem.* 266:7329–7332; Makita et al., 1992, *J. Biol. Chem.*, 267: 5133–5138). Briefly, immunogen was prepared by glycation of BSA (R479 antibodies) or RNase (R618 antibodies) at 1.6 g protein in 15 ml for 60–90 days using 1.5 M glucose in 0.4 M sodium phosphate buffer of pH 7.5 containing 0.05% sodium azide at pH 7.4 and 37° C. New Zealand white rabbit males of 8–12 weeks were immunized by subcutaneous administration of a 1 ml solution containing 1 mg/ml of glycated protein in Freund's adjuvant. The primary injection used the complete adjuvant and three boosters were made at three week intervals with Freund's incomplete adjuvant. Rabbits were bled three weeks after the last booster. The serum was collected by centrifugation of clotted whole blood. The antibodies are AGE-specific, being unreactive with either native proteins (except for the carrier) or with Amadori intermediates. The polyclonal anti-AGE antibodies have proven to be a sensitive and valuable analytical tool for the study of "late" AGE formation in vitro and in vivo. The nature of the dominant antigenic AGE epitope or hapten remains in doubt, although recently it has been proposed that the protein glycoxidation product carboxymethyl lysine (CML) may be a dominant antigen of some antibodies (Reddy et al., 1995, *Biochem.* 34:10872–10878). Earlier studies have failed to reveal ELISA reactivity with model CmL compounds (Makita et al., 1992, *J. Biol. Chem.* 267: 5133–5138).

ELISA detection of AGE products The general method of Engvall (1981, *Methods Enzymol.* 70:419–439) was used to perform the ELISA. Typically, glycated protein samples were diluted to approximately 1.5 ug/ml in 0.1 M sodium carbonate buffer of pH 9.5 to 9.7. The protein was coated overnight at room temperature onto 96-well polystyrene plates by pippetting 200 ul of the protein solution in each well (0.3 ug/well). After coating, the protein was washed from the wells with a saline solution containing 0.05% Tween-20. The wells were then blocked with 200 ul of 1% casein in carbonate buffer for 2 h at 37° C. followed by washing. Rabbit anti-AGE antibodies were diluted at a titer of about 1:350 in incubation buffer, and incubated for 1 h at 37° C., followed by washing. In order to minimize background readings, antibodies R479 used to detect glycated RNase were raised against glycated BSA, and antibodies R618 used to detect glycated BSA and glycated Hb were raised against glycated RNase. An alkaline phosphatase-conjugated antibody to rabbit IgG was then added as the secondary antibody at a titer of 1:2000 or 1:2500 (depending on lot) and incubated for 1 h at 37° C., followed by washing. The p-nitrophenylphosphate substrate solution was then added (200 ul/well) to the plates, with the absorbance of the released p-nitrophenolate being monitored at 410 nm with a Dynatech MR 4000 microplate reader.

Controls containing unmodified protein were routinely included, and their readings were subtracted, the corrections usually being negligible. The validity of the use of the ELISA method in quantitatively studying the kinetics of AGE formation depends on the linearity of the assay (Kemeny & Challacombe, 1988, *ELISA and Other Solid Phase Immunoassays*, John Wiley & Sons, Chichester, U.K.). Control experiments were carried out, for example, demonstrating that the linear range for RNase is below a coating concentration of about 0.2–0.3 mg/well.

Results

FIGS. 1A–D are graphs which show the effect of vitamin $B_6$ derivatives on post-Amadori AGE formation in bovine serum albumin glycated with glucose. BSA (10 mg/ml) was incubated with 1.0 M glucose in the presence and absence of the various indicated derivative in 0.4 M sodium phosphate buffer of pH 7.5 at 37° C. for 6 weeks. Aliquots were assayed by ELISA using R618 anti-AGE antibodies. Concentrations of the inhibitors were 3, 15 and 50 mM. Inhibitors used in FIGS. (1A) Pyridoxamine (PM); (1B) pyridoxal phosphate (PLP); (1C) pyridoxal (PL); (1D) pyridoxine (PN).

FIG. 1 (control curves) demonstrates that reaction of BSA with 1.0 M glucose is slow and incomplete after 40 days, even at the high sugar concentration used to accelerate the reaction. The simultaneous inclusion of different concentrations of various $B_6$ vitamers markedly affects the formation of antigenic AGEs. (FIGS. 1A–D) Pyridoxamine and pyridoxal phosphate strongly suppressed antigenic AGE formation at even the lowest concentrations tested, while pyridoxal was effective above 15 mM. Pyridoxine was slightly effective at the highest concentrations tested.

FIGS. 2A–D are graphs which show the effect of vitamin $B_1$ derivatives and aminoguanidine (AG) on AGE formation in bovine serum albumin. BSA (10 mg/ml) was incubated with 1.0 M glucose in the presence and absence of the various indicated derivative in 0.4 M sodium phosphate buffer of pH 7.5 at 37° C. for 6 weeks. Aliquots were assayed by ELISA using R618 anti-AGE antibodies. Concentrations of the inhibitors were 3, 15 and 50 mM. Inhibitors used in FIGS. (2A) Thiamine pyrophosphate (TPP); (2B) thiamine monophosphate (TP); (2C) thiamine (T); (2D) aminoguanidine (AG).

Of the various $B_1$ vitamers similarly tested (FIGS. 2A–D), thiamine pyrophosphate was effective at all concentrations tested (FIG. 2C), whereas thiamine and thiamine monophosphate were not inhibitory. Most significantly it is remarkable to note the decrease in the final levels of AGEs formed observed with thiamine pyrophosphate, pyridoxal phosphate and pyridoxamine. Aminoguanidine (FIG. 2D) produced some inhibition of AGE formation in BSA, but less so than the above compounds. Similar studies were carried out with human methemaglobin and bovine ribonuclease A.

FIGS. 3A–D are graphs which show the effect of vitamin $B_6$ derivatives on AGE formation in human methemoglobin. Hb (1 mg/ml) was incubated with 1.0 M glucose in the presence and absence of the various indicated derivative in 0.4 M sodium phosphate buffer of pH 7.5 at 37° C. for 3 weeks. Aliquots were assayed by ELISA using R618 anti-AGE antibodies. Concentrations of the inhibitors were 0.5, 3, 15 and 50 mM. Inhibitors used in FIGS. (3A) Pyridoxamine (PM); (3B) pyridoxal phosphate (PLP); (3C) pyridoxal (PL); (3D) pyridoxine (PN).

Figure 4A:
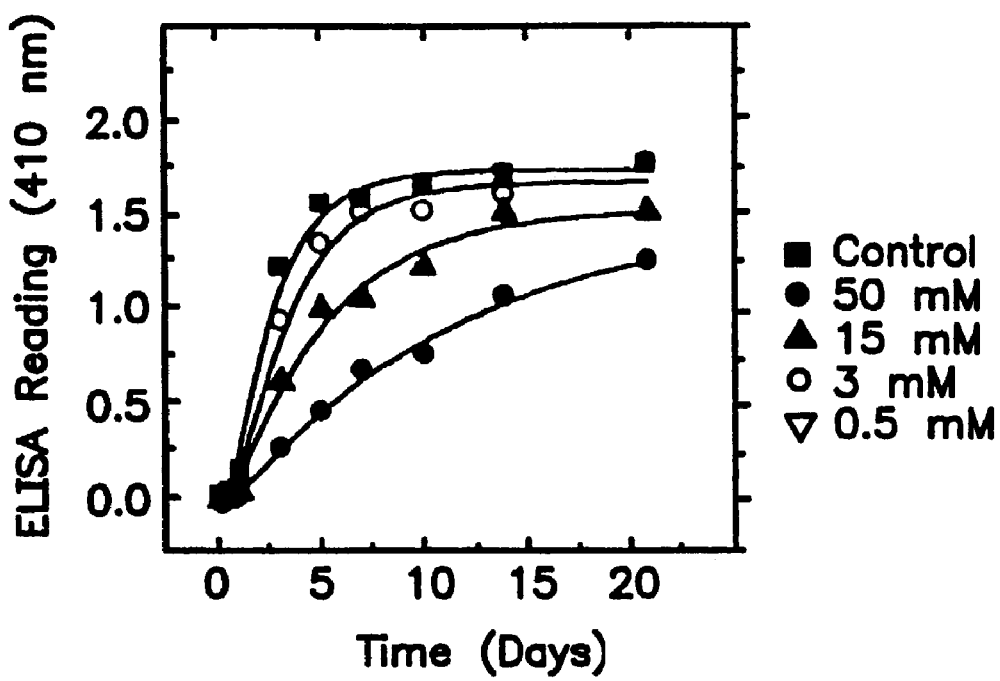
FIG. 4 is a series of graphs depicting the effect of vitamin $B_1$ derivatives and aminoguanidine (AG) on AGE formation in human methemoglobin.
Figure 4B:
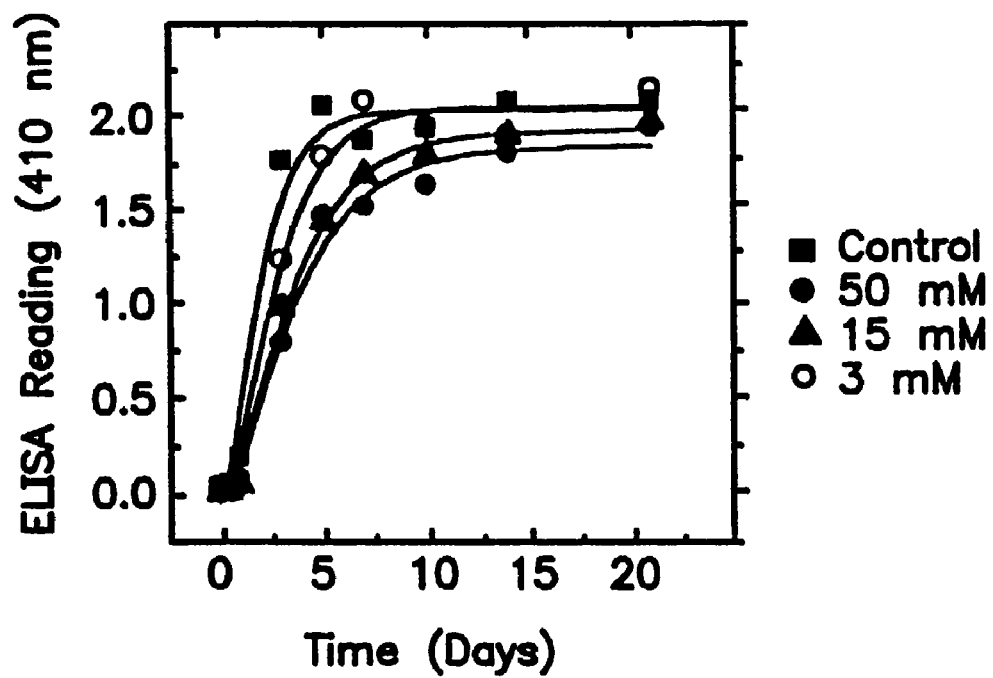
Figure 4C:
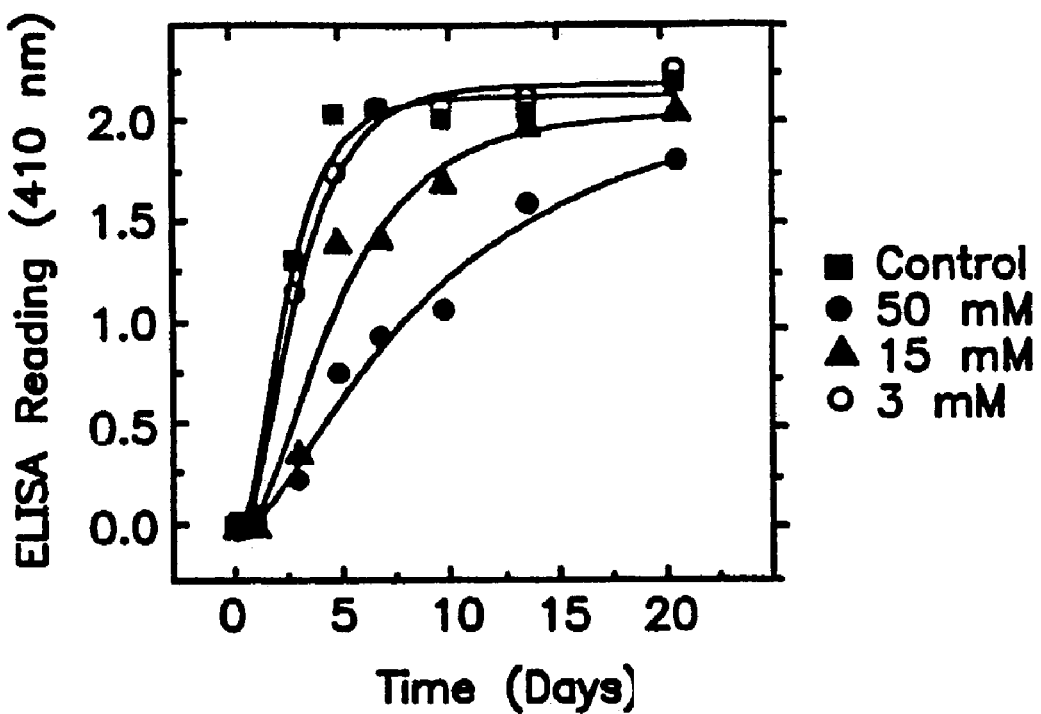
Figure 4D:
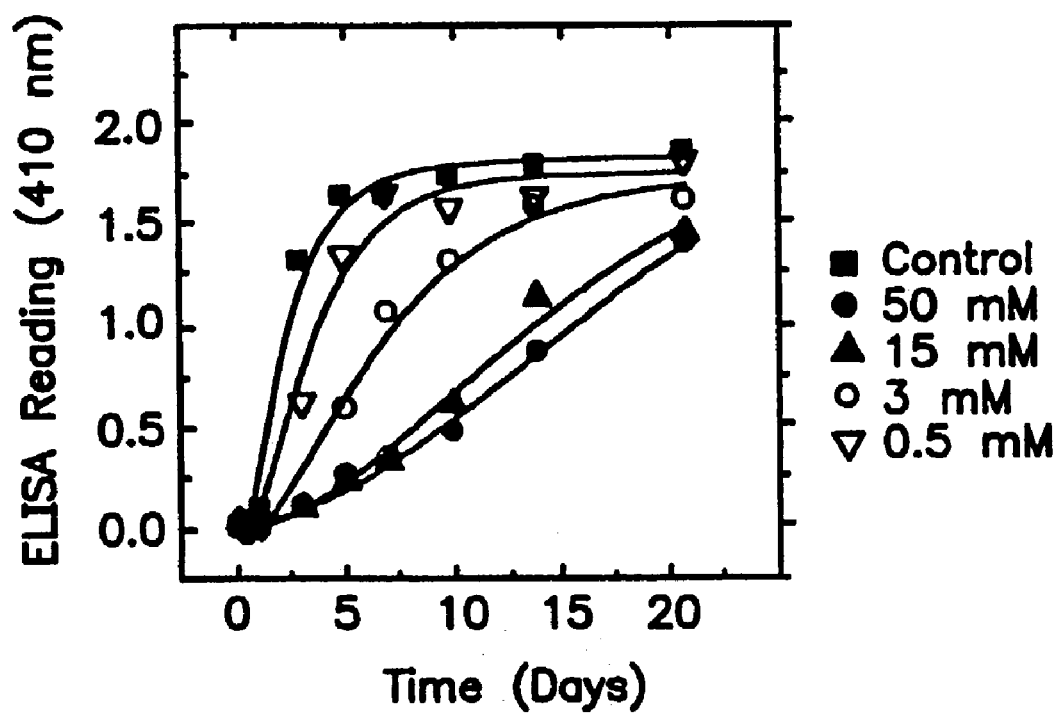

It had been previously reported that Hb of a diabetic patient contains a component that binds to anti-AGE antibodies, and it was proposed that this glycated Hb (termed Hb-AGE, not to be confused with HbAIc) could be useful in measuring long-term exposure to glucose. The in vitro incubation of Hb with glucose produces antigenic AGEs at an apparently faster rate than observed with BSA. Nevertheless, the different $B_6$ (FIGS. 3A–D) and $B_1$ (FIGS. 4A–C) vitamers exhibited the same inhibition trends in Hb, with pyridoxamine and thiamine pyrophosphate being the most effective inhibitors in each of their respective families. Significantly, in Hb, aminoguanidine only inhibited the rate of AGE formation, and not the final levels of AGE formed (FIG. 4D).

With RNase the rate of antigenic AGE formation by glucose was intermediate between that of Hb and BSA, but the extent of inhibition within each vitamer series was maintained. Again pyridoxamine and thiamine pyrophosphate were more effective that aminoguanidine (FIG. 5).

FIGS. 4A–D are graphs which show the effect of vitamin $B_1$ derivatives and aminoguanidine (AG) on AGE formation in human methemoglobin. Hb (1 mg/ml) was incubated with 1.0 M glucose in the presence and absence of the various indicated derivative in 0.4 M sodium phosphate buffer of pH 7.5 at 37° C. for 3 weeks. Aliquots were assayed by ELISA using R618 anti-AGE antibodies. Concentrations of the inhibitors were 0.5, 3, 15 and 50 mM. Inhibitors used in FIGS. (4A) Thiamine pyrophosphate (TPP); (4B) thiamine monophosphate (TP); (4C) thiamine (T); (4D) aminoguanidine (AG).

Figure 5:
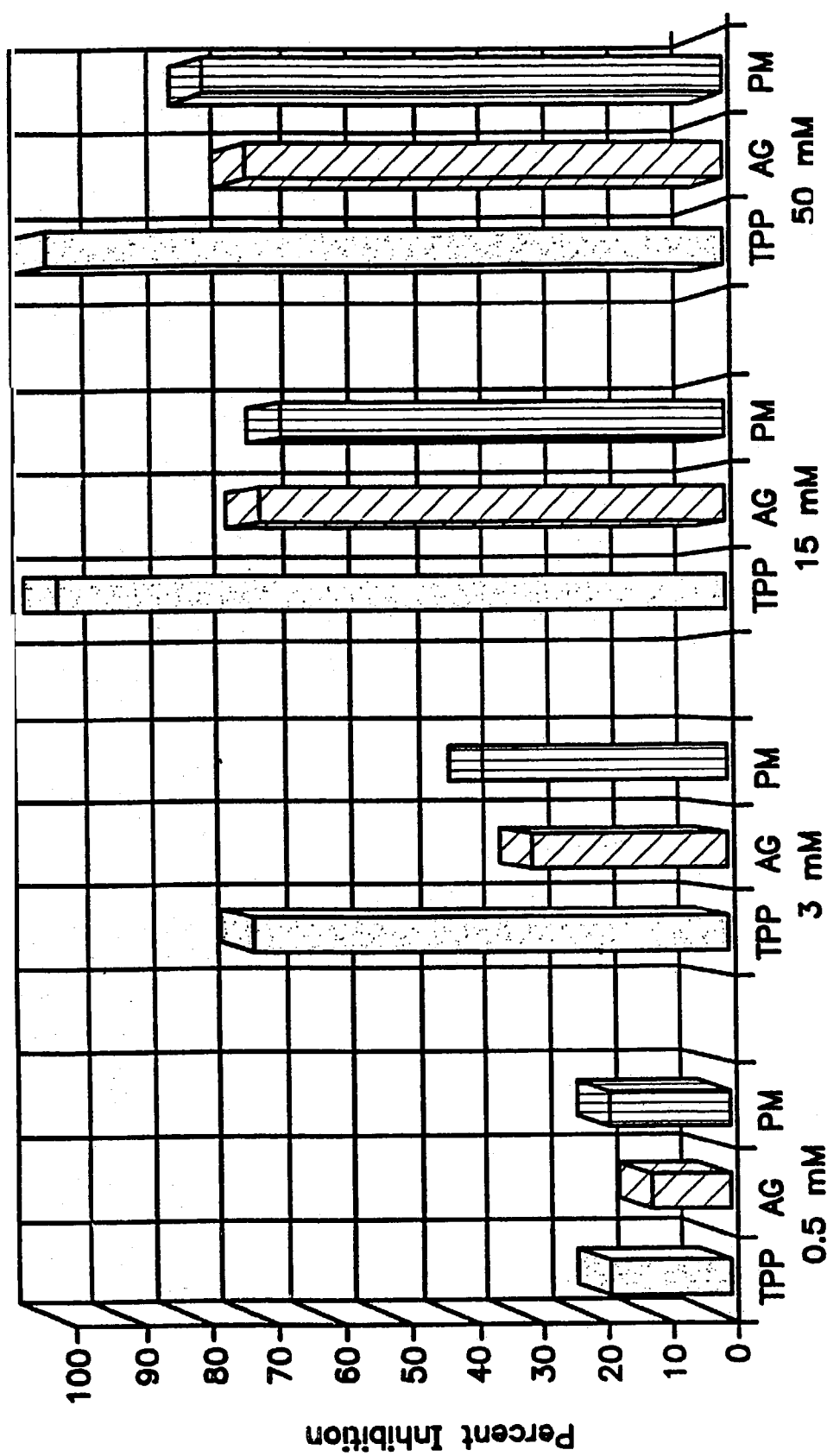
FIG. 5 is a bar graph comparison of the inhibition of the glycation of ribonuclease A by thiamine pyrophosphate (TPP), pyridoxamine (PM) and aminoguanidine (AG).

FIG. 5 is a bar graph which shows a comparison of the inhibition of the glycation of products, or with post-Amadori intermediates. The mechanism of inhibition of $B_1$ compounds is not obvious. All the forms contain an amino functionality, so that the marked efficiency of only the pyrophosphate form suggests an important requirement for a strong negative charge.

A significant unexpected observation is that the extent of inhibition by aminoguanidine, and some of the other compounds, is considerably less at late stages of the reaction, than during the early initial phase. This suggests a different mechanism of action than that of pyridoxamine and thiamine pyrophosphate, suggesting that the therapeutic potential of these compounds will be enhanced by co-administration with aminoguanidine.

EXAMPLE 2

Kinetics of Non-enzymatic Glycation: Paradoxical Inhibition by Ribose and Facile Isolation of Protein Intermediate for Rapid Post-Amadori AGE Formation While high concentrations of glucose are used to cause the non-enzymatic glycation of proteins, paradoxically, it was found that ribose at high concentrations is inhibitory to post-Amadori AGE formation in ribonuclease by acting on the post-Amadori "late" stages of the glycation reaction. This unexpectedly inhibitory effect suggests that the "early" reactive intermediates, presumably Amadori products, can be accumulated with little formation of "late" post-Amadori AGE products (AGEs; Maillard products). Investigation into this phenomenon has demonstrated: (1) ability to define conditions for the kinetic isolation of Amadori (or post-Amadori) glycated intermediate(s); (2) the ability study the fast kinetics of buildup of such an intermediate; (3) the ability to study the surprisingly rapid kinetics of conversion of such intermediates to AGE products in the absence of free or reversibly bound sugar; (4) the ability to use these intermediates to study and characterize inhibition of post-Amadori steps of AGE formation thus providing a novel system to investigate the mechanism of reaction and the efficacy of potential agents that could block AGE formation; and (5) with this knowledge it is also further possible to use $^{13}C$ NMR to study the reactive intermediates and monitor their conversion to various candidate AGEs (Khalifah et al., 1996, *Biochemistry* 35(15):4645–4654).

Chemicals and Materials As in Example 1 above.

Preparation of polyclonal antibodies to AGEs As in Example 1 above.

ELISA detection of AGE products As in Example 1 above.

Amino Acid Analysis Amino acid analyses were carried out at the Biotechnology Support Facility of the Kansas University Medical Center. Analyses were performed after hydrolysis of glycated protein (reduced with sodium cyanoborohydride) with 6 N HCl at 110° C. for 18–24 h. Phenyl isothiocyanate was used for derivatization, and PTH derivatives were analyzed by reverse-phase HPLC on an Applied Biosystems amino acid analyzer (420A derivatizer, 130A separation system, 920A data analysis system).

Pentosidine Reverse-Phase HPLC Analysis Pentosidine production in RNase was quantitated by HPLC (Sell & Monnier, 1989, *J. Biol. Chem.* 264:21597–21602; Odetti et al., 1992, *Diabetes* 41:153–159). Ribose-modified protein samples were hydrolyzed in 6 N HCl for 18 h at 100° C. and then dried in a Speed Vac. The samples were then redissolved, and aliquots were taken into 0.1% trifluoroacetic acid and analyzed by HPLC on a Shimadzu system using a Vydac C-18 column equilibrated with 0.1% TFA. A gradient of 0–6% acetonitrile (0.1% in TFA) was run in 30 min at a flow rate of about 1 ml/min. Pentosidine was detected by 335 nm excitation/385 nm emission fluorescence, and its elution time was determined by running a synthesized standard. Due to the extremely small levels of pentosidine expected (Grandhee & Monnier, 1991, *J. Biol. Chem.* 266: 11649–11653; Dyer et al., 1991, *J. Biol. Chem.* 266:11654–11660), no attempt was made to quantitate the absolute concentrations. Only relative concentrations were determined from peak areas.

Glycation Modifications Modification with ribose or glucose was generally done at 37° C. in 0.4 M phosphate buffer of pH 7.5 containing 0.02% sodium azide. The high buffer concentration was always used with 0.5 M ribose modifications. The solutions were kept in capped tubes and opened only to remove timed aliquots that were immediately frozen for later carrying out the various analyses. "Interrupted glycation" experiments were carried out by first incubating protein with the ribose at 37° C. for 8 or 24 h, followed by immediate and extensive dialysis against frequent cold buffer changes at 4° C. The samples were then reincubated by quickly warming to 37° C. in the absence of external ribose. Aliquots were taken and frozen at various intervals for later analysis. Due to the low molecular weight of RNase, protein concentrations were remeasured after dialysis even when low molecular weight cut-off dialysis tubing was used. An alternative procedure was also devised (see below) in which interruption was achieved by simple 100-fold dilution from reaction mixtures containing 0.5 M ribose. Protein concentrations were estimated from UV spectra. The difference in molar extinction between the peak (278 nm) and trough (250 nm) was used for RNase concentration determinations in order to compensate for the general increase in UV absorbance that accompanies glycation. Time-dependent UV-difference spectral studies were carried out to characterize the glycation contributions of the UV spectrum.

Data Analysis and Numerical Simulations of Kinetics Kinetic data were routinely fit to monoexponential or biexponential functions using nonlinear least-squares methods. The kinetic mechanisms of Schemes 5–6 have been examined by numerical simulations of the differential equations of the reaction. Both simulations and fitting to observed kinetics data were carried out with the SCIENTIST 2.0 software package (Micromath, Inc.). Determination of apparent half-times (FIG. 6B) from kinetic data fit to two-exponential functions (FIG. 6A) was carried out with the "solve" function of MathCAD 4.0 software (MathSoft, Inc.).

Results

Comparison of Glycation by Glucose and Ribose

The reaction of RNase A with ribose and glucose has been followed primarily with ELISA assays, using R479 rabbit AGE-specific antibodies developed against glucose-modified BSA. To a lesser extent, the production of pentosidine, the only known acid-stable fluorescent AGE, was quantiated by HPLC following acid hydrolysis. Preliminary studies using 0.05 M ribose at 37° C. showed that the rate of antigenic AGE formation appears to be modestly increased (roughly 2–3 fold as measured by the apparent half-time) as the pH is increased from 5.0 to 7.5, with an apparent small induction period at the beginning of the kinetics in all cases. The glycation of RNase with 0.05 M ribose at pH 7.5 (half-time near 6.5 days) appears to be almost an order of magnitude faster than that of glycation with 1.0 M glucose (half-time in excess of 30 days; see FIG. 7B, solid line). The latter kinetics also displayed a small induction period but incomplete leveling off even after 60 days, making it difficult to estimate a true half-time.

When the dependence of the kinetics on ribose concentration was examined at pH 7.5, a most unexpected result was obtained. The rate of reaction initially increased with increasing ribose concentration, but at concentrations above 0.15 M the rate of reaction leveled off and then significantly decreased (FIG. 6A). A plot of the dependence of the reciprocal half-time on the concentration of ribose (FIG. 6B) shows that high ribose concentrations are paradoxically inhibitory to post-Amadori antigenic AGE formation. This unusual but consistent effect was found to be independent of changes in the concentration of either buffer (2-fold) or RNase (10-fold), and it was not changed by affinity purification of the R479 antibody on a column of immobilized AGE-RNase. It is also not due to effects of ribose on the ELISA assay itself. The measured inhibitory effect by ribose on post-Amadori AGE formation is not likely due to ribose interference with antibody recognition of the AGE antigenic sites on protein in the ELISA assay. Prior to the first contact with the primary anti-AGE antibody on the ELISA plates, glycated protein has been diluted over 1000-fold, washed extensively with Tween-20 after adsorption, and blocked with a 1% casein coating followed by further washing with Tween-20.

Kinetics of Formation of Post-Amadori Antigenic AGEs by "Interrupted Glycation"

In view of the small induction period seen, an attempt was made to determine whether there was some accumulation during the reaction, of an early precursor such as an Amadori intermediate, capable of producing the ELISA-detectable post-Amadori antigenic AGEs. RNase was glycated at pH 7.5 and 37° C. with a high ribose concentration of 0.5 M, and the reaction was interrupted after 24 h by immediate cooling to 4° C. and dialysis against several changes of cold buffer over a period of 24 h to remove free and reversibly bound (Schiff base) -ribose. Such a ribose-free sample was then rapidly warmed to 37° C. without re-adding any ribose, and was sampled for post-Amadori AGE formation over several days. The AGE antigen production of this 24 h "interrupted glycation" sample is shown by the dashed line and open triangles in FIG. 7A, the time spent in the cold dialysis is not included. An uninterrupted control (solid line and filled circles) is also shown for comparison. Dramatically different kinetics of post-Amadori antigenic. AGE formation are evident in the two samples. The kinetics of AGE antigen production of the ribose-free interrupted sample now show (1) monoexponential kinetics with no induction period, (2) a greatly enhanced rate of antigenic AGE formation, with remarkable half-times of the order of 10 h, and (3) production of levels of antigen comparable to those seen in long incubations in the continued presence of ribose (see FIG. 6A). Equally significant, the data also demonstrate that negligible AGE antigen was formed during the cold dialysis period, as shown by the small difference between the open triangle and filled circle points at time 1 day in FIG. 7A. Very little, if any, AGE was formed by the "interruption"

procedure itself. These observations show that a fully competent isolatable intermediate or precursor to antigenic AGE has been generated during the 24 h contact with ribose prior to the removal of the free and reversibly bound sugar.

Samples interrupted after only 8 h produced a final amount of AGE antigen that was about 72% of the 24 h interrupted sample. Samples of RNase glycated with only 0.05 M ribose and interrupted at 8 h by cold dialysis and reincubation at 37° C. revealed less than 5% production of ELISA-reactive antigen after 9 days. Interruption at 24 h, however, produced a rapid rise of ELISA antigen (similar to FIG. 7A) to a level roughly 50% of that produced in the uninterrupted presence of 0.05 M ribose.

The same general interruption effects were also seen with other proteins (BSA and Hemoglobin). Except for a somewhat different absolute value of the rate constants, and the amount of antigenic AGEs formed during the 24 h 0.5 M ribose incubation, the same dramatic increase in the rate of AGE antigen formation was observed after removal of 0.5 M ribose.

Figure 7B:
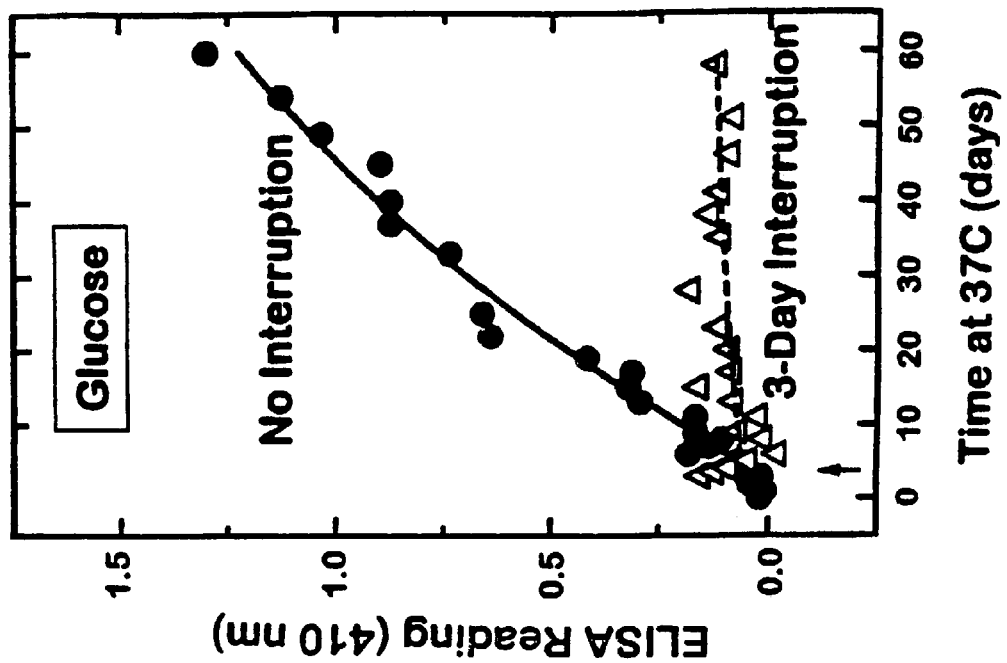
FIG. 7 are two graphs showing a comparison of uninterrupted and interrupted glycation of RNase by glucose (7B) and ribose (7A), as detected by ELISA.
Figure 7A:
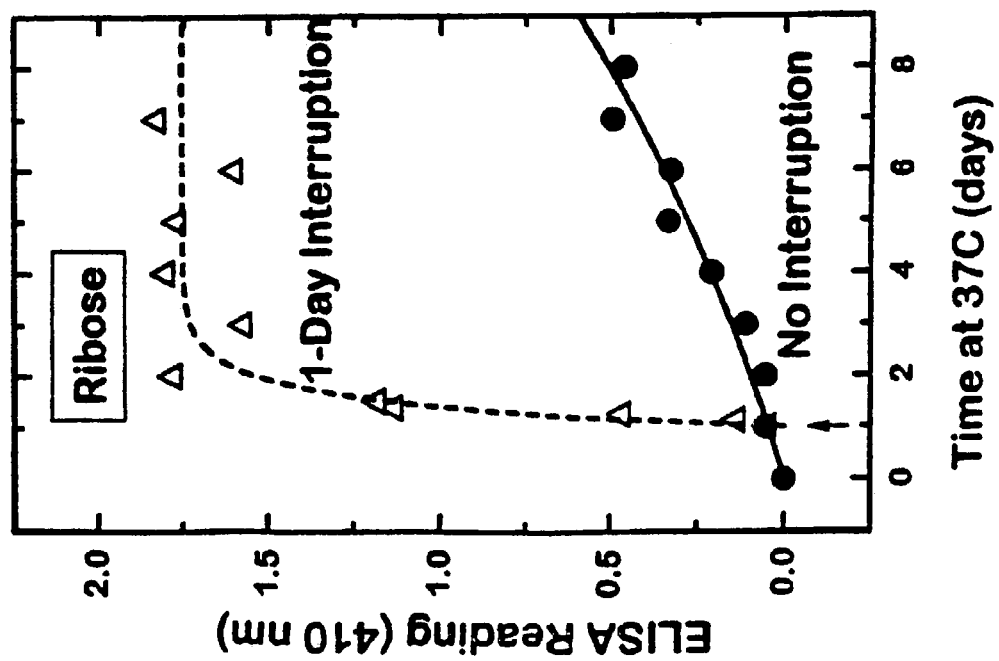

Glycation is much slower with glucose than with ribose (note the difference in time scales between FIG. 7A and FIG. 7B). However, unlike the case with ribose, interruption after 3 days of glycation by 1.0 M glucose produced negligible buildup of precursor to ELISA-reactive AGE antigens (FIG. 7B, dashed curve).

Kinetics of Pentosidine Formation

Figure 8A:
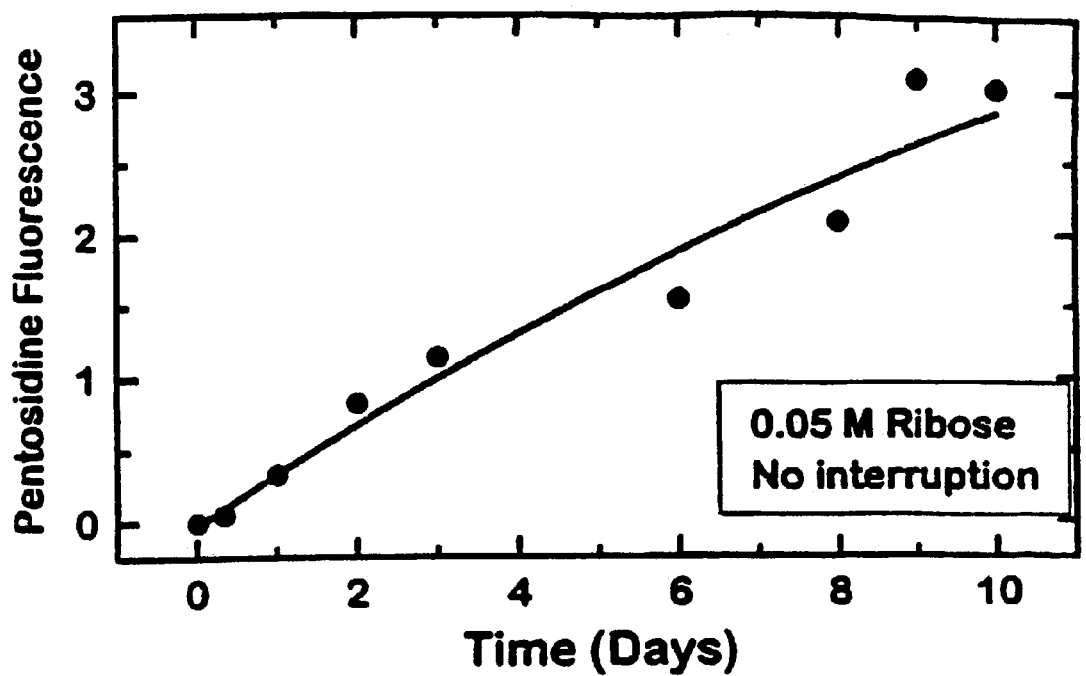
FIG. 8A Uninterrupted glycation in the presence of 0.05 M ribose.
Figure 8B:
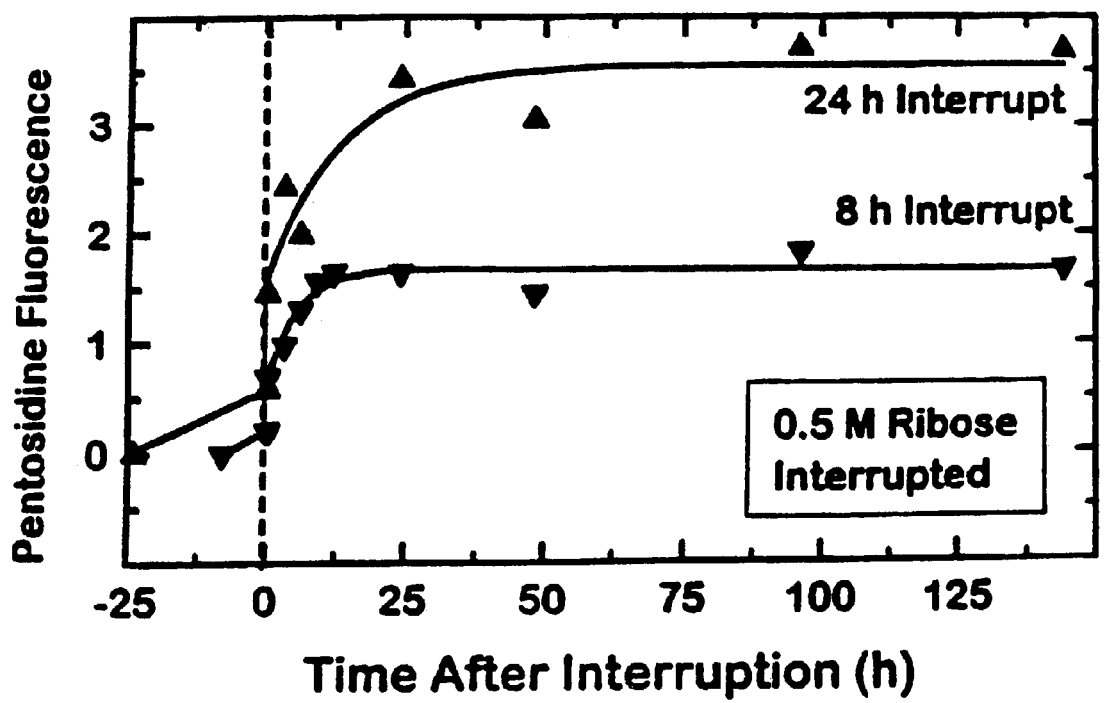
FIG. 8B Interrupted glycation after 8 and 24 hours of incubation.

The samples subjected to ELISA testing were also assayed for the production of pentosidine, an acid-stable AGE. The content of pentosidine was measured for the same RNase samples analyzed for antibody reactivity by ELISA. Glycation by ribose in 0.4 M phosphate buffer at pH 7.5 produced pentosidine in RNase A that was quantitated by fluroescence after acid hydrolysis. FIG. 8A shows that under uninterrupted conditions, 0.05 M ribose produces a progressive increase in pentosidine. However, when glycation is carried out under "interrupted" conditions using 0.5 M ribose, a dramatic increase in the rate of pentosidine formation is seen immediately after removal of excess ribose (FIG. 8B), which is similar to, but slightly more rapid than, the kinetics of the appearance of antigenic AGEs (FIG. 7A). A greater amount of pentosidine was also produced with 24 h interruption as compared with 8 h. Reproducible differences between the kinetics of formation of pentosidine and antigenic AGEs can also be noted. A significant amount of pentosidine is formed during the 24 h incubation and also during the cold dialysis, resulting in a jump of the dashed vertical line in FIG. 8B. Our observations thus demonstrate that a pentosidine precursor accumulates during ribose glycation that can rapidly produce pentosidine after ribose removal (cf. Odetti et al., 1992, *Diabetes* 41:153–159).

Rate of Buildup of the Reactive Intermediate(s)

The "interrupted glycation" experiments described above demonstrate that a precursor or precursors to both post-Amadori antigenic AGEs and pentosidine can be accumulated during glycation with ribose. The kinetics of formation of this intermediate can be independently followed and quantitated by a variation of the experiments described above. The amount of intermediate generated in RNase at different contact times with ribose can be assayed by the maximal extent to which it can produce antigenic AGE after interruption. At variable times after initiating glycation, the free and reversibly-bound ribose is removed by dialysis in the cold or by rapid dilution (see below). Sufficient time (5 days, which represents several half-lives according to FIG. 7A) is then allowed after warming to 37° C. for maximal development of post-Amadori antigenic AGEs. The ELISA readings 5 days after each interruption point, representing maximal AGE development, would then be proportional to the intermediate concentration present at the time of interruption.

Figure 9:
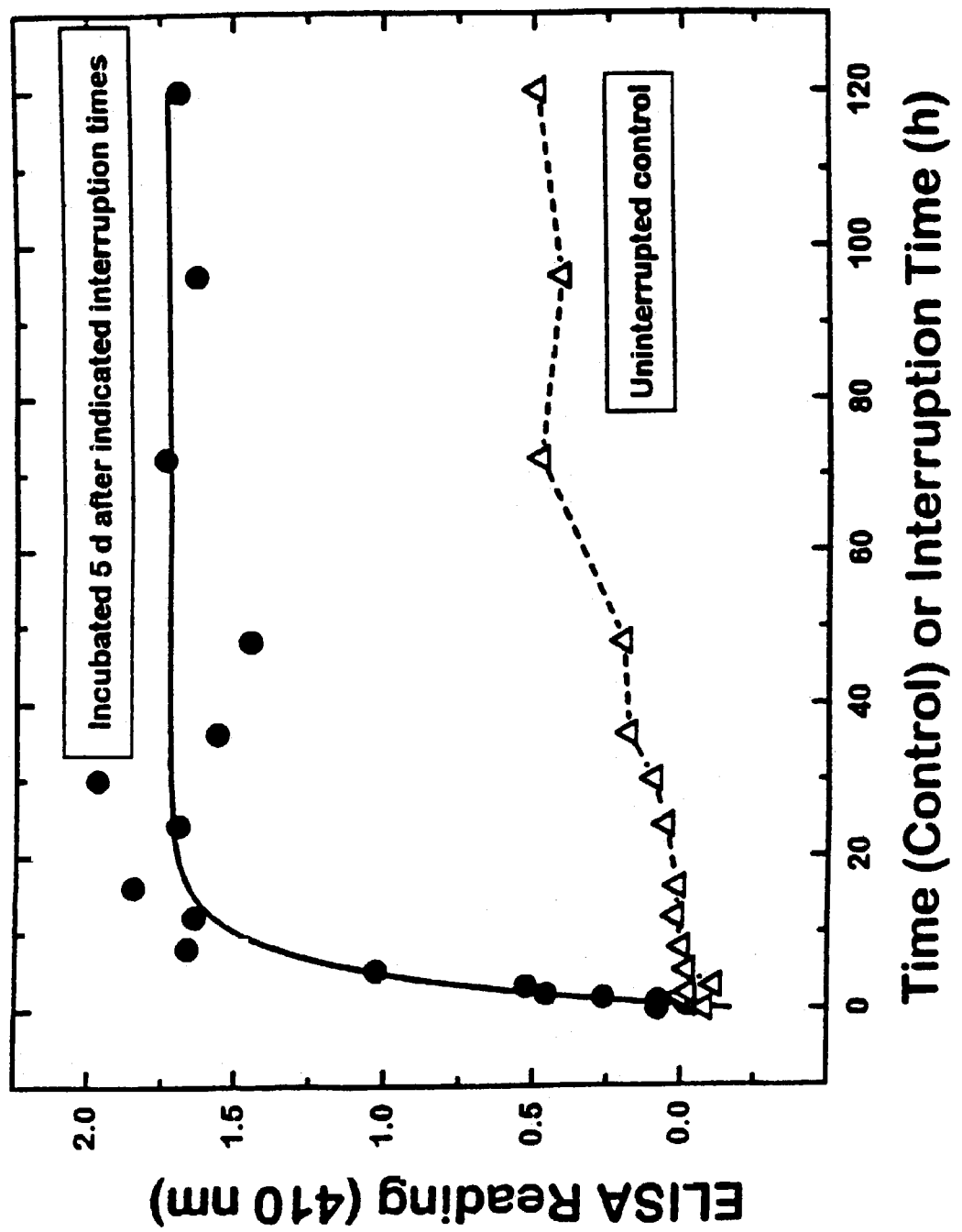
FIG. 9 is a graph which shows the kinetics of reactive intermediate buildup.

FIG. 9 shows such an experiment where the kinetics of intermediate buildup are measured for RNase A in the presence of 0.5 M ribose (solid symbols and curve). For comparison, the amount of AGE present before ribose removal at each interruption point is also shown (open symbols and dashed lines). As expected (cf. FIG. 7A), little AGE is formed prior to removal (or dilution) of ribose, so that ELISA readings after the 5 day secondary incubation periods are mostly a measure of AGE formed after ribose removal. The results in FIG. 9 show that the rate of buildup of intermediate in 0.5 M ribose is exponential and very fast, with a half-time of about 3.3 h. This is about 3-fold more rapid than the observed rate of conversion of the intermediate to antigenic AGEs after interruption (open symbols and dashed curve FIG. 7A).

In these experiments the removal of ribose at each interruption time was achieved by 100-fold dilution, and not by dialysis. Simple dilution reduced the concentration of ribose from 0.05 M to 0.005 M. It was independently determined (FIG. 6A) that little AGE is produced in this time scale with the residual 5 mM ribose. This dilution approach was primarily dictated by the need for quantitative point-to-point accuracy. Such accuracy would not have been achieved by the dialysis procedure that would be carried out independently for each sample at each interruption point. Our results show that dilution was equivalent to dialysis.

A separate control experiment (see FIG. 10 below) demonstrated that the instantaneous 100-fold dilution gave nearly identical results to the dialysis procedure. These control experiments demonstrate that the reversible ribose-protein binding (Schiff base) equilibrium is quite rapid on this time scale. This is consistent with data of Bunn and Higgins (1981, *Science* 213: 222–224) that indicated that the half-time of Schiff base formation with 0.5 M ribose should be on the order of a few minutes. The 100-fold rapid dilution method to reduce ribose is a valid method where quantitative accuracy is essential and cannot be achieved by multiple dialysis of many samples.

Figure 10A:
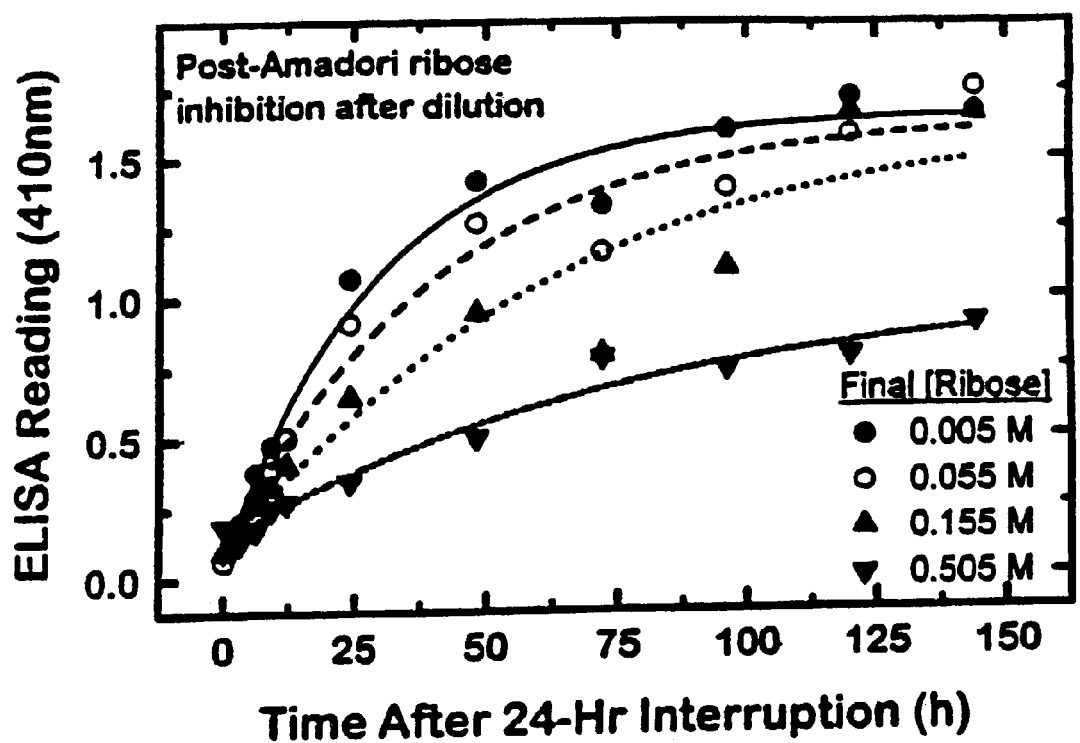
FIG. 10A graphs data where aliquots were diluted into inhibitor containing buffers at time 0.
Figure 10B:
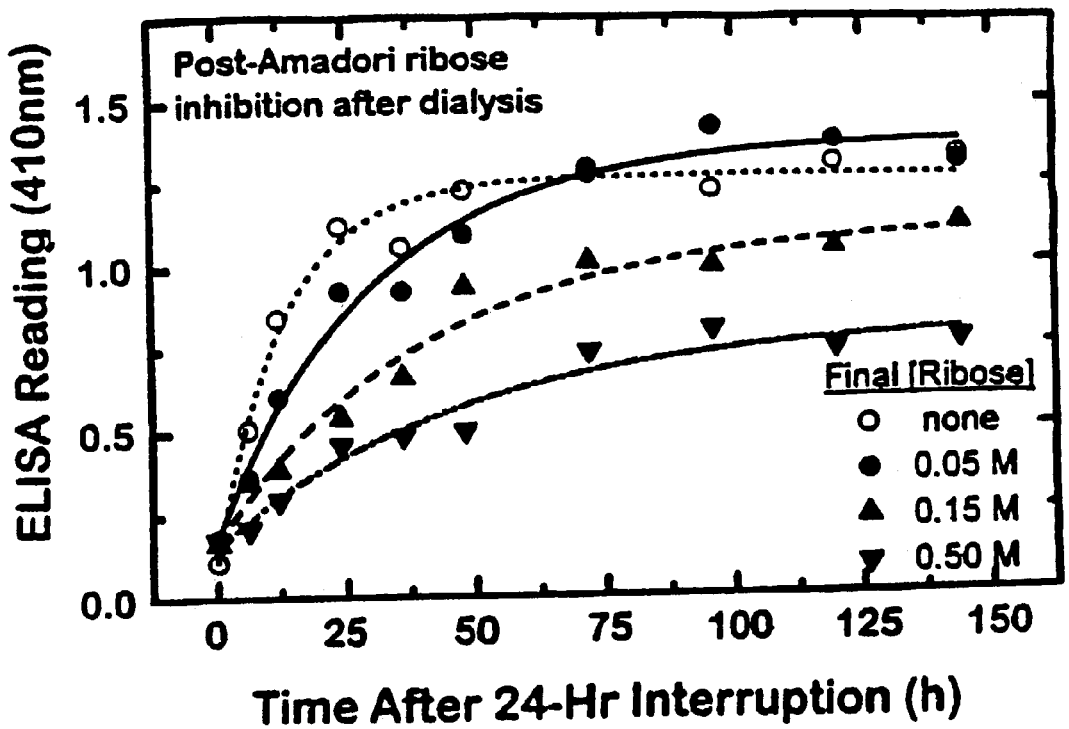
FIG. 10B graphs data where samples were interrupted at 24 h, and then diluted into inhibitor containing buffers.

Direct Inhibition of Post-Amadori AGE Formation from the Intermediate by Ribose and Glucose The increase in the rate of AGE formation after interruption and sugar dilution suggests but does not prove, that high concentrations of ribose are inhibiting the reaction at or beyond the first "stable" intermediate, presumably the Amadori derivative (boxed in Scheme I). A test of this was then carried out by studying the effect of directly adding ribose, on the post-Amadori reaction. RNase was first incubated for 24 h in 0.5 M ribose in order to prepare the intermediate. Two protocols were then carried out to measure possible inhibition of the post-Amadori formation of antigenic AGEs by different concentrations of ribose. In the first experiment, the 24 h ribated sample was simply diluted 100-fold into solutions containing varying final concentrations of ribose ranging from 0.005 M to 0.505 M (FIG. 10A). The rate and extent of AGE formation are clearly seen to be diminished by increasing ribose concentrations. Significantly, up to the highest concentration of 0.5 M ribose, the kinetics appear exponential and do not show the induction period that occurs with uninterrupted glycation (FIGS. 6A and 7A) in high ribose concentrations.

A second experiment (FIG. 10B) was also conducted in which the 24 h interrupted sample was extensively dialyzed in the cold to release free and reversibly bound ribose as well as any inhibitory products that may have formed during the 24 h incubation with ribose. Following this, aliquots were diluted 100-fold into varying concentrations of freshly made ribose, and the formation of antigenic AGE products was monitored as above. There results were nearly identical to the experiment of FIG. 10A where the dialysis step was omitted. In both cases, the rate and extent of AGE formation were diminished by increasing concentrations of ribose, and the kinetics appeared exponential with no induction period.

The question of whether glucose or other sugars can also inhibit the formation of AGEs from the reactive intermediate obtained by interrupted glycation in 0.5 M ribose was also investigated. The effects of glucose at concentrations of 1.0–2.0 M were tested (data not shown). Glucose was clearly not as inhibitory as ribose. When the 24 h ribose interrupted sample was diluted 100-fold into these glucose solutions, the amount of antigenic AGE formed was diminished by about 30%, but there was little decrease in the apparent rate constant. Again, the kinetics appeared exponential.

Effect of pH on Post-Amadori Kinetics of AGE Formation

Figure 11:
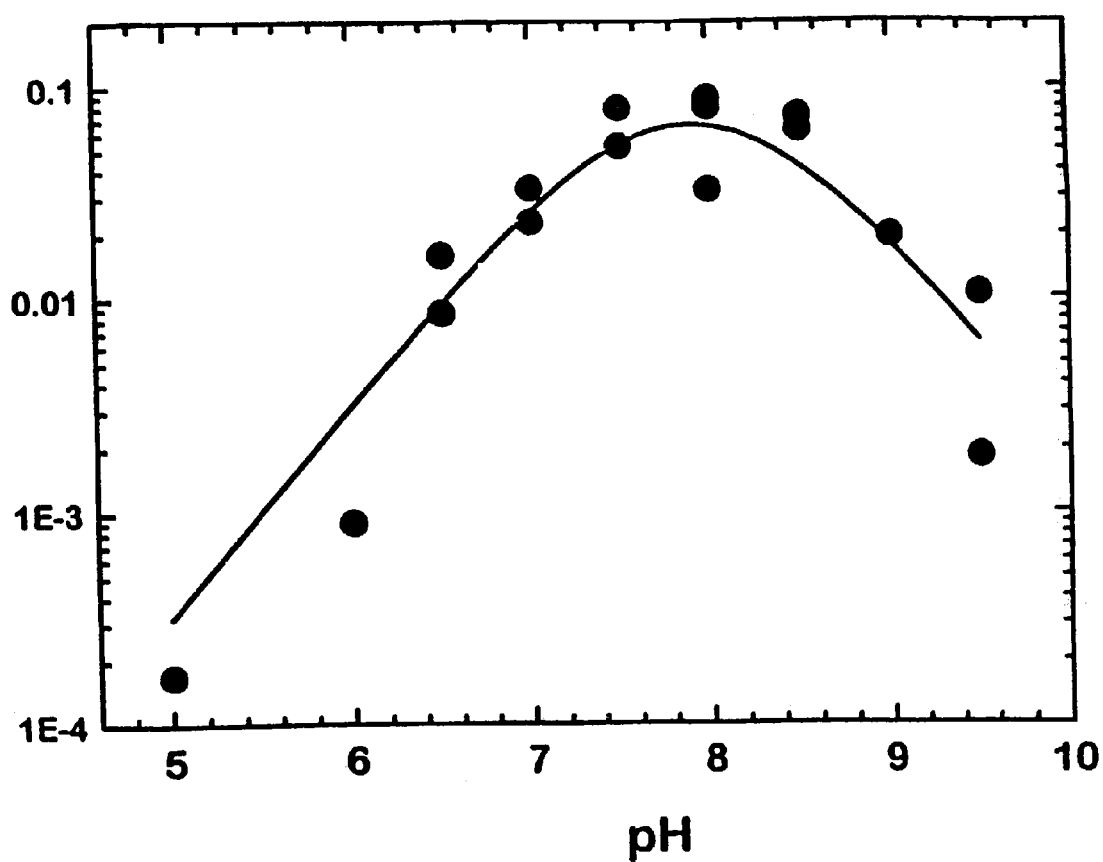
FIG. 11 is a graph showing dependence of the initial rate of formation of antigenic AGE on pH following interruption of glycation.

The interrupted glycation method was used to investigate the pH dependence of the post-Amadori kinetics of AGE formation from the reactive intermediate. In these experiments, RNase A was first reacted for 24 h with 0.5 M ribose at pH 7.5 to generate the reactive intermediate. The kinetics of the decay of the intermediate to AGEs were then measured by ELISA. FIG. 11 shows that an extremely wide pH range of 5.0–9.5 was achievable when the kinetics were measured by initial rates. A remarkable bell-shaped dependence was observed, showing that the kinetics of antigenic AGEs formation are decreased at both acidic and alkaline pH ranges, with an optimum near pH 8.

Figure 12A:
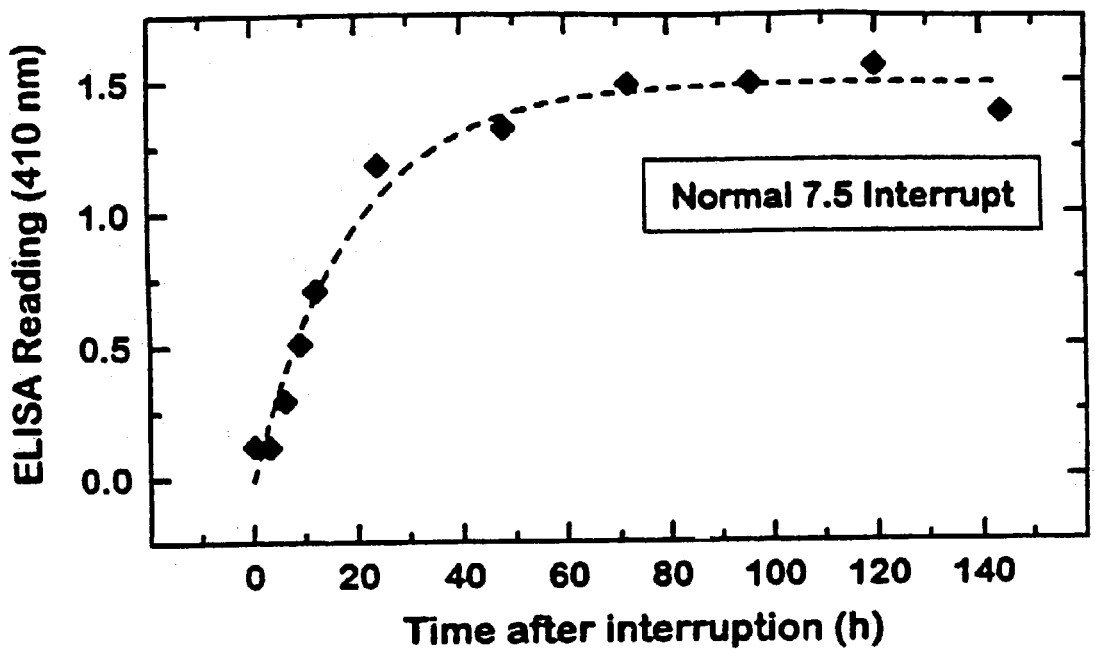
FIG. 12 are two graphs showing the effect of pH jump on ELISA detected AGE formation after interrupted glycation. Interrupted samples left 12 days at 37° C. in pH 5.0 buffer produced substantial AGEs (33%.
FIG. 12B) when pH was changed to 7.5, as compared to the normal control sample not exposed to low pH (FIG. 12A).
Figure 12B:
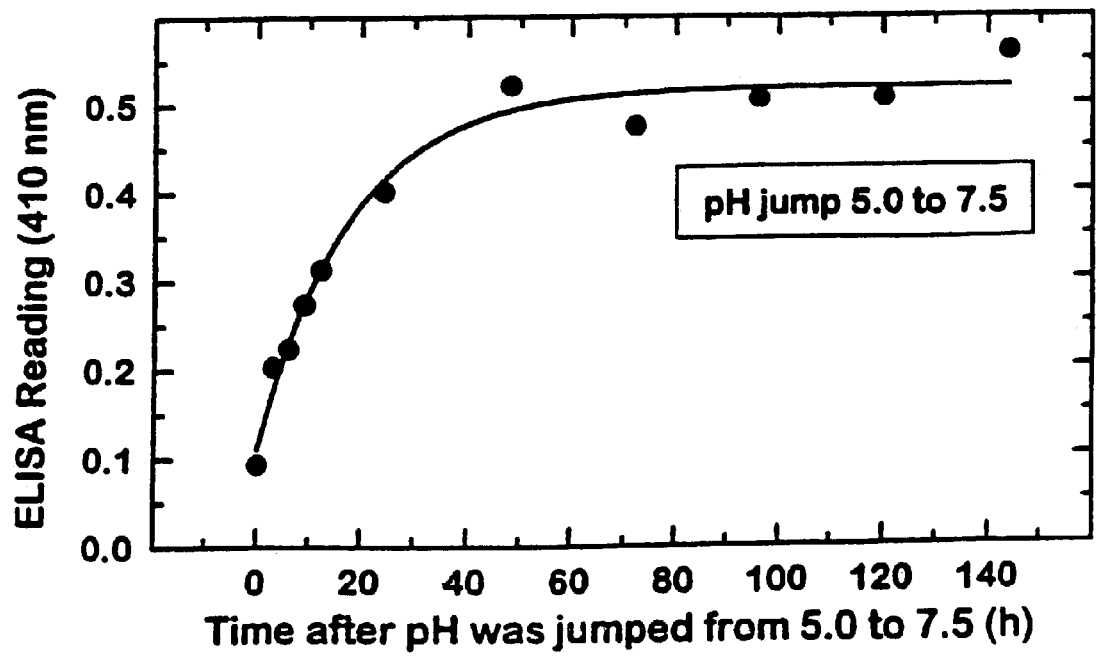

A single "pH jump" experiment was also carried out on the pH 5.0 sample studied above which had the slowest rate of antigenic AGE formation. After 12 days at 37° C. in pH 5.0 buffer, the pH was adjusted quickly to 7.5, and antigenic AGE formation was monitored by ELISA. Within experimental error, the sample showed identical kinetics (same first order rate constant) of AGE formation to interrupted glycation samples that had been studied directly at pH 7.5 (FIG. 12). In this experiment, the relative amounts of antigenic AGE could not be directly compared on the same ELISA plate, but the pH-jumped sample appeared to have formed substantial though somehow diminished levels of antigenic AGEs. These results demonstrate that intermediate can be prepared free of AGE and stored at pH 5 for later studies of conversion to AGEs.

Inhibition of Post-Amadori AGE Formation by Aminoguanidine

Figure 20A:
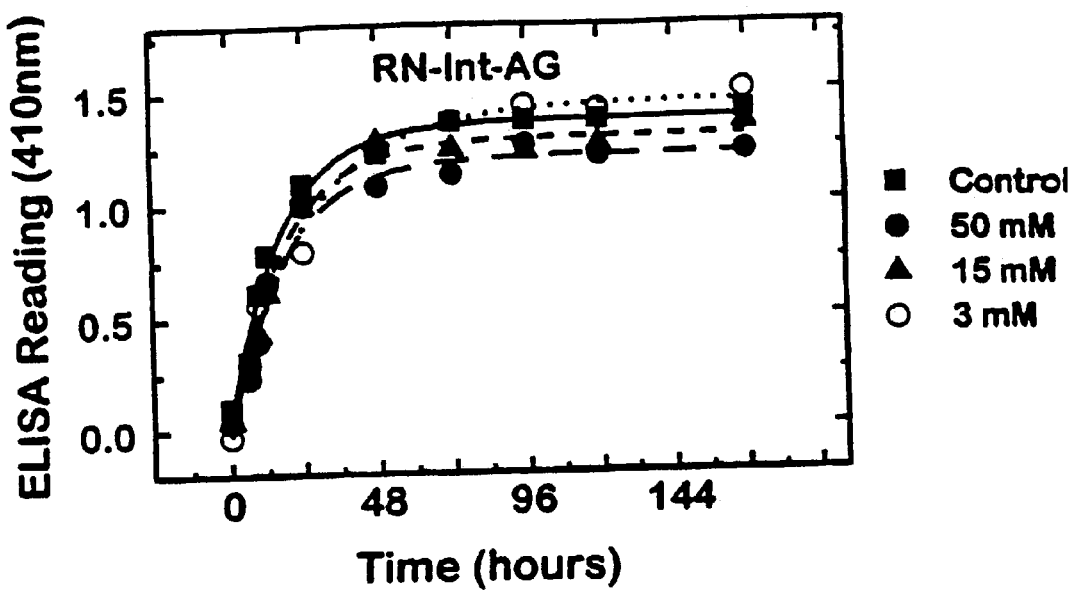
FIG. 20A RNase, FIG. 20B BSA.
Figure 20B:
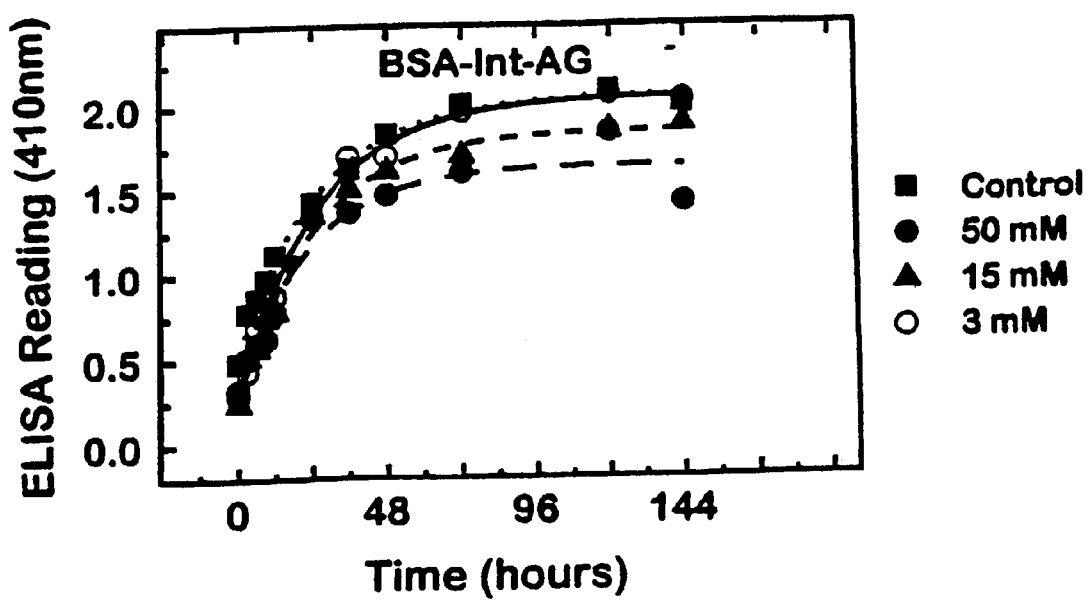
FIG. 20 are graphs depicting the effect of aminoguanidine on post-Amadori AGE formation after interrupted glycation by ribose.

The efficacy of aminoguanidine was tested by this interrupted glycation method, i.e., by testing its effect on post-Amadori formation of antigenic AGEs after removal of excess and reversibly bound ribose. FIG. 20A demonstrates that aminoguanidine has modest effects on blocking the formation of antigenic AGEs in RNase under these conditions, with little inhibition below 50 mM. Approximately 50% inhibition is achieved only at or above 100–250 mM. Note again that in these experiments, the protein was exposed to aminoguanidine only after interruption and removal of free and reversibly bound ribose. Comparable results were also obtained with the interrupted glycation of BSA (FIG. 20B).

Amino Acid analysis of Interrupted Glycation Samples

Amino acid analysis was carried out on RNase after 24 h contact with 0.5 M ribose (undialyzed), after extensive dialysis of the 24 h glycated sample, and after 5 days of incubation of the latter sample at 37° C. These determinations were made after sodium cyanoborohydride reduction, which reduces Schiff base present on lysines or the terminal amino group. All three samples, normalized to alanine (12 residues), showed the same residual lysine content (4.0±0.5 out of the original 10 in RNase). This indicates that after 24 h contact with 0.5 M ribose, most of the formed Schiff base adducts had been converted to Amadori or subsequent products. No arginine or histidine residues were lost by modification.

Discussion

The use of rapidly reacting ribose and the discovery of its reversible inhibition of post-Amadori steps have permitted the dissection and determination of the kinetics of different steps of protein glycation in RNase. Most previous kinetic studies of protein "glycation" have actually been restricted to the "early" steps of Schiff base formation and subsequent Amadori rearrangement. Some kinetic studies have been carried out starting with synthesized fructosylamines, i.e. small model Amadori compounds of glucose (Smith and Thornalley, 1992, *Eur. J. Biochem.* 210:729–739, and references cited therein), but such studies, with few exceptions, have hitherto not been possible with proteins. One notable exception is the demonstration by Monnier (Odetti et al., 1992, supra) that BSA partially glycated with ribose can rapidly produce pentosidine after ribose removal. The greater reactivity of ribose has also proven a distinct advantage in quantitatively defining the time course of AGE formation. It is noted that glucose and ribose are both capable of producing similar AGE products, such as pentosidine (Grandhee & Monnier, 1991, supra; Dyer et al. 1991, supra), and some $^{13}C$ NMR model compound work has been done with ADP-ribose (Cervantes-Laurean et al., 1993, *Biochemistry* 32:1528–1534). The present work shows that antigenic AGE products of ribose fully cross-react with anti-AGE antibodies directed against glucose-modified proteins, suggesting that ribose and glucose produce similar antigenic AGEs. The primary kinetic differences observed between these two sugars are probably due to relative differences in the rate constants of steps leading to post-Amadori AGE formation, rather than in the mechanism.

The results presented reveal a marked and paradoxical inhibition of overall AGE formation by high concentrations of ribose (FIG. 6) that has not been anticipated by earlier studies. This inhibition is rapidly reversible in the sense that it is removed by dialysis of initially modified protein (FIG. 7A) or by simple 100-fold dilution (as used in FIG. 11). The experiments of FIG. 10 demonstrate that it is not due to the accumulation of dialyzable inhibitory intermediates during the initial glycation, since dialysis of 24 h modified protein followed by addition of different concentrations of fresh ribose induces the same inhibition. The data of FIGS. 10A,B show that the inhibition occurs by reversible and rapid interaction of ribose with protein intermediate containing reactive Amadori products. The inhibition is unlikely to apply to the early step of formation of Amadori product due to the rapid rate of formation of the presumed Amadori intermediate that was determined in the experiment of FIG. 9. The identification of the reactive intermediate as an Amadori product is well supported by the amino acid analysis carried out (after sodium cyanoborohydrate reduction) before and after dialysis at the 24 h interruption point.

The unchanged residual lysine content indicates that any dischargeable Schiff bases have already been irreversibly converted (presumably by Amadori rearrangement) by the 24 h time.

The secondary ribose suppression of "late" but not "early" glycation steps significantly enhances the accumulation of a fully-competent reactive Amadori intermediate containing little AGE. Its isolation by the interruption procedure is of importance for kinetic and structural studies, since it allows one to make studies in the absence of free or Schiff base bound sugar and their attendant reactions and complications. For example, the post-Amadori conversion rates to antigenic AGE and pentosidine AGE products have been measured (FIG. 7A, open symbols, and FIG. 8B), and demonstrated to be much faster (t ½~10 h) than reflected in the overall kinetics under uninterrupted conditions (FIG. 6A and FIG. 8A). The rapid formation of pentosidine that was measured appears consistent with an earlier interrupted ribose experiment on BSA by Odetti et al. (1992, supra). Since ribose and derivatives such as ADP-ribose are normal metabolites, the very high rates of AGE formation seen here suggest that they should be considered more seriously as sources of potential glycation in various cellular compartments (Cervantes-Laurean et al., 1993, supra), even though their concentrations are well below those of the less reactive glucose.

Another new application of the isolation of intermediate is in studying the pH dependence of this complex reaction. The unusual bell-shaped pH profile seen for the post-Amadori AGE formation (FIG. 11) is in striking contrast to the mild pH dependence of the overall reaction. The latter kinetics reflect a composite effect of pH on all steps in the reaction, including Schiff base and Amadori product formation, each of which may have a unique pH dependence. This complexity is especially well illustrated by studies of hemoglobin glycation (Lowery et al., 1985, *J. Biol. Chem.* 260: 11611–11618). The bell-shaped pH profile suggests, but does not prove, the involvement of two ionizing groups. If true, the data may imply the participation of a second amino group, such as from a neighboring lysine, in the formation of dominant antigenic AGEs. The observed pH profile and the pH jump observations described suggest that a useful route to isolating and maintaining the reactive intermediate would be by the rapid lowering of the pH to near 5.0 after 24 h interruption.

The kinetic studies provide new insights into the mechanisms of action of aminoguanidine (guanylhydrazine), an AGE inhibitor proposed by Cerami and co-workers to combine with Amadori intermediates (Brownlee et al., 1986, supra). This proposed pharmacological agent is now in Phase III clinical trials for possible therapeutic effects in treating diabetes (Vlassara et al., 1994, supra). However, its mechanism of AGE inhibition is likely to be quite complex, since it is multifunctional. As a nucelophilic hydrazine, it can reversibly add to active carbonyls, including aldehydo carbonyls of open-chain glucose and ribose (Khatami et al., 1988, *Life Sci.* 43:1725–1731; Hirsch et al., 1995, *Carbohyd. Res.* 267:17–25), as well as keto carbonyls of Amadori compounds. It is also a guanidinium compound that can scavange highly reactive dicarbonyl glycation intermediates such as glyoxal and glucosones (Chen & Cerami, 1993, *J. Carbohyd. Chem.* 12:731–742; Hirsch et al., 1992, *Carbohyd. Res.* 232:125–130; Ou & Wolff, 1993, *Biochem. Pharmacol.* 46:1139–1144). The interrupted glycation method allowed examination of aminoguanidine efficacy on only post-Amadori steps of AGE formation. Equally important, it allowed studies in the absence of free sugar or dicarbonyl-reactive fragments from free sugar (Wolff & Dean, 1987, *Biochem. J.* 245:243–250; Wells-Knecht et al., 1995, *Biochemistry* 34:3702–3709) that can combine with aminoguanidine. The results of FIG. 20 demonstrate that aminoguanidine has, at best, only a modest effect on post-Amadori AGE formation reactions, achieving 50% inhibition at concentrations above 100–250 mM. The efficacy of aminoguanidine thus predominantly arises either from inhibiting early steps of glycation (Schiff base formation) or from scavenging highly reactive dicarbonyls generated during glycation. Contrary to the original claims, it does not appear to inhibit AGE formation by complexing the Amadori intermediate.

The use of interrupted glycation is not limited for kinetic studies. Interrupted glycation can simplify structural studies of glycated proteins and identifying unknown AGEs using techniques such as $^{13}C$ NMR that has been used to detect Amadori adducts of RNase (Neglia et al., 1983, *J. Biol. Chem.* 258:14279–14283; 1985, *J. Biol. Chem.* 260:5406–5410). The combined use of structural and kinetic approaches should also be of special interest. For example, although the identity of the dominant antigenic AGEs reacting with the polyclonal antibodies remains uncertain, candidate AGEs, such as the recently proposed (carboxymethyl) lysine (Reddy et al., 1995, *Biochemistry* 34:10872–10878; cf. Makita et al., 1992, *J. Biol. Chem.* 267:5133–5138) should display the same kinetics of formation from the reactive intermediate that we have observed. The availability of the interrupted kinetics approach will also help to determine the importance of the Amadori pathway to the formation of this AGE. Similarly, monitoring of the interrupted glycation reaction by techniques such as $^{13}C$ NMR should identify resonances of other candidate antigenic AGEs as being those displaying similar kinetics of appearance. Table I lists the $^{13}C$ NMR peaks of the Amadori intermediate of RNase prepared by reaction with C-2 enriched ribose. The downfield peak near 205 ppm is probably due to the carbonyl of the Amadori product. In all cases, the ability to remove excess free and Schiff base sugars through interrupted glycation will considerably simplify isolation, identification, and structural characterization.

Table I lists the peaks that were assigned to the Post-Amadori Intermediate due to their invariant or decreasing intensity with time. Peak positions are listed in ppm downfield from TMS.

TABLE I

125 MHz C-13 NMR Resonances of Ribonuclease Amadori Intermediate Prepared by 24 HR Reaction with 99% [2-C13] Ribose

| | |
|---|---|
| 216.5 ppm | 108.5 ppm |
| 211.7 | 105.9 |
| 208 | 103.9 |
| | 103 |
| 172 | 95.8 |
| 165 | |
| 163.9 | 73.65 |
| 162.1 | 70.2 |
| | 69.7 |

Figure 31A:
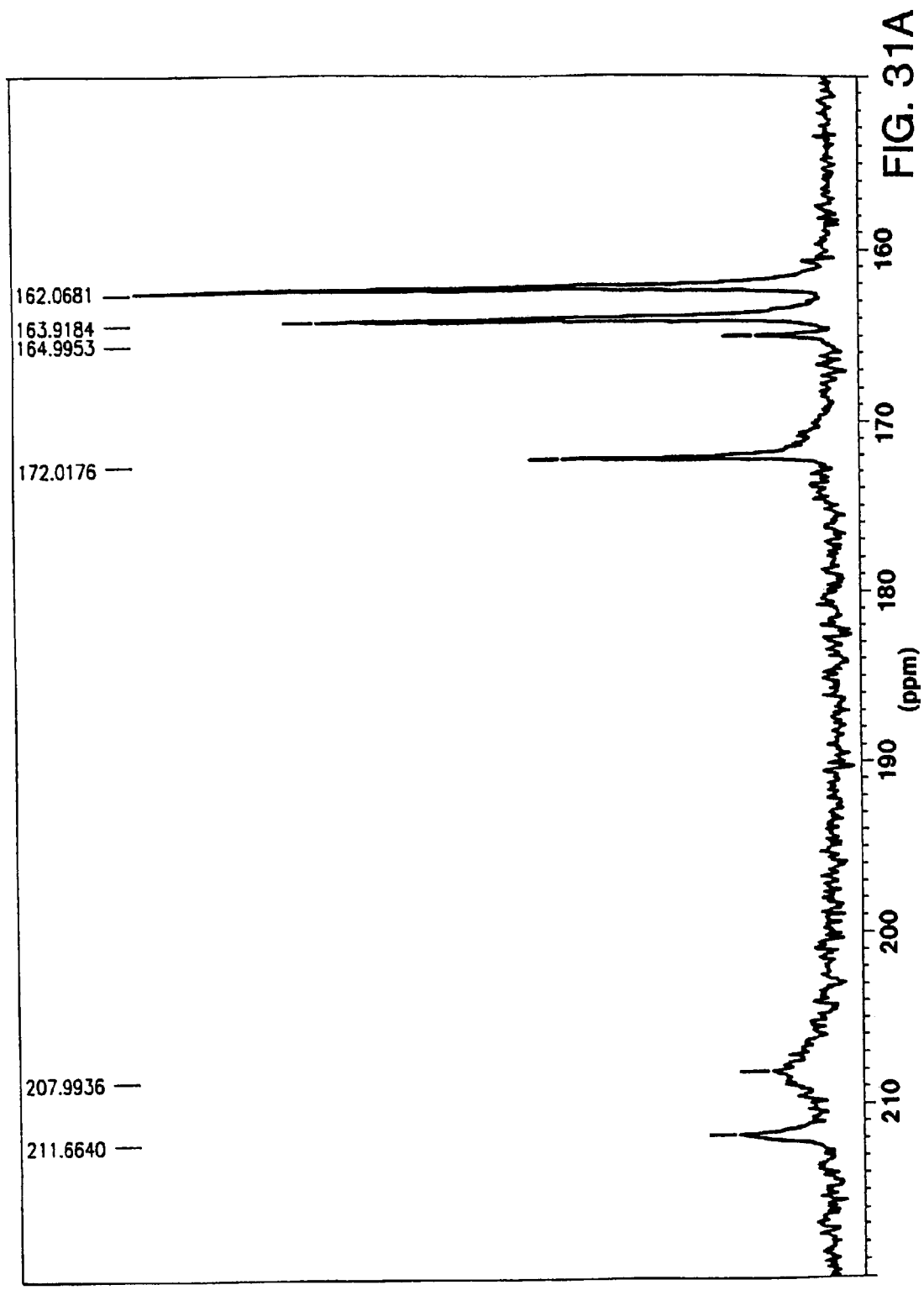
FIG. 31 shows a 125 MHz C-13 NMR Resonance spectrum of Riobonuclease Amadori Intermediate prepared by 24 HR reaction with 99% [2-C13]Ribose.
Figure 31B:
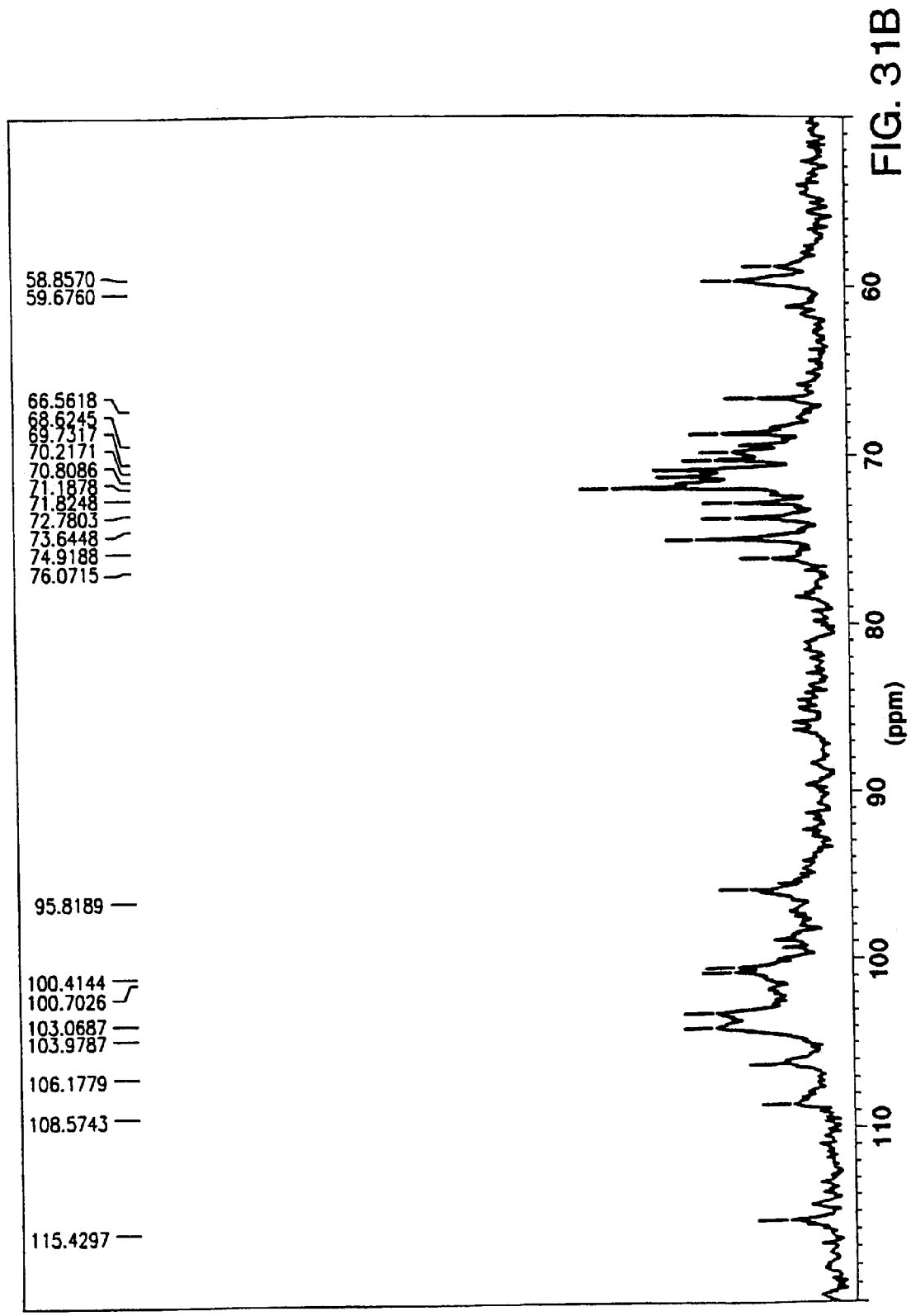
Figure 32A:
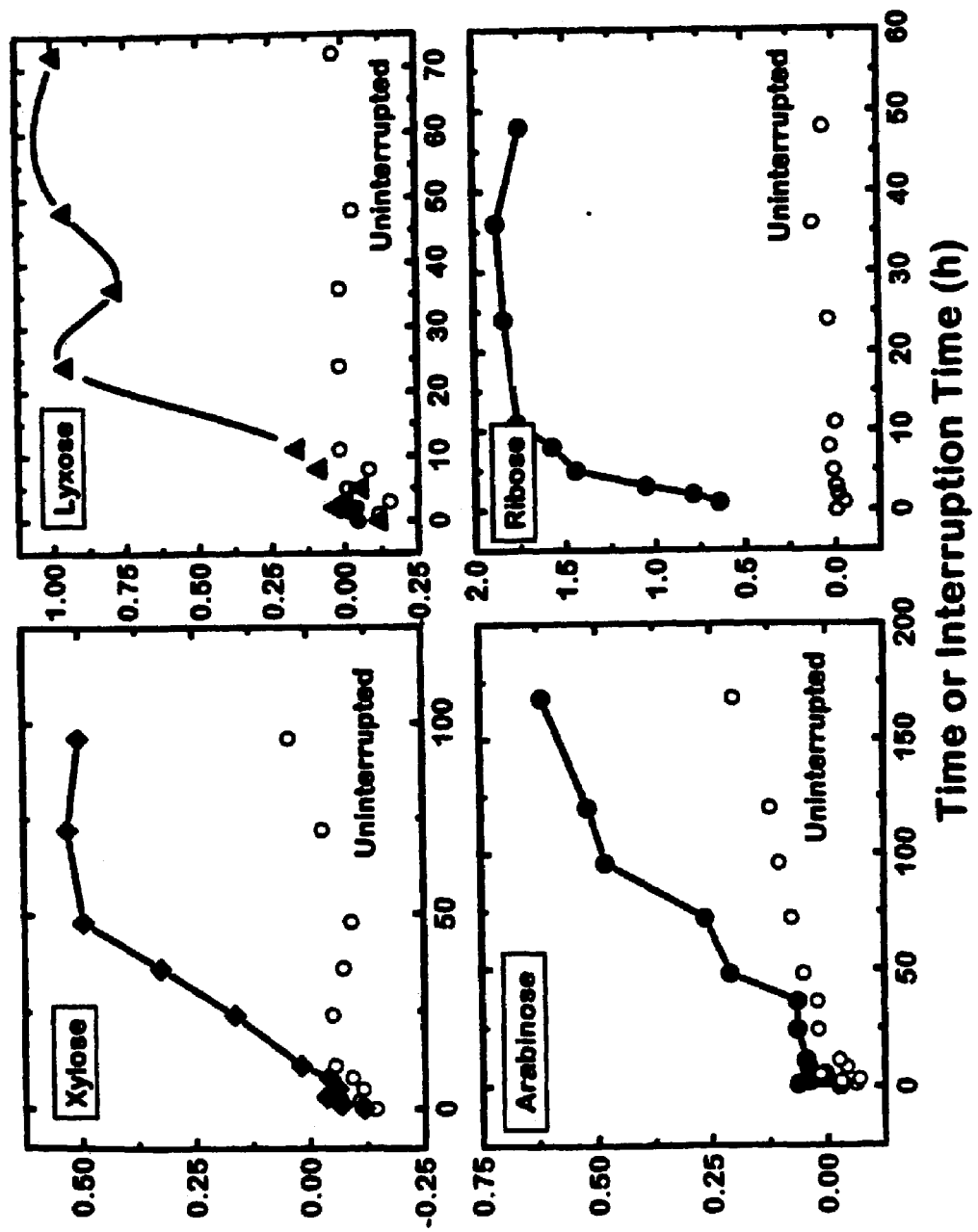
FIG. 32 are graphs which show AGE intermediary formation using the pentoses Xylose, Lyxose, Arabinose and Ribose.
Figure 32B:
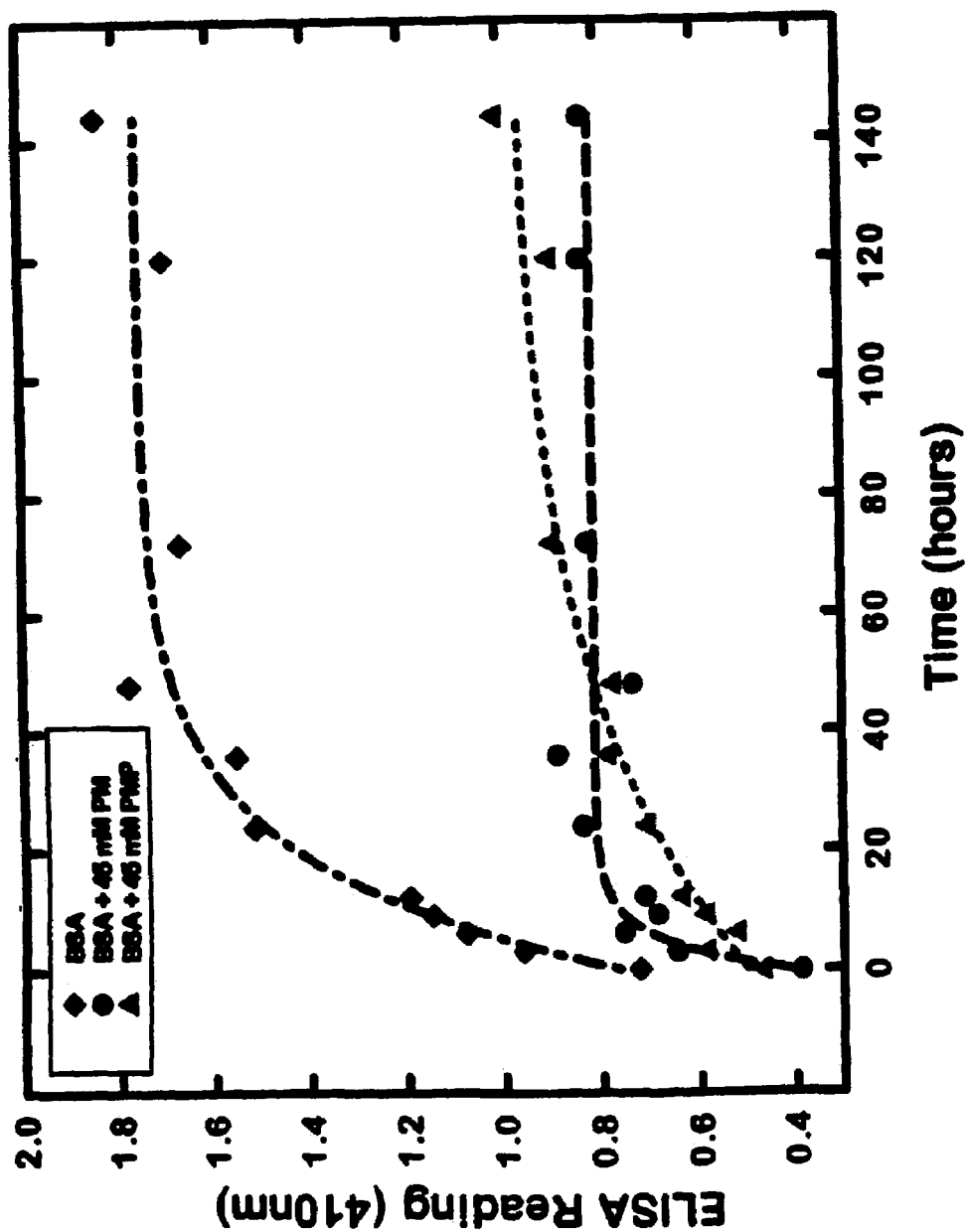

Ribonuclease A was reacted for 24 hr with 0.5 M ribose 99% enriched at C-2, following which excess and Schiff base bound ribose was removed by extensive dialysis in the cold. The sample was then warmed back to 37° C. immediately before taking a 2 hr NMR scan. The signals from RNase reacted with natural abundance ribose under identical conditions were then subtracted from the NMR spectrum. Thus all peaks shown are due to enriched C-13 that originated at the C-2 position. Some of the peaks arise from degradation products of the intermediate, and these can be identified by the increase in the peak intensity over time. FIG. 31 shows the NMR spectrum obtained.

EXAMPLE 3

In Vitro Inhibition of the Formation of Antigenic Advanced Glycation End-Products (AGEs) by Derivatives of Vitamins $B_1$ and $B_6$ and Aminoguanidine. Inhibition of Post-Amadori Kinetics Differs from that of Overall Glycation The interrupted glycation method for following post-Amadori kinetics of AGE formation allows for the rapid quantitative study of "late" stages of the glycation reaction. Importantly, this method allows for inhibition studies that are free of pathways of AGE formation which arise from glycoxidative products of free sugar or Schiff base (Namiki pathway) as illustrated in Scheme I. Thus the interrupted glycation method allows for the rapid and unique identification and characterization of inhibitors of "late" stages of glycation which lead to antigenic AGE formation.

Among the vitamin $B_1$ and $B_6$ derivatives examined, pyridoxamine and thiamine pyrophosphate are unique inhibitors of the post-Amadori pathway of AGE formation. Importantly, it was found that efficacy of inhibition of overall glycation of protein, in the presence of high concentrations of sugar, is not predictive of the ability to inhibit the post-Amadori steps of AGE formation where free sugar is removed. Thus while pyridoxamine, thiamine pyrophosphate and aminoguanidine are potent inhibitors of AGE formation in the overall glycation of protein by glucose, aminoguanidine differs from the other two in that it is not an effective inhibitor of post-Amadori AGE formation. Aminoguanidine markedly slows the initial rate of AGE formation by ribose under uninterrupted conditions, but has no effect on the final levels of antigenic AGEs produced. Examination of different proteins (RNase, BSA and hemoglobin), confirmed that the inhibition results are generally non-specific as to the protein used, even though there are individual variations in the rates of AGE formation and inhibition.

Chemicals and Materials As in Example 1 above.

Preparation of Polyclonal Antibodies to AGEs As in Example 1 above.

ELISA detection of AGE products As in Example 1 above.

Uninterrupted ribose glycation assays Bovine serum albumin, ribonuclease A, and human hemoglobin were incubated with ribose at 37° C. in 0.4 M sodium phosphate buffer of pH 7.5 containing 0.02% sodium azide. The protein (10 mg/ml or 1 mg/ml), .0.05 M ribose, and prospective inhibitors (at 0.5, 3, 15 and 50 mM) were introduced into the incubation mixture simultaneously. Solutions were kept in the dark in capped tubes. Aliquots were taken and immediately frozen until analyzed by ELISA at the conclusion of the reaction. The incubations were for 3 weeks (Hb) or 6 weeks (RNase, BSA). Glycation reactions were monitored for constant pH throughout the duration of the experiments.

Interrupted (Post-Amadori) Ribose Glycation Assays

Glycation was first carried out by incubating protein (10 mg/ml) with 0.5 M ribose at 37° C. in 0.4 M phosphate buffer at pH 7.5 containing 0.2% sodium azide for 24 h in the absence of inhibitors. Glycation was then interrupted to remove excess and reversibly bound (Schiff base) sugar by extensive dialysis against frequent cold buffer changes at 4° C. The glycated intermediate samples containing maximal amount of Amadori product and little AGE (depending on protein) were then quickly warmed to 37° C. without re-addition of ribose. This initiated conversion of Amadori intermediates to AGE products in the absence or presence of various concentrations (typically 3, 15 and 50 mM) of prospective inhibitors. Aliquots were taken and frozen at various intervals for later analysis. The solutions were kept in capped tubes and opened only to remove timed aliquots that were immediately frozen for later carrying out the various analyses.

Numerical Analysis of kinetics data Kinetics data (time progress curves) was routinely fit to mono- or bi-exponential functions using non-linear least squares methods utilizing either SCIENTIST 2.0 (MicroMath, Inc.) or ORIGIN (Microcal, Inc.) software that permit user-defined functions and control of parameters to iterate on. Standard deviations of the parameters of the fitted functions (initial and final ordinate values and rate constants) were returned as measures of the precision of the fits. Apparent half-times for bi-exponential kinetics fits were determined with the "solve" function of MathCad software (MathSoft, Inc.).

Results

Inhibition by Vitamin $B_6$ Derivatives of the Overall Kinetics of AGE Formation from Ribose.

Figure 13A:
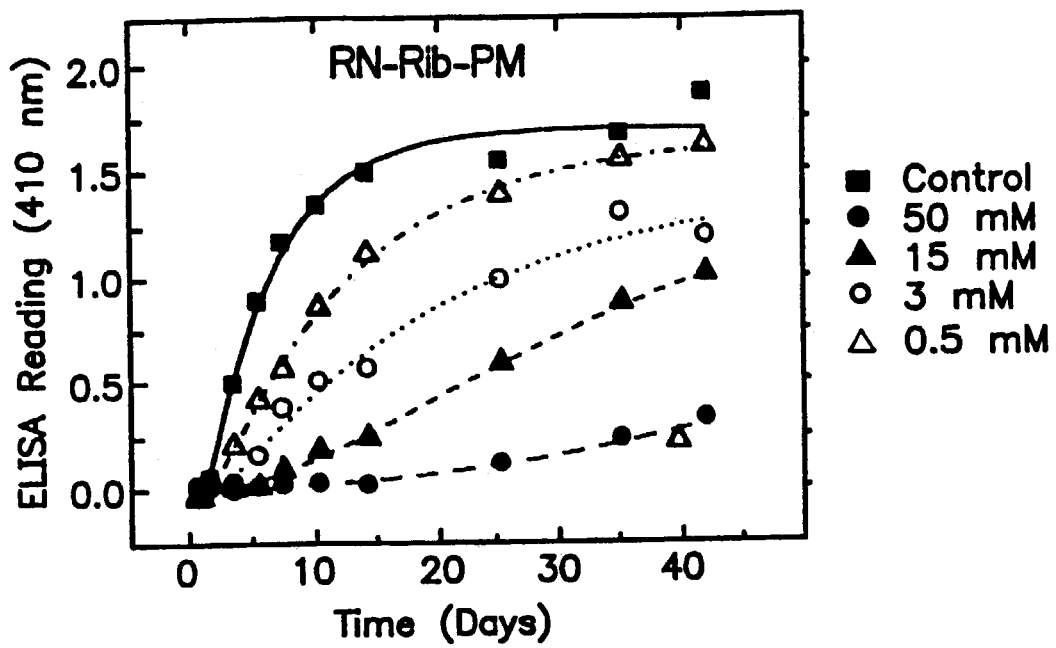
FIG. 13A Pyridoxamine (PM)
Figure 13B:
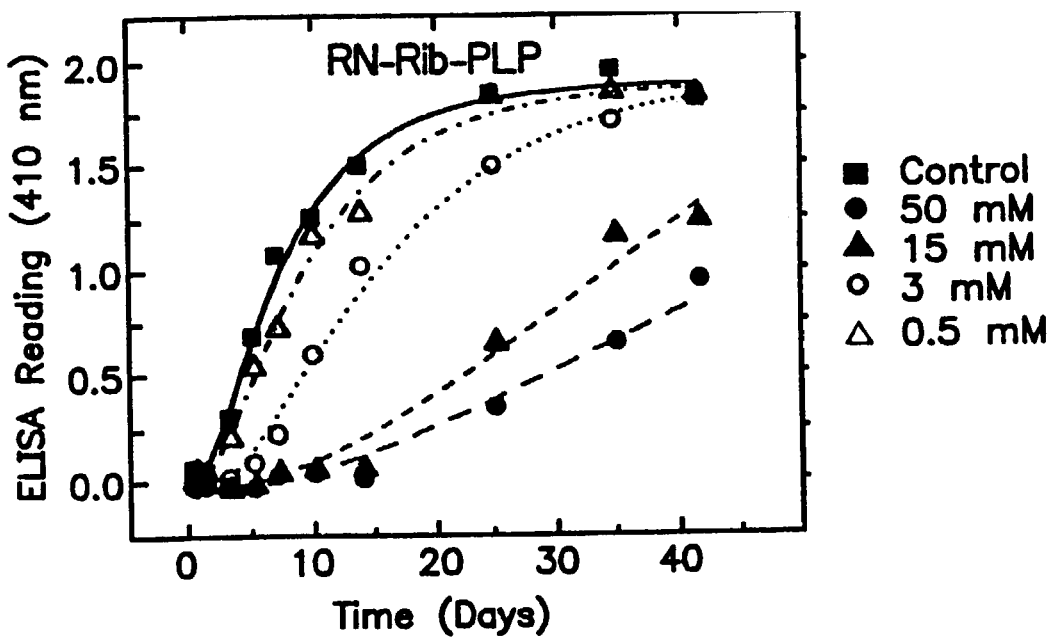
FIG. 13B pyridoxal-5'-phosphate (PLP)
Figure 13C:
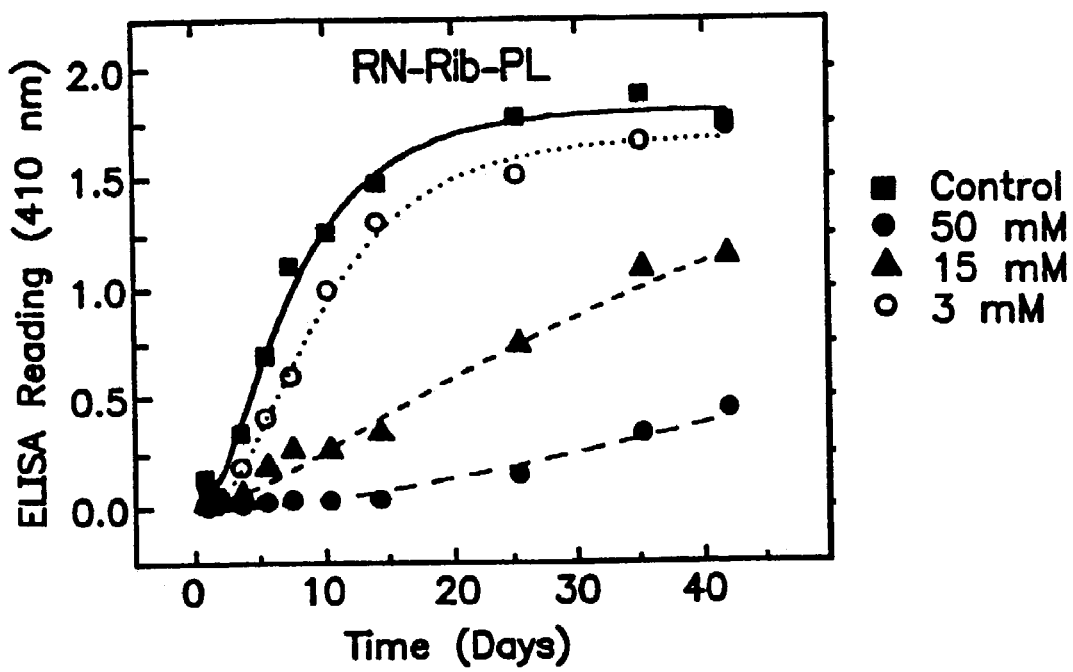
FIG. 13C pyridoxal (PL)
Figure 13D:
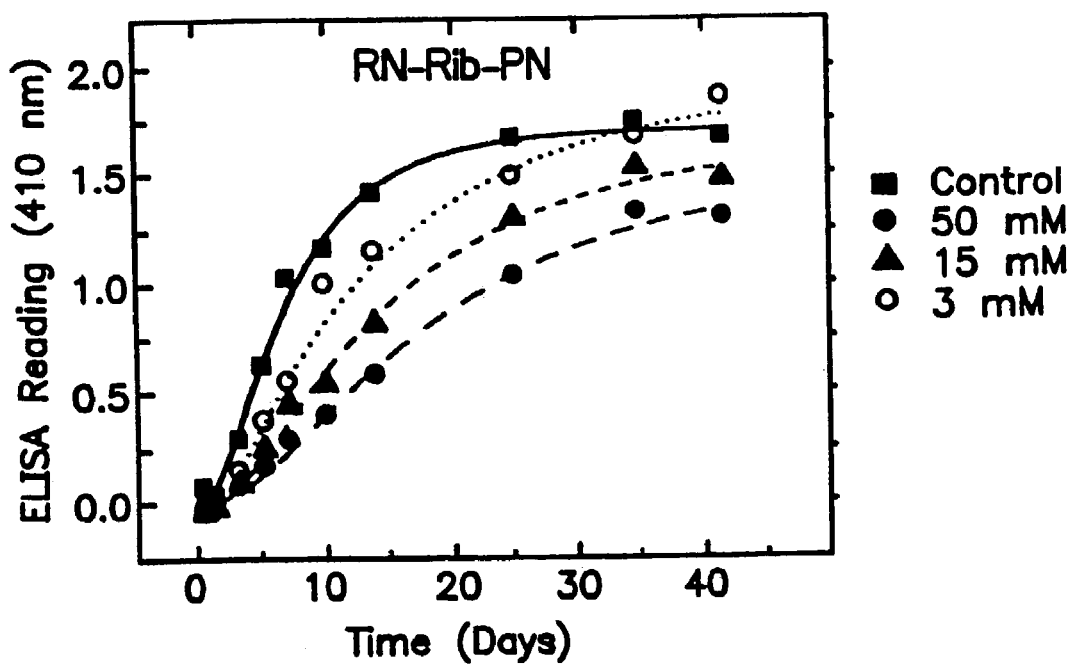
FIG. 13D pyridoxine (PN).

The inhibitory effects of vitamin $B_1$ and $B_6$ derivatives on the kinetics of antigenic AGE formation were evaluated by polyclonal antibodies specific for AGEs. Initial inhibition studies were carried out on the glycation of bovine ribonuclease A (RNase) in the continuous presence of 0.05 M ribose, which is the concentration of ribose where the rate of AGE formation is near maximal. FIG. 13 (control curves, filled rectangles) demonstrates that the formation of antigenic AGEs on RNase when incubated with 0.05 M ribose is relatively rapid, with a half-time of approximately 6 days under these conditions. Pyridoxal-5'-phosphate (FIG. 13B) and pyridoxal (FIG. 13C) significantly inhibited the rate of AGE formation on RNase at concentrations of 50 mM and 15 mM. Surprisingly, pyridoxine, the alcohol form of vitamin $B_6$, also moderately inhibited AGE formation on RNase (FIG. 13D). Of the $B_6$ derivatives examined, pyridoxamine at 50 mM was the best inhibitor of the "final" levels of AGE formed on RNase over the 6-week time period monitored (FIG. 13A).

Inhibition by Vitamin $B_1$ Derivatives of the Overall Kinetics of AGE Formation From Ribose.

Figure 14A:
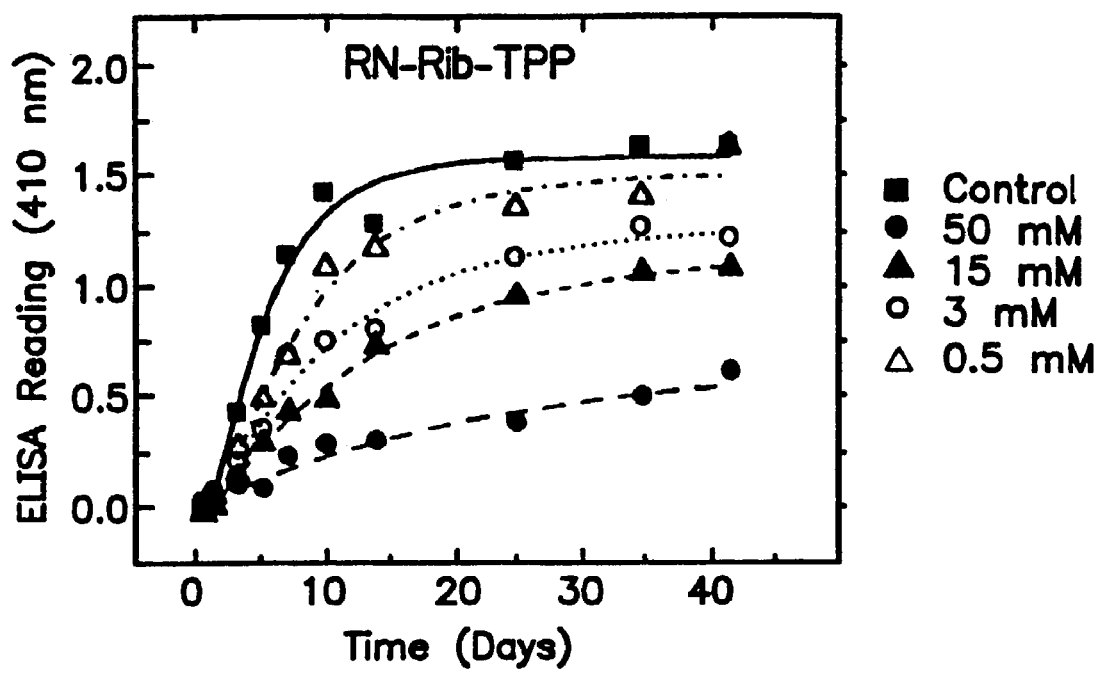
FIG. 14A Thiamine pyrophosphate (TPP)
Figure 14B:
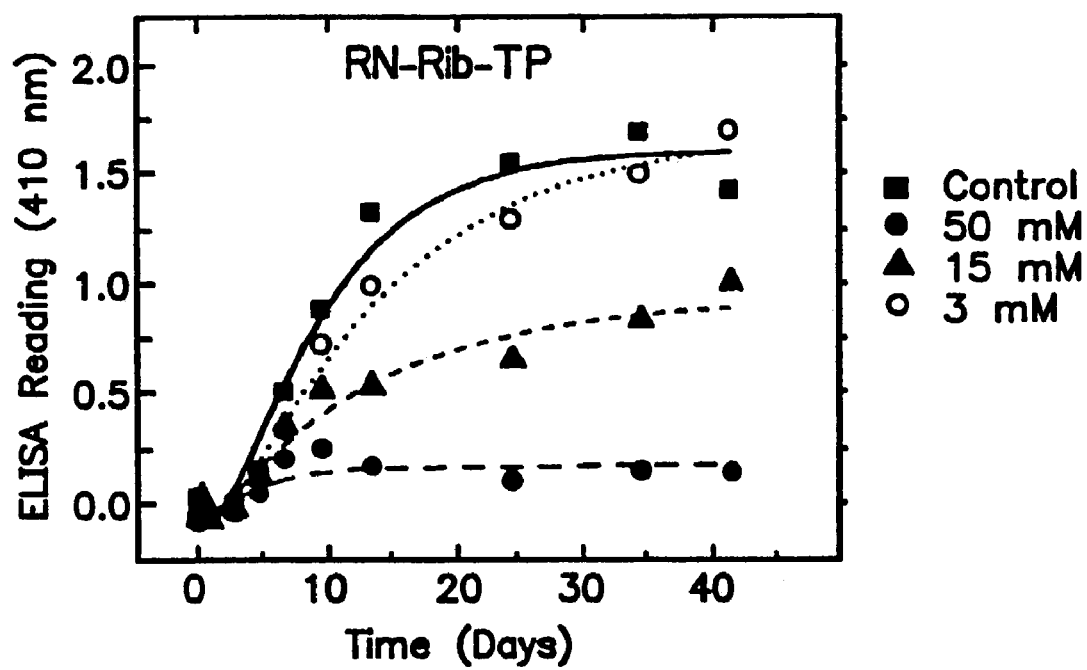
FIG. 14B thiamine monophosphate (TP)
Figure 14C:
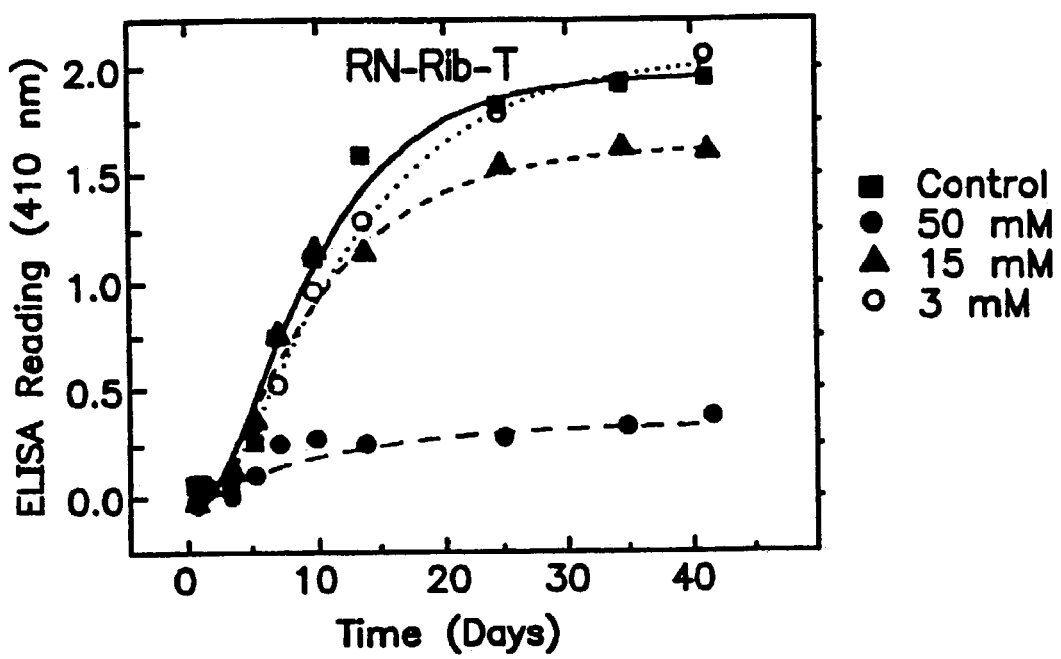
FIG. 14C thiamine (T)

All of the $B_1$ vitamers inhibited antigenic AGE formation on RNase at high concentrations, but the inhibition appeared more complex than for the $B_6$ derivatives (FIGS. 14A–C). In the case of thiamine pyrophosphate as the inhibitor (FIG. 14A), both the rate of AGE formation and the final levels of AGE produced at the plateau appeared diminished. In the case of thiamine phosphate as the inhibitor (FIG. 14B), and thiamine (FIG. 14C), there appeared to be little effect on the rate of AGE formation, but a substantial decrease in the final level of AGE formed in the presence of the highest concentration of inhibitor. In general, thiamine pyrophosphate demonstrated greater inhibition than the other two compounds, at the lower concentrations examined.

Figure 14D:
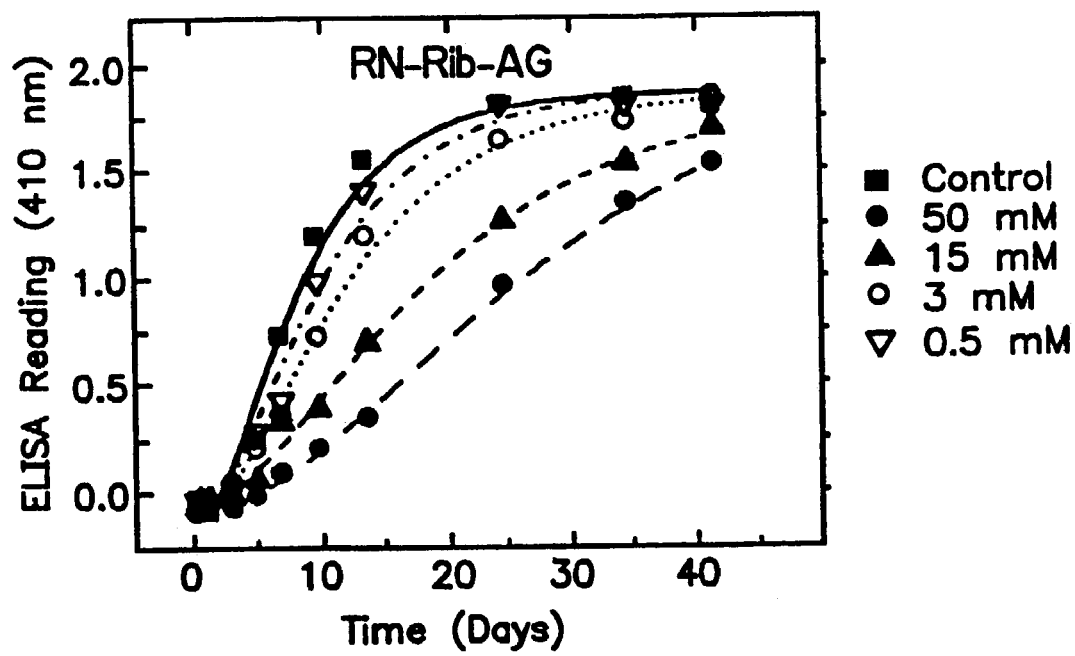
FIG. 14D aminoguanidine (AG).

Inhibition by Aminoguanidine of the Overall Kinetics of AGE Formation from Ribose Inhibition of AGE formation by aminoguanidine (FIG. 14D) was distinctly different from that seen in the $B_1$ and $B_6$ experiments. Increasing concentration of aminoguanidine decreased the rate of AGE formation on RNase, but did not reduce the final level of AGE formed. The final level of AGE formed after the 6-weeks was nearly identical to that of the control for all tested concentrations of aminoguanidine.

Figure 15A:
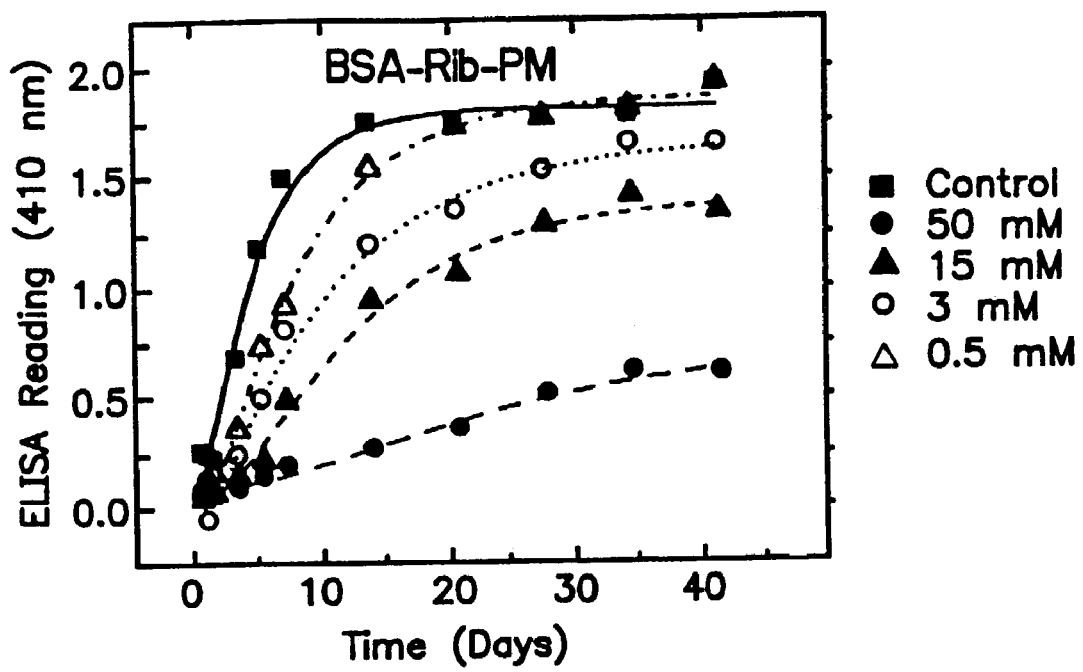
FIG. 15A Pyridoxamine (PM)
Figure 15B:
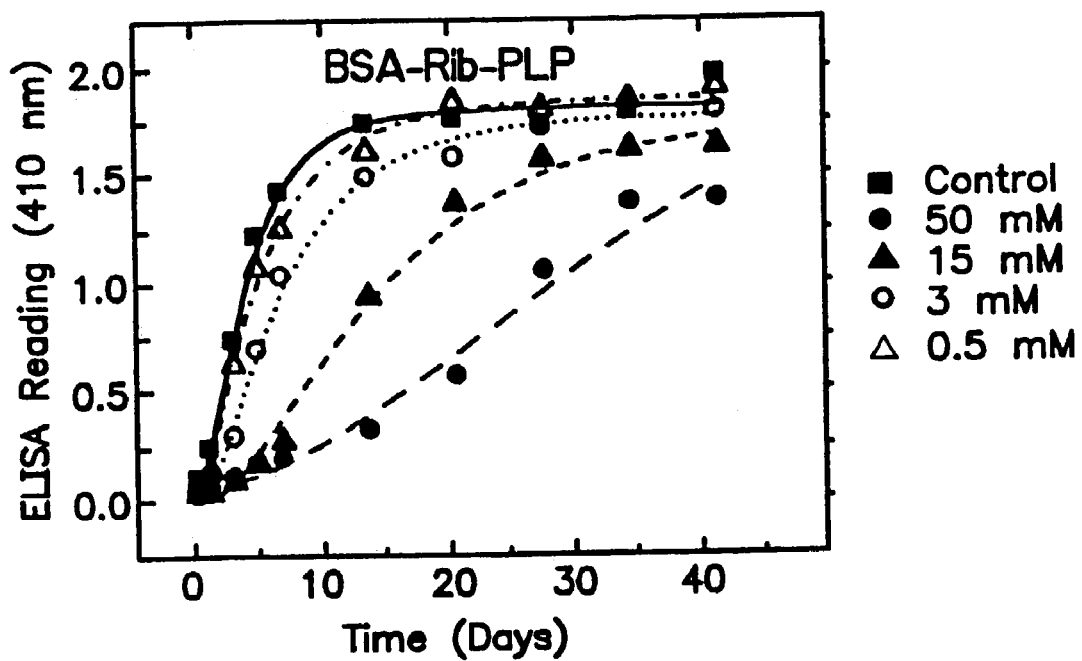
FIG. 15B pyridoxal-5'-phosphate (PLP)
Figure 15C:
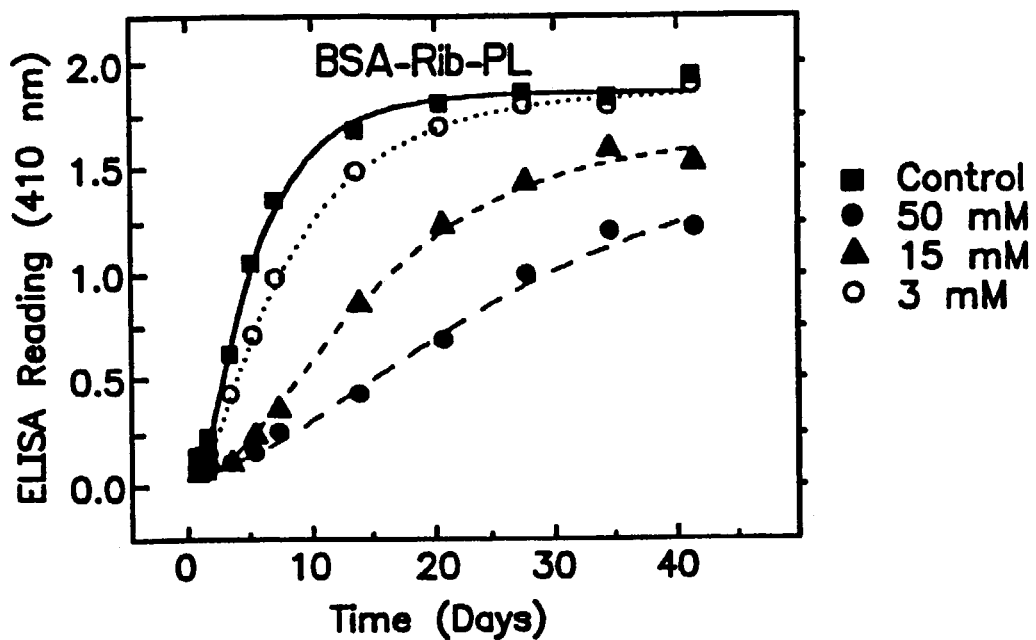
FIG. 15C pyridoxal (PL)
Figure 15D:
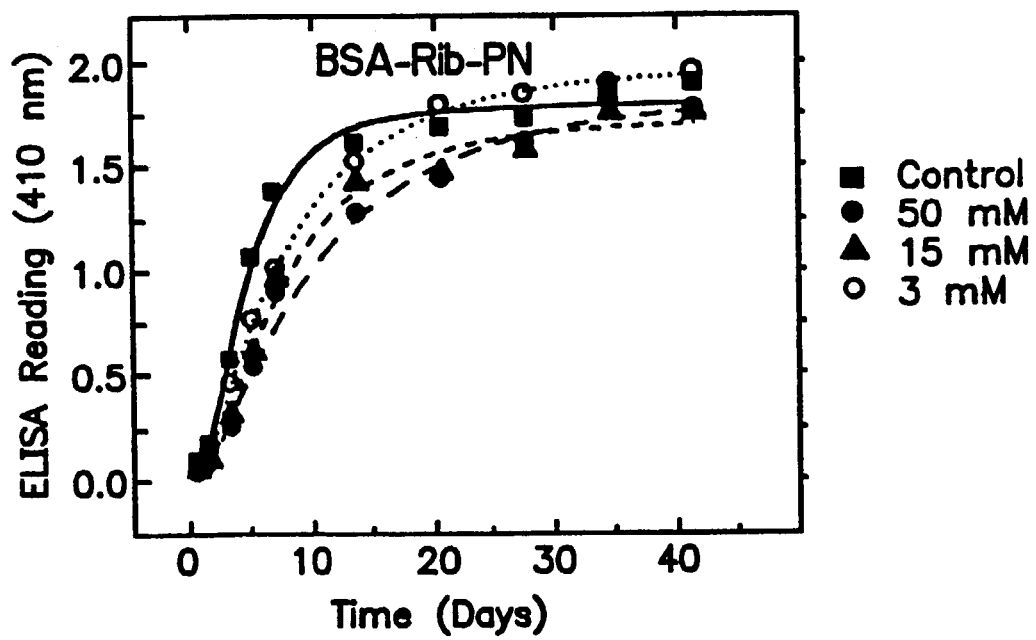
FIG. 15D pyridoxine (PN).
Figure 16A:
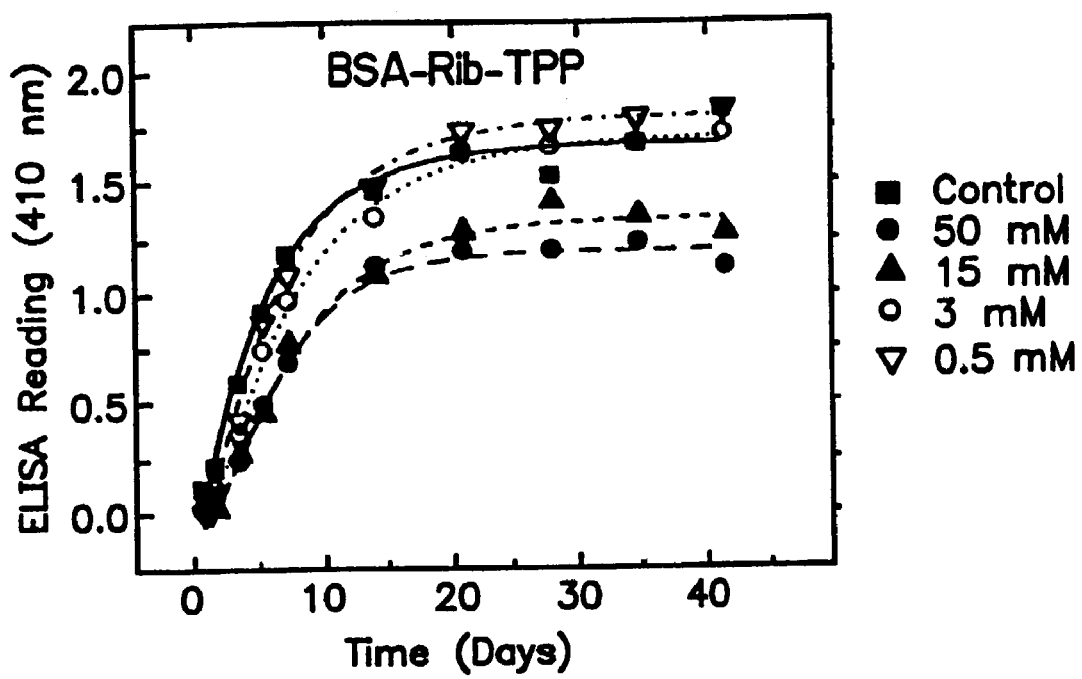
FIG. 16A Thiamine pyrophosphate (TPP)
Figure 16B:
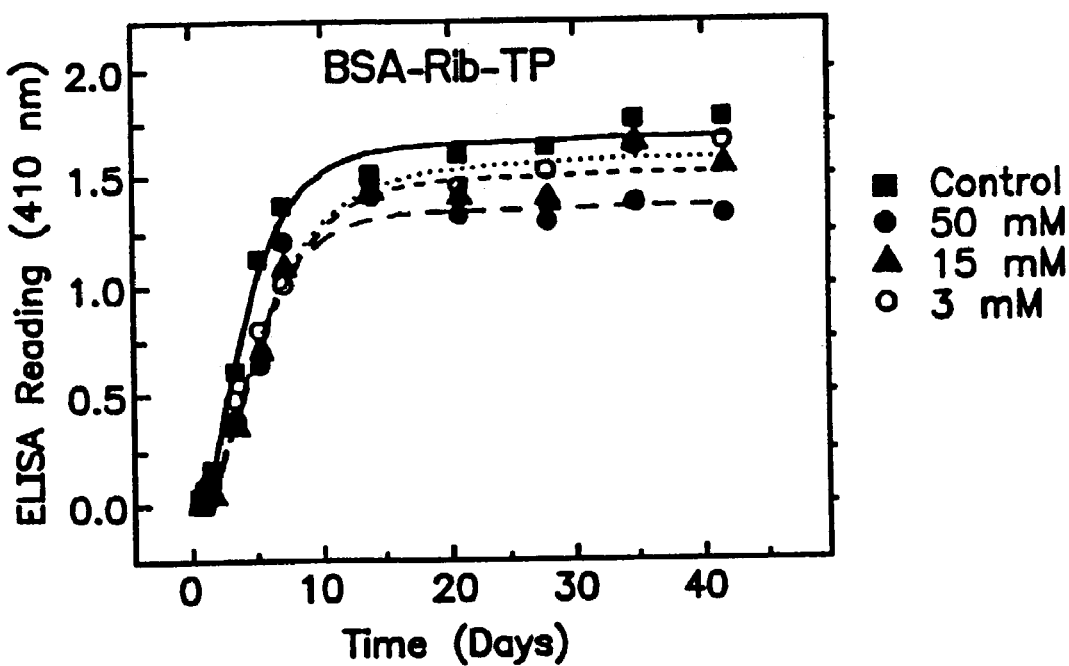
FIG. 16B thiamine monophosphate (TP)
Figure 16C:
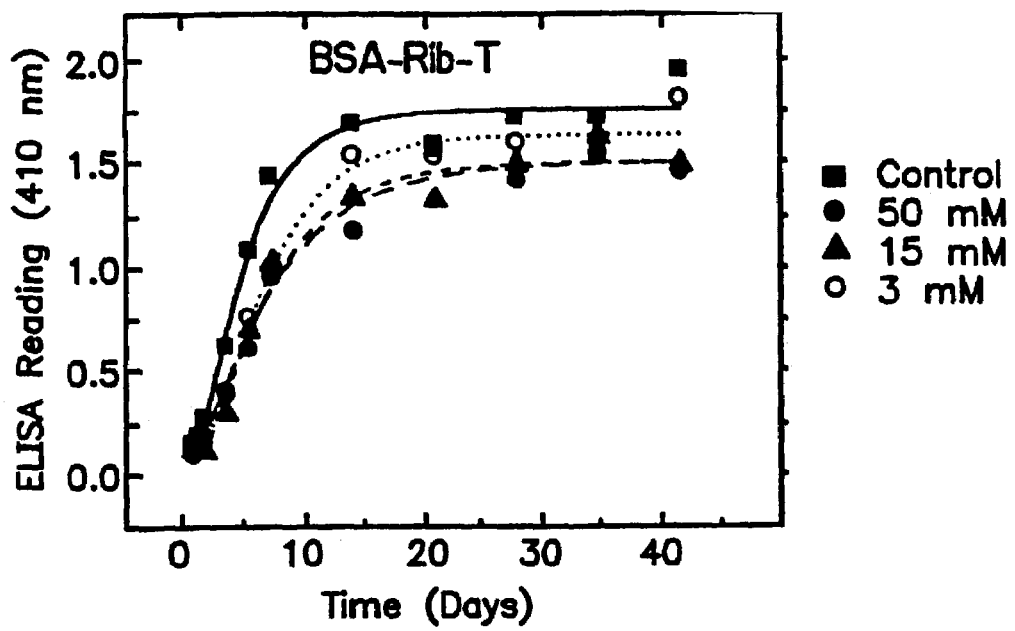
FIG. 16C thiamine (T)
Figure 16D:
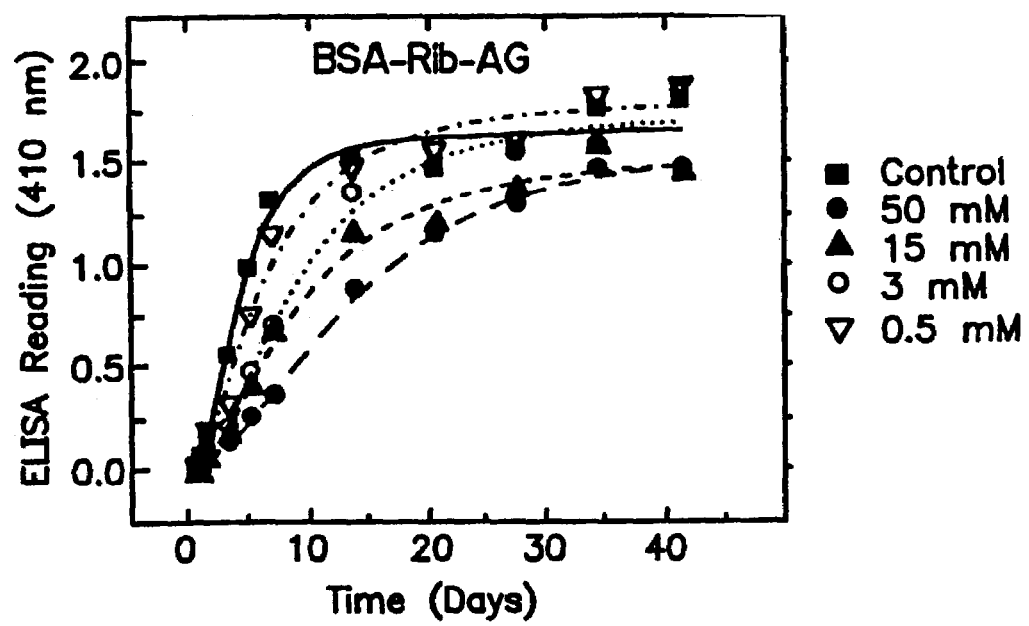
FIG. 16D aminoguanidine (AG).

Inhibition of the Overall Kinetics of AGE Formation in Serum Albumin and Hemoglobin from Ribose Comparative studies were carried out with BSA and human methemoglobin (Hb) to determine whether the observed inhibition was protein-specific. The different derivatives of vitamin $B_6$ (FIGS. 15A–D) and vitamin BI (FIGS. 16A–C) exhibited similar inhibition trends when incubated with BSA as with RNase, pyridoxamine and thiamine pyrophosphate being the most effective inhibitors or each family. Pyridoxine failed to inhibit AGE formation on BSA (FIG. 15D). Pyridoxal phosphate and pyridoxal (FIGS. 15B–C) mostly inhibited the rate of AGE formation, but not the final levels of AGE formed. Pyridoxamine (FIG. 15A) exhibited some inhibition at lower concentrations, and at the highest concentration tested appeared to inhibit the final levels of AGE formed more effectively than any of the other $B_6$ derivatives. In the case of $B_1$ derivatives, the overall extent of inhibition of AGE formation with BSA (FIGS. 16A–C), was less than that observed with RNase (FIGS. 14A–C). Higher concentrations of thiamine and thiamine pyrophosphate inhibited the final levels of AGEs formed, without greatly affecting the rate of AGE formation (FIG. 16C). Aminoguanidine again displayed the same inhibition effects with BSA as seen with RNase (FIG. 16D), appearing to slow the rate of AGE formation without significantly affecting the final levels of AGE formed.

Figure 17A:
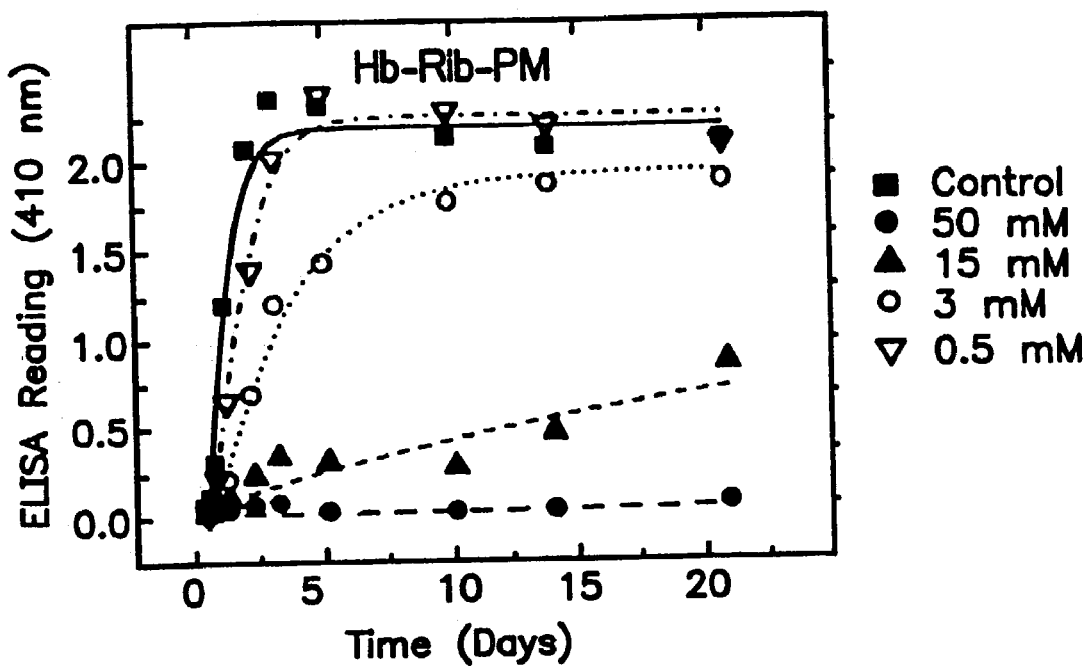
FIG. 17A
Figure 17B:
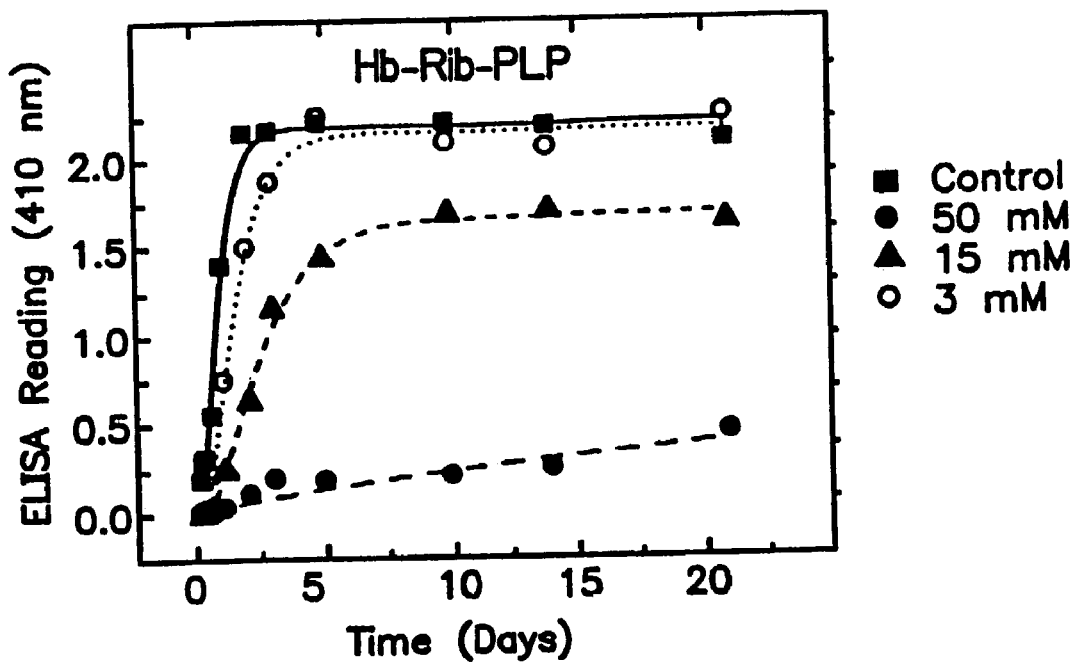
FIG. 17B pyridoxal-5'-phosphate (PLP)
Figure 17C:
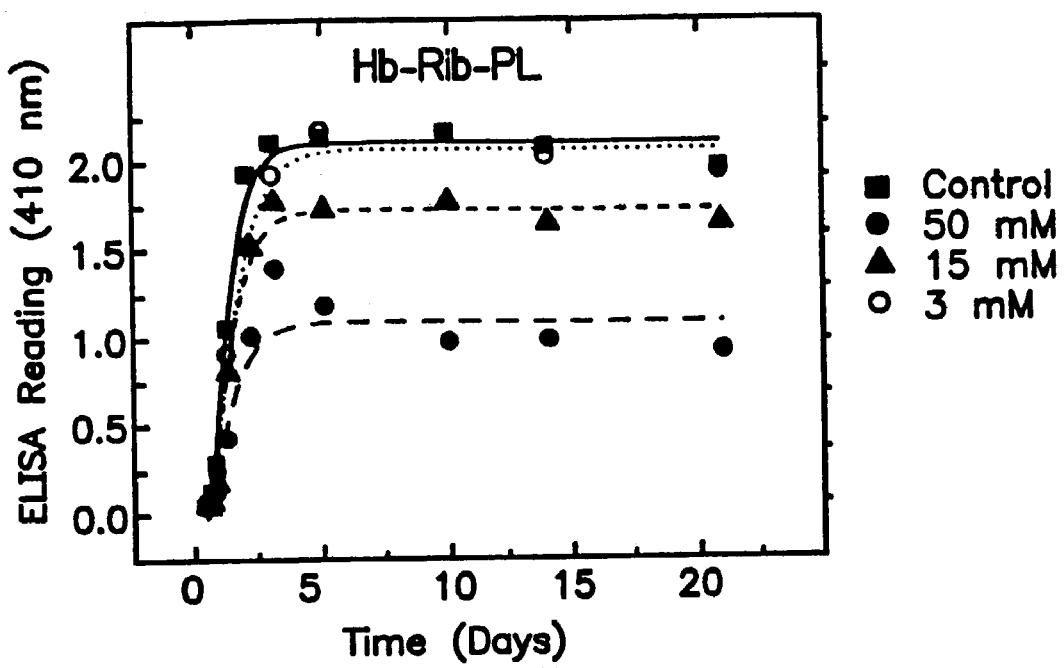
FIG. 17C pyridoxal (PL)
Figure 17D:
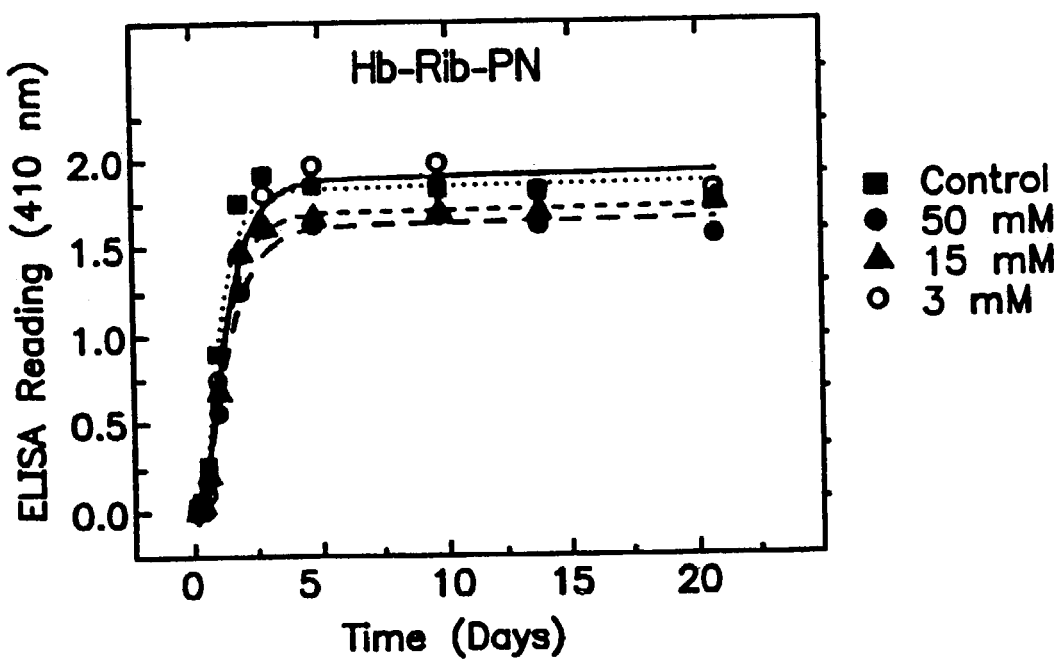
FIG. 17D pyridoxine (PN).

The kinetics of AGE formation was also examined using Hb in the presence of the $B_6$ and $B_1$ vitamin derivatives, and aminoguanidine. The apparent absolute rates of AGE formation were significantly higher with Hb than with either RNase or BSA. However, the tested inhibitors showed essentially similar behavior. The effects of the vitamin $B_6$ derivatives are shown in FIG. 17. Pyrridoxamine showed the greatest inhibition at concentrations of 3 mM and above (FIG. 17A), and was most effective when compared to pyridoxal phosphate (FIG. 17B), pyridoxal (FIG. 17C), and pyridoxine (FIG. 17D). In the case of the $B_1$ vitamin derivatives (data not shown), the inhibitory effects were more similar to the BSA inhibition trends than to RNase. The inhibition was only modest at the highest concentrations tested (50 mM), being nearly 30–50% for all three $B_1$ derivatives. The primary manifestation of inhibition was in the reduction of the final levels of AGE formed.

Inhibition by Vitamin $B_6$ Derivatives of the Kinetics of Post-Amadori Ribose AGE Formation Using the interrupted glycation model to assay for inhibition of the "late" post-Amadori AGE formation, kinetics were examined by incubating isolated Amadori intermediates of either RNase or BSA at 37° C. in the absence of free or reversibly bound ribose. Ribose sugar that was initially used to prepare the intermediates was removed by cold dialysis after an initial glycation reaction period of 24 h. After AGE formation is allowed to resume, formation of AGE is quite rapid (half-times of about 10 h) in the absence of any inhibitors. FIG. 18 shows the effects of pyridoxamine (FIG. 18A), pyridoxal phosphate (FIG. 18B), and pyridoxal (FIG. 18C) on the post-Amadori kinetics of BSA. Pyridoxine did not produce any inhibition (data not shown). Similar experiments were carried out on RNase. Pyridoxamine caused nearly complete inhibition of AGE formation with RNase at 15 mM and 50 mM (FIG. 18D). Pyridoxal did not show any significant inhibition at 15 mM (the highest tested), but pyridoxal phosphate showed significant inhibition at 15 mM. Pyridoxal phosphate is known to be able to affinity label the active site of RNase (Raetz and Auld, 1972, *Biochemistry* 11:2229–2236).

Figure 18A:
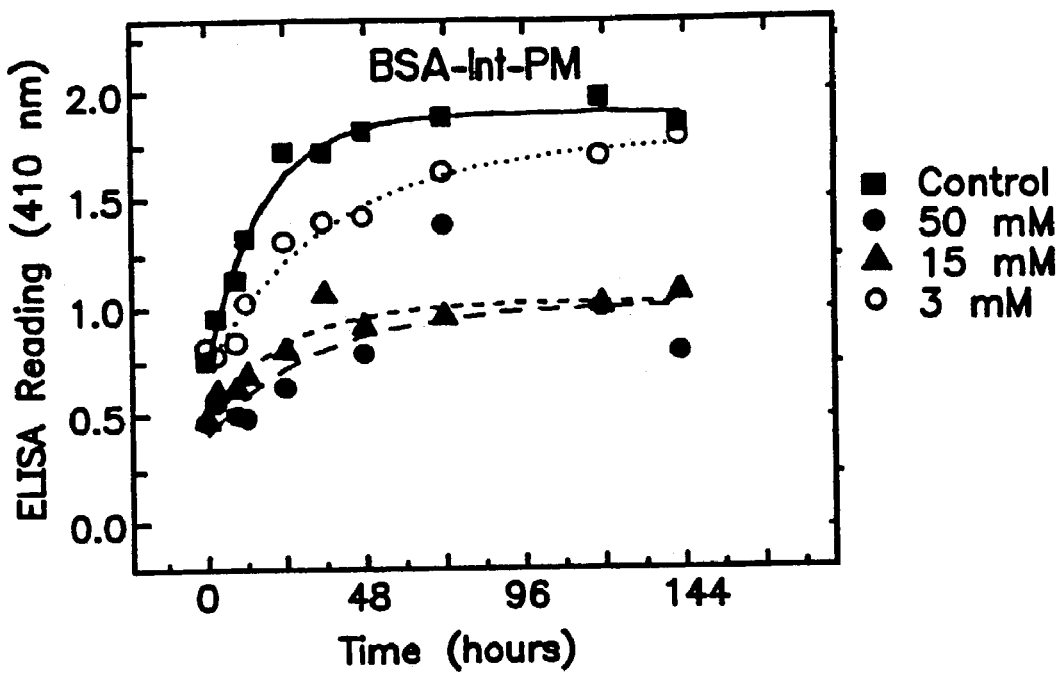
FIG. 18A BSA and Pyridoxamine (PM)
Figure 18B:
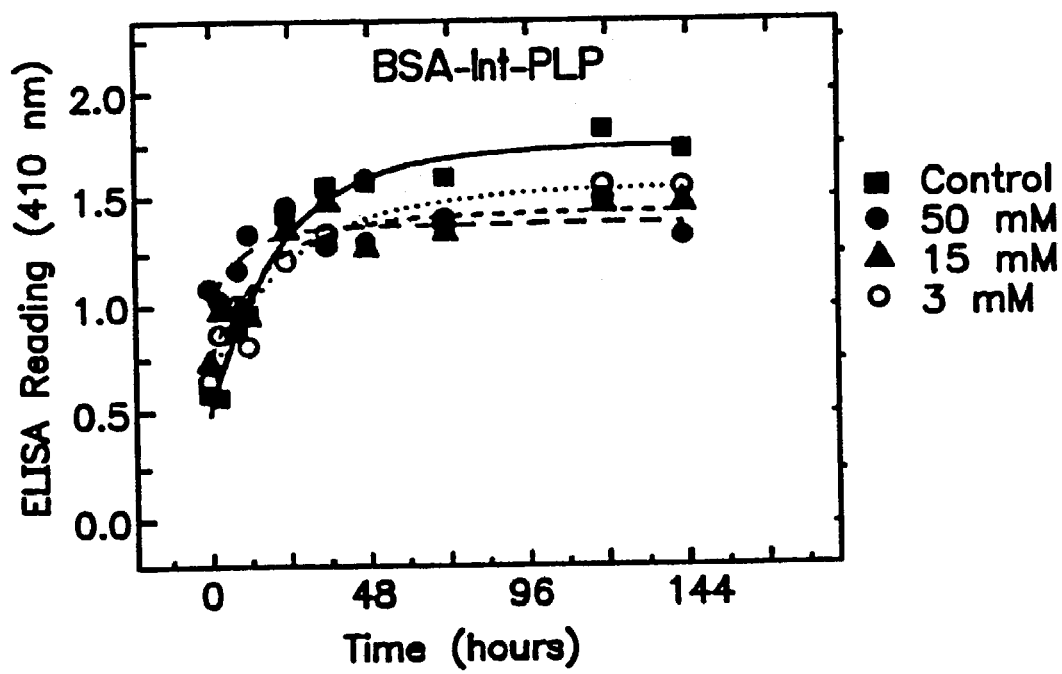
FIG. 18B BSA and pyridoxal-5'-phosphate (PLP)
Figure 18C:
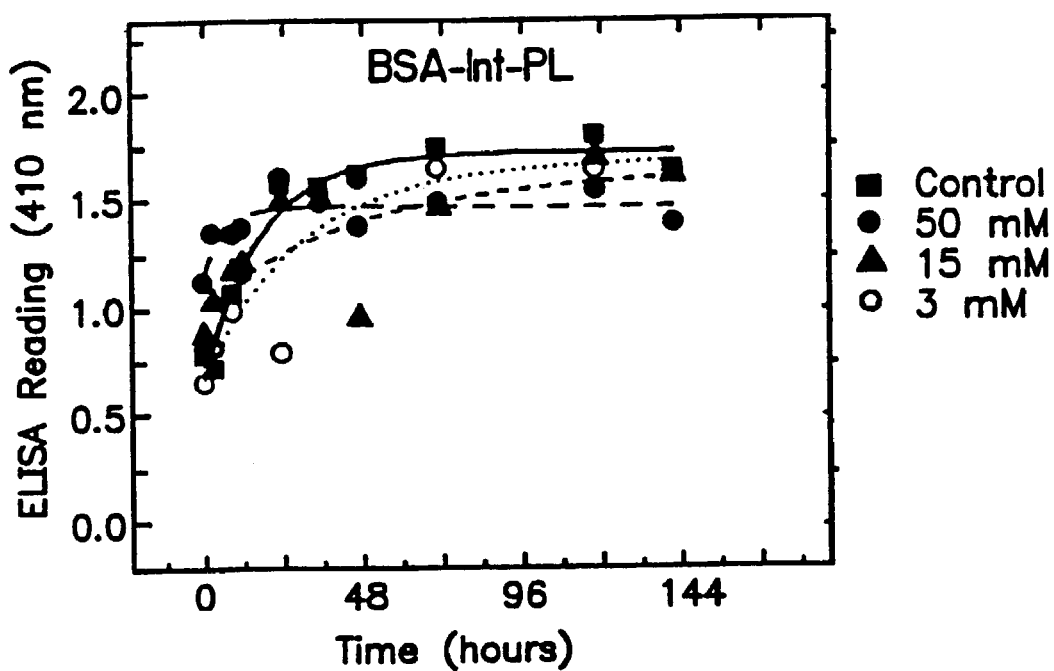
FIG. 18C BSA and pyridoxal (PL)
Figure 18D:
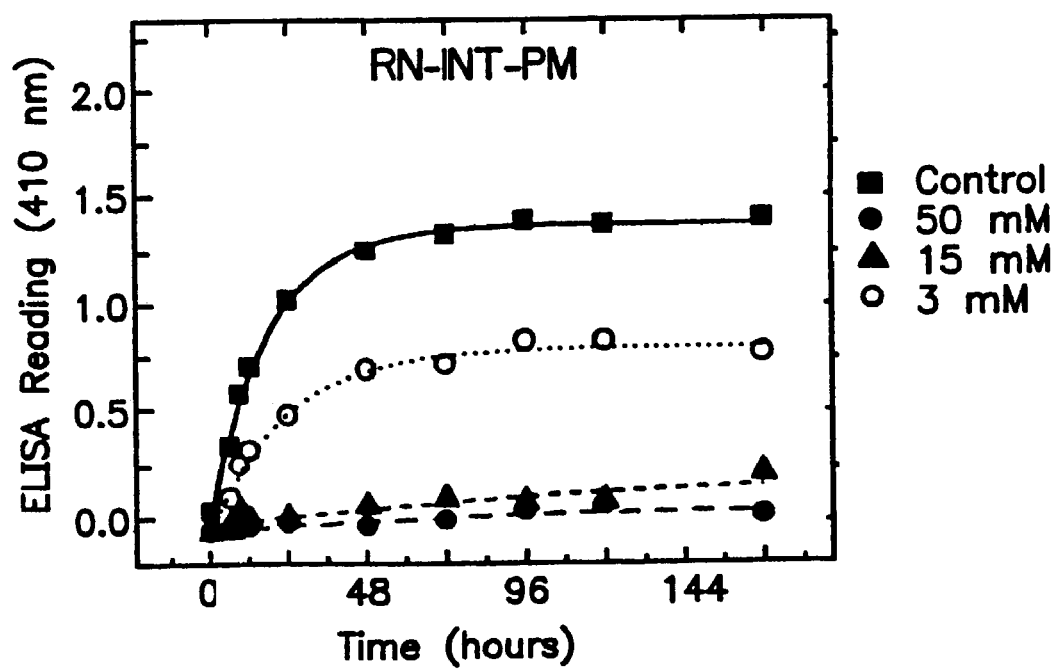
FIG. 18D RNase and pyridoxamine (PM).

With BSA, unlike RNase, a significant amount of antigenic AGE formed during the 24 h initial incubation with RNase (25–30%), as evidenced by the higher ELISA readings after removal of ribose at time zero for FIGS. 18A–C. For both BSA and RNase, the inhibition, when seen, appears to manifest as a decrease in the final levels of AGE formed rather than as a decrease in the rate of formation of AGE.

Figure 19A:
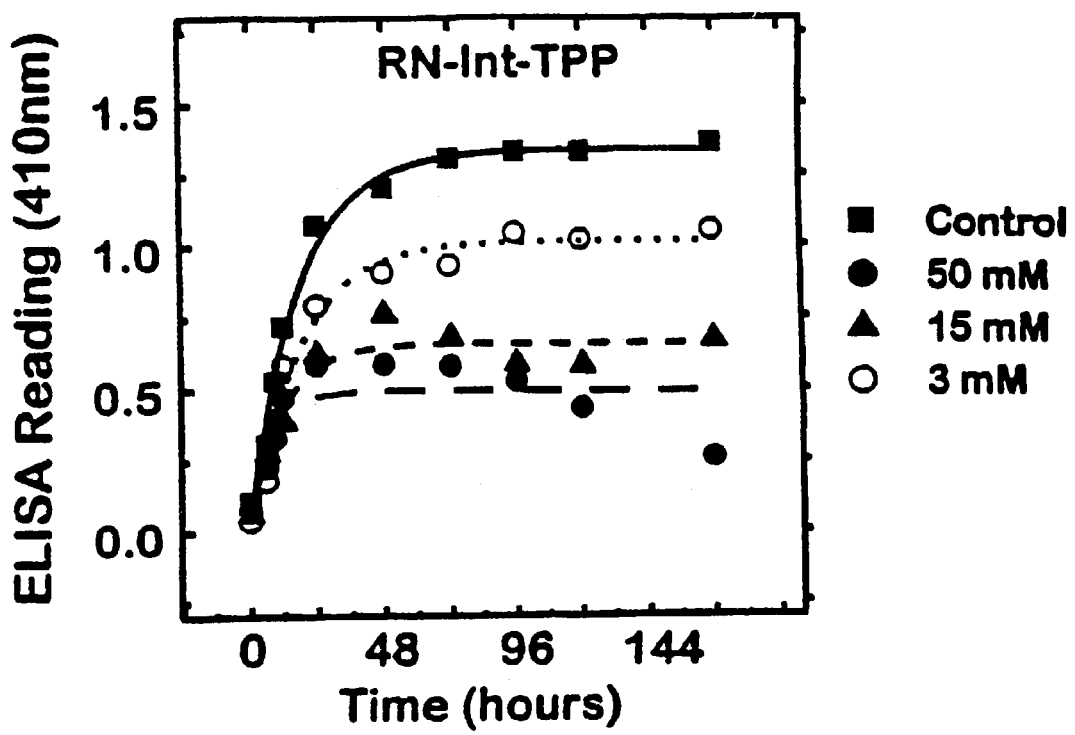
FIG. 19A RNase, FIG. 19B BSA.
Figure 19B:
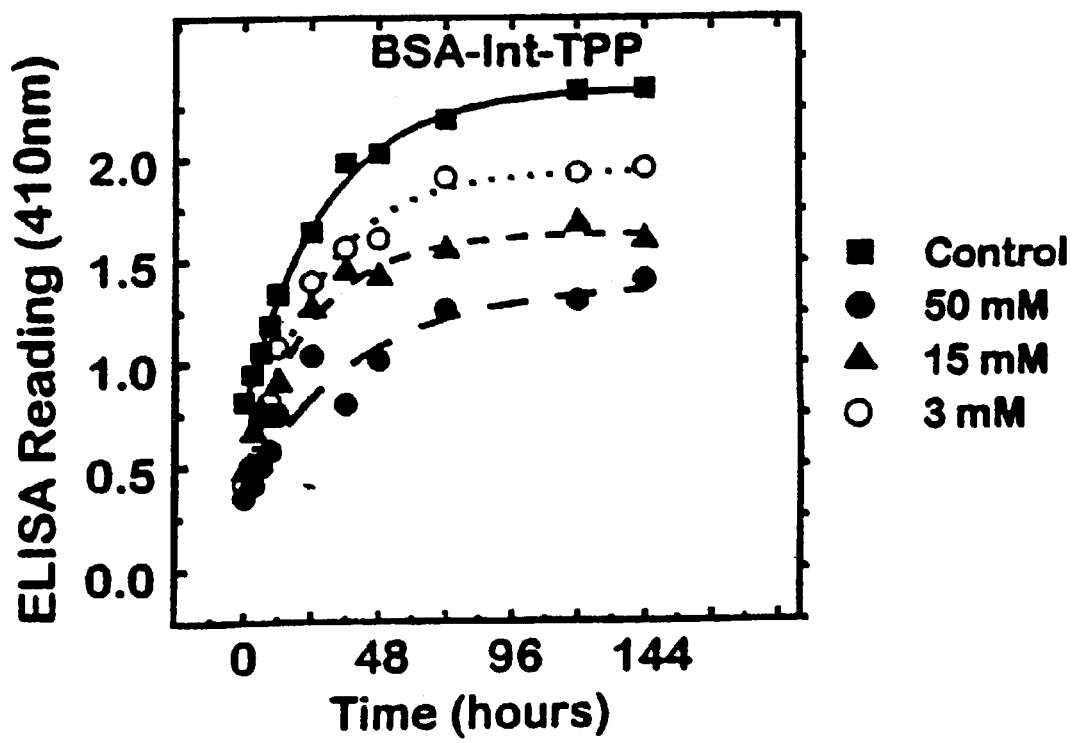
FIG. 19 are graphs depicting the effect of thiamine pyrophosphate on post-Amadori AGE formation after interrupted glycation by ribose.

Inhibition by Vitamin $B_1$ Derivatives of the Kinetics of Post-Amadori Ribose AGE Formation Thiamine pyrophosphate inhibited AGE formation more effectively than the other $B_1$ derivatives with both RNase and BSA (FIG. 19). Thiamine showed no effect, while thiamine phosphate showed some intermediate effect. As with the $B_6$ assays, the post-Amadori inhibition was most apparently manifested as a decrease in the final levels of AGE formed.

Figure 21:
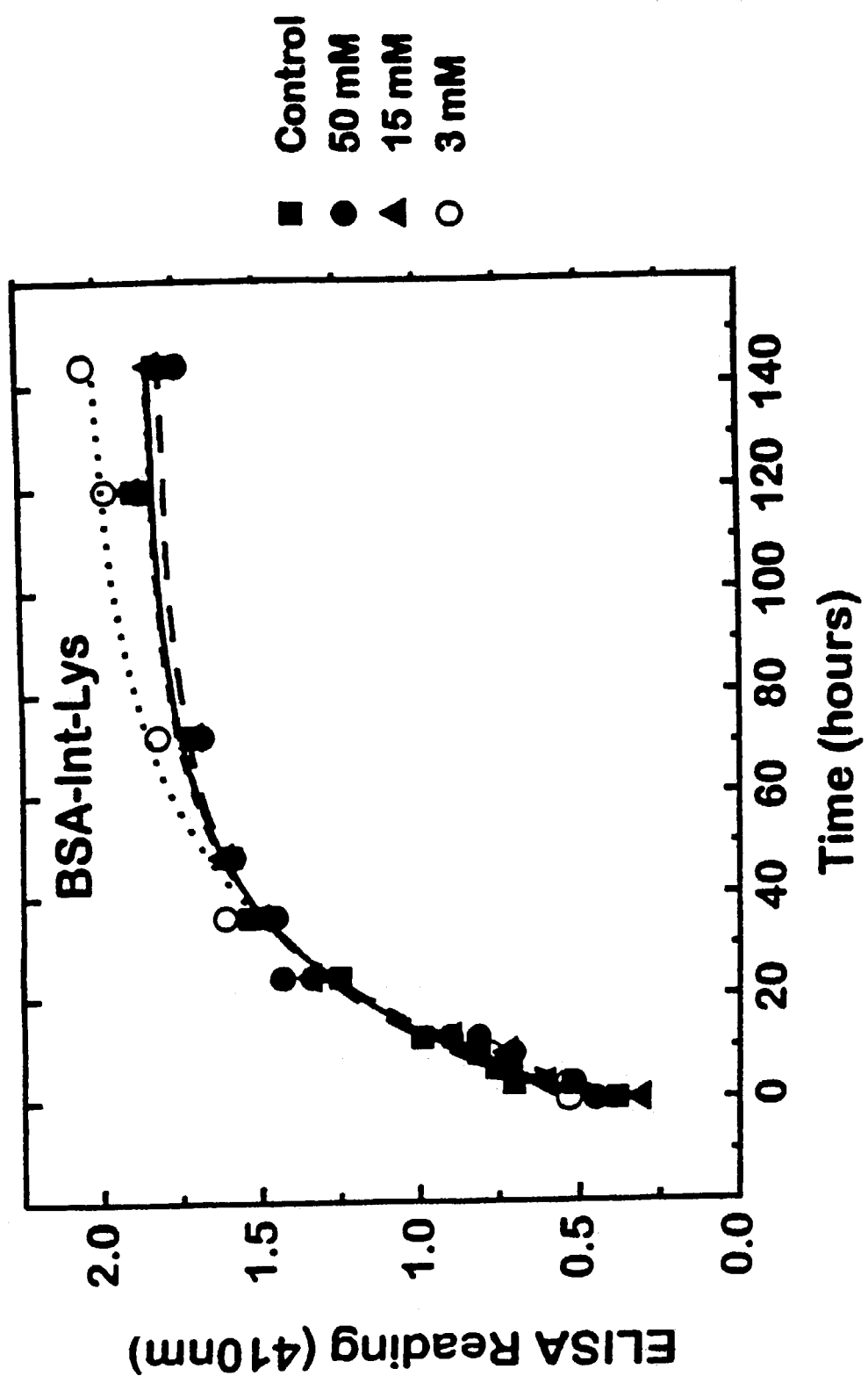
FIG. 21 is a graph depicting the effect of N-acetyl-L-lysine on post-Amadori AGE formation after interrupted glycation by ribose.

Effects of Aminoguanidine and $N^\alpha$-acetyl-L-lysine on the Kinetics of Post-Amadori Ribose AGE Formation FIG. 20 shows the results of testing aminoguanidine for inhibition of post-Amadori 1o AGE formation kinetics with both BSA and RNase. At 50 mM, inhibition was about 20% in the case of BSA (FIG. 20B), and less than 15% with RNase (FIG. 20A). The possibility of inhibition by simple amino-containing functionalities was also tested using $N^\alpha$-acetyl-L-lysine (FIG. 21), which contains only a free $N^\alpha$-amino group. $N^\alpha$-acetyl-L-lysine at up to 50 mM failed to exhibit any significant inhibition of AGE formation.

Discussion

Numerous studies have demonstrated that aminoguanidine is an apparently potent inhibitor of many manifestations of nonenzymatic glycation (Brownlee et al., 1986; Brownlee, 1992,1994, 1995). The inhibitory effects of aminoguanidine on various phenomena that are induced by reducing sugars are widely considered as proof of the involvement of glycation in many such phenomena. Aminoguanidine has recently entered into a second round of Phase III clinical trials for ameliorating the complications of diabetes thought to be caused by glycation of connective tissue proteins due to high levels of sugar.

Data from the kinetic study of uninterrupted "slow" AGE formation with RNase induced by glucose (Example 1) confirmed that aminoguanidine is an effective inhibitor, and further identified a number of derivatives of vitamins $B_1$ and $B_6$ as equally or slightly more effective inhibitors. However, the inhibition by aminoguanidine unexpectedly appeared to diminish in effect at the later stages of the AGE formation reaction. Due to the slowness of the glycation of protein with glucose, this surprising observation could not be fully examined. Furthermore, it has been suggested that there may be questions about the long-term stability of aminoguanidine (Ou and Wolff, 1993, supra).

Figure 22A:
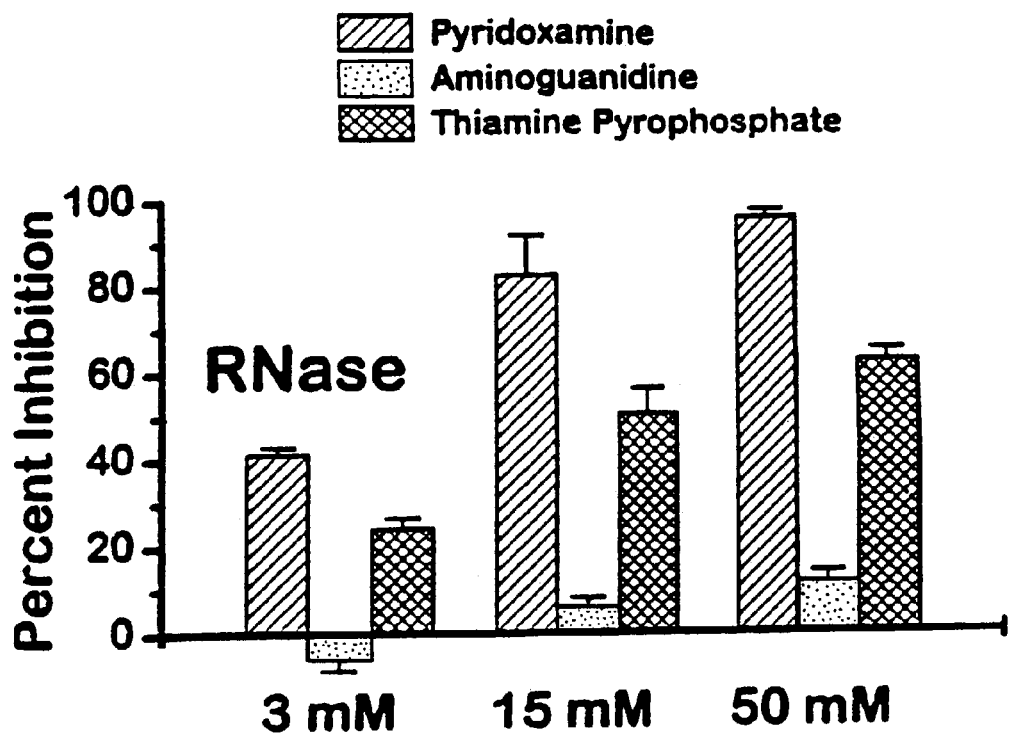
FIG. 22 are bar graphs showing a comparison of post-Amadori inhibition of AGE formation by thiamine pyrophosphate (TPP), pyridoxamine (PM) and aminoguanidine (AG) after interrupted glycation of RNase (FIG. 22A) and BSA (FIG. 22B) by ribose.
Figure 22B:
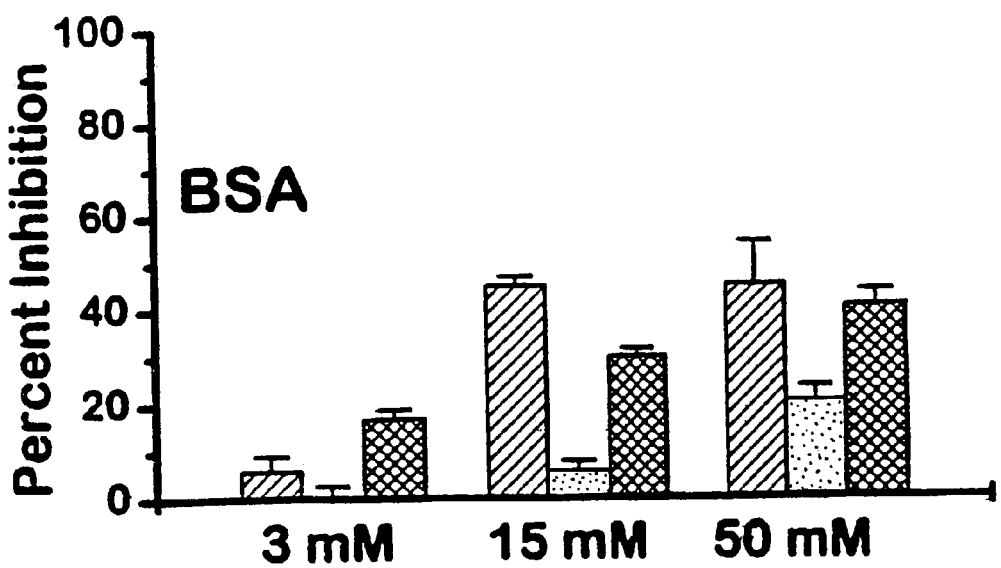

Analysis using the much more rapid glycation by ribose allowed for the entire time-course of AGE formation to be completely observed and quantitated during uninterrupted glycation of protein. The use of interrupted glycation uniquely-allowed further isolation and examination of only post-Amadori antigenic AGE formation in the absence of free and reversibly bound (Schiff base) ribose. Comparison of the data from these two approaches with the earlier glucose glycation kinetics has provided novel insights into the mechanisms and effectiveness of various inhibitors. FIG. 22 are bar graphs which depict summarized comparative data of percent inhibition at defined time points using various concentrations of inhibitor. FIG. 22A graphs the data for inhibition after interrupted glycation of RNase AGE formation in ribose. FIG. 22B graphs the data for inhibition after interrupted glycation of BSA AGE formation by ribose.

The overall results unambiguously demonstrate that aminoguanidine slows the rate of antigenic AGE formation in the presence of sugar but has little effect on the final amount of post-Amadori AGE formed. Thus observations limited to only the initial "early" stages of AGE formation which indicate efficacy as an inhibitor may in fact be misleading as to the true efficacy of inhibition of post-Amadori AGE formation. Thus the ability to observe a full-course of reaction using ribose and interrupted glycation gives a more complete picture of the efficacy of inhibition of post-Amadori AGE formation.

EXAMPLE 4

Animal Model & Testing of in vivo Effects of AGE Formation/Inhibitors

Hyperglycemia can be rapidly induced (within one or two days) in rats by administration of streptozocin (aka. streptozotocin, STZ) or alloxan. This has become a common model for diabetes melitus. However, these rats manifest nephropathy only after many months of hyperglycemia, and usually just prior to death from end-stage renal disease (ESRD). It is believed that this pathology is caused by the irreversible glucose chemical modification of long-lived proteins such as collagen of the basement membrane. STZ-diabetic rats show albuminuria very late after induction of hyperglycemia, at about 40 weeks usually only just prior to death.

Because of the dramatic rapid effects of ribose demonstrated in vitro in the examples above, it was undertaken to examine the effects of ribose administration to rats, and the possible induction of AGEs by the rapid ribose glycation. From this study, a rat model for accelerated ribose induced pathology has been developed.

Effects of Very Short-term Ribose Administration in vivo

Phase I Protocol

Two groups of six rats each were given in one day either:
a. 300 mM ribose (two intraperitoneal infusions 6–8 hours apart, each 5% of body weight as ml); or
b. 50 mM ribose (one infusion)

Rats were then kept for 4 days with no further ribose administration, at which time they were sacrificed and the following physiological measurements were determined: (i) initial and final body weight; (ii) final stage kidney weight; (iii) initial and final tail-cuff blood pressure; (iv) creatinine clearance per 100 g body weight.

Albumin filtration rates were not measured, since no rapid changes were. initially anticipated. Past experience with STZ-diabetic rats shows that albuminuria develops very late (perhaps 40 weeks) after the induction of hyperglycemia and just before animals expire.

Figure 23:
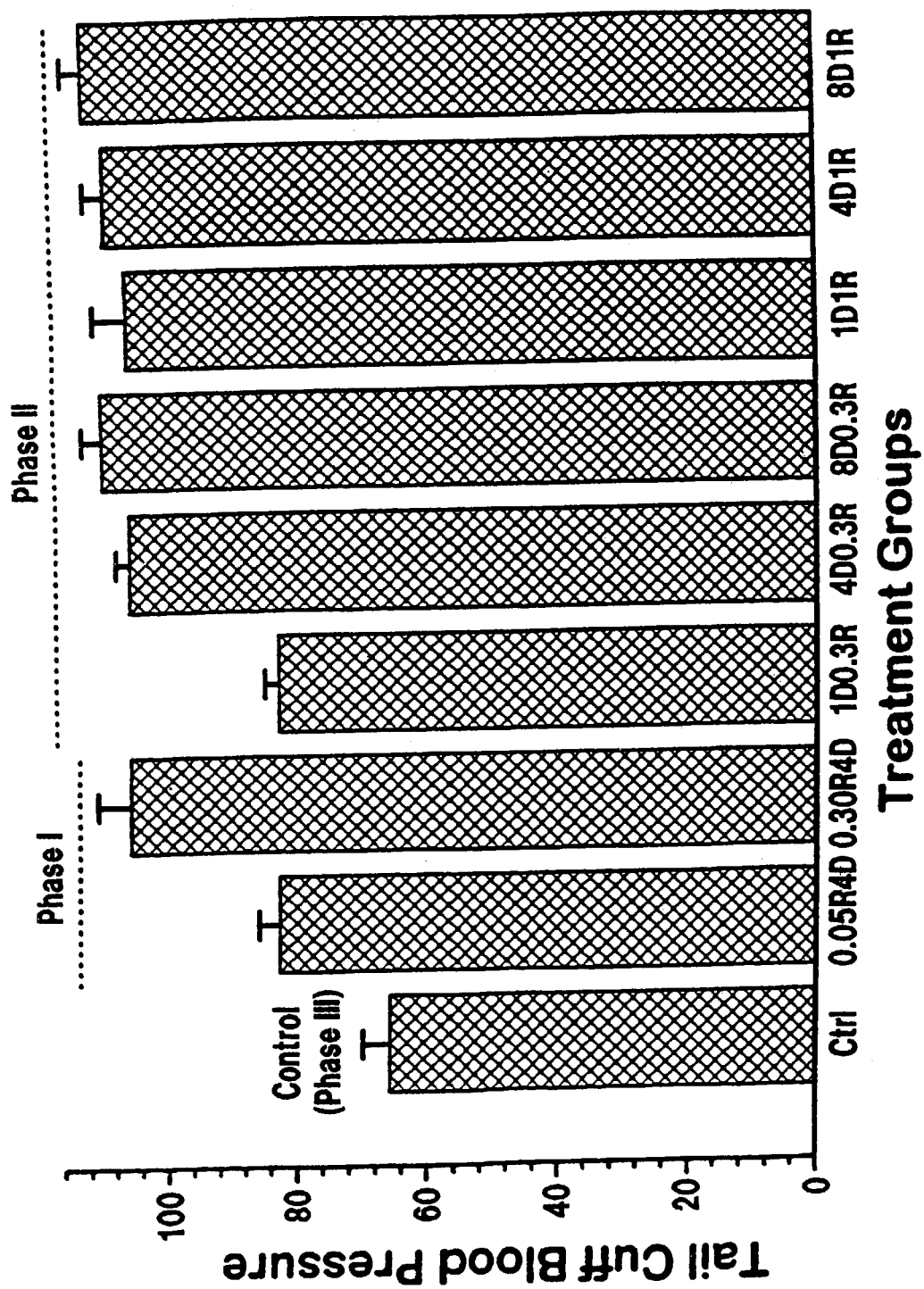
FIG. 23 is a bar graph showing the effects of Ribose treatment in vivo alone on rat tail-cuff blood pressure. Treatment was with 0.05 M, 0.30 M, and 1 M Ribose (R) injected for 1, 2 or 8 Days (D).

Renal Physiology Results a. Final body weight and final single kidney weight was same for low and high ribose treatment groups.
b. Tail-cuff blood pressure increased from 66±4 to 83±3 for rats treated with low ribose (1×50 mM), and from 66±4 to 106±5 for rats treated with high ribose (2×300 mM). These results are shown in the bar graph of FIG. 23.
c. Creatinine clearance, as cc per 100 g body weight, was decreased (normal range expected about 1.0–1.2) in a dose-dependent fashion to 0.87±0.15 for the low ribose group, and decreased still further 30% to 0.62±0.13 for the high ribose group. These results are shown in the bar graph of FIG. 24.

Phase I Conclusion

A single day's ribose treatment caused a dose-dependent hypertension and a dose-dependent decrease in glomerular clearance function manifest 4 days later. These are significant metabolic changes of diabetes seen only much later in STZ-diabetic rats. These phenomenon can be hypothesized to be due to ribose irreversible chemical modification (glycation) of protein in vivo.

Effect of Exposure to Higher Ribose Concentrations for Longer Time

Phase II Protocol

Groups of rats (3–6) were intraperitoneally given 0.3 M "low ribose dose" (LR) or 1.0 M "high ribose dose" (HR) by twice-daily injections for either (i) 1 day, (ii) a "short-term" (S) of 4 days, or (iii) a "long-term" (L) of 8 days. Additionally, these concentrations of ribose were included in drinking water.

Figure 24:
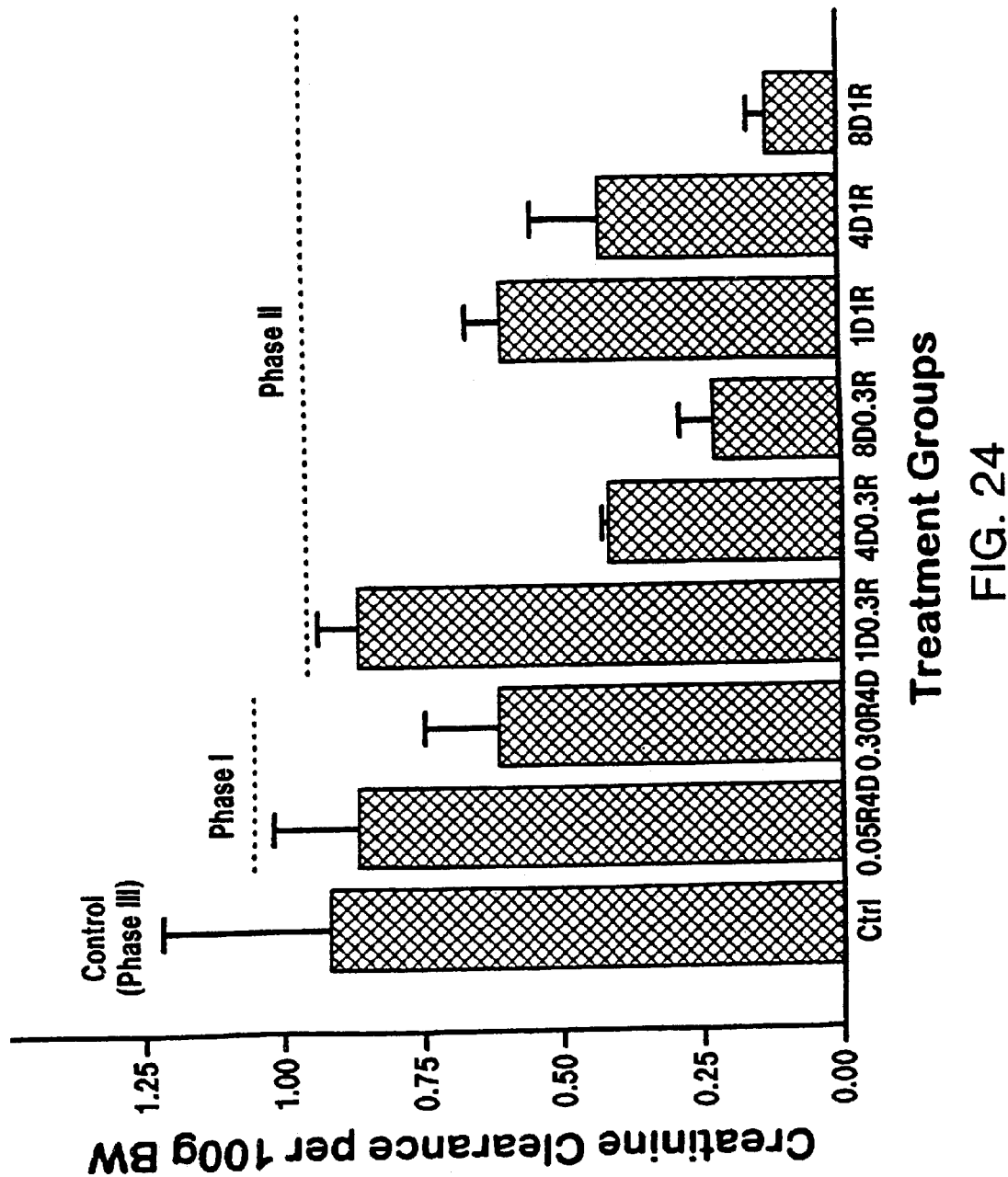
FIG. 24 is a bar graph showing the effects of Ribose treatment in vivo alone on rat creatinine clearance (Clearance per 100 g Body Weight). Treatment was with 0.05 M, 0.30 M, and 1 M Ribose (R) injected for 1, 2 or 8 Days (D).
Figure 25:
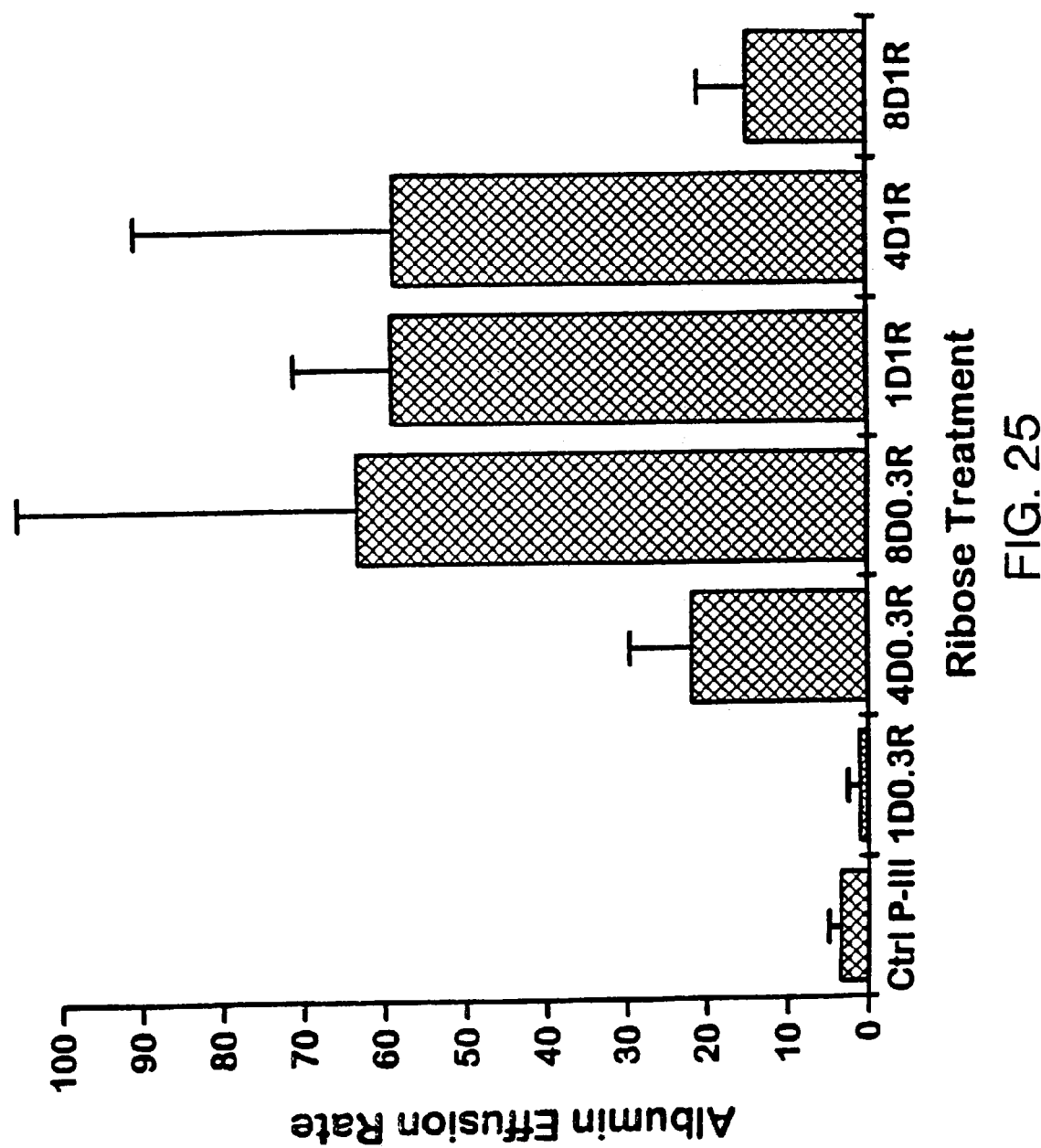
FIG. 25 is a bar graph showing the effects of Ribose treatment in vivo alone on rat Albuminuria (Albumin effusion rate). Treatment was with 0.30 M, and 1 M Ribose (R) injected for 1, 2 or 8 Days (D).

Renal Physiology Results a. Tail-cuff blood pressure increased in all groups of ribose-treated rats, confirming Phase I results. (FIG. 23).
b. Creatinine clearance decreased in all groups in a ribose dose-dependent and time-dependent manner (FIG. 24).
c. Albumin Effusion Rate (AER) increased significantly in a ribose-dependent manner at 1-day and 4-day exposures. However, it showed some recovery at 8 day relative to 4 day in the high-dose group but not in the low-dose group. These results are shown in the bar graph of FIG. 25.
d. Creatinine clearance per 100 g body weight decreased for both low- and high-ribose groups to about the same extent in a time-dependent manner (FIG. 24).

Phase II Conclusion

Exposure to ribose for as little as 4 days leads to hypertension and renal dysfunction, as manifest by both decreased creatinine clearance and increased albumin filtration. These changes are typical of diabetes and are seen at much later-times in STZ-diabetic rats.

Intervention by two new Therapeutic Compounds and Aminoguanidine

Phase III Protocol

Sixty rats were randomized into 9 different groups, including those exposed to 1 M ribose for 8 days in the presence and absence of aminoguanidine, pyridoxamine, and thiamine pyrophosphate as follows:

Control Groups:
(i) no treatment;
(ii) high dose (250 mg/kg body weight) of pyridoxamine ("compound-P");
(iii) high dose (250 mg/kg body weight of thiamine pyrophosphate ("compound-T" or "TPP"); and
(iv) low dose (25 mg/kg body weight) of aminoguanidine ("AG").

Test Groups:
(i) only 1 M ribose-saline (2×9 cc daily IP for 8 days);
(ii) ribose plus low dose ("LP") of pyridoxamine (25 mg/kg body weight injected as 0.5 ml with 9 cc ribose);
(iii) ribose plus high dose ("HP") of pyridoxamine (250 mg/kg body weight injected as 0.5 ml with 9 cc ribose);

(iv) ribose plus high dose ("HT") of thiamine pyrophosphate (250 mg/kg body weight injected as 0.5 ml with 9 cc ribose); and (v) ribose plus low dose of amino guanidine (25 mg/kg body weight injected as 0.5 ml with 9 cc ribose).

Unlike Phase II, no ribose was administered in drinking water. Intervention compounds were pre-administered for one day prior to introducing them with ribose.

Figure 26:
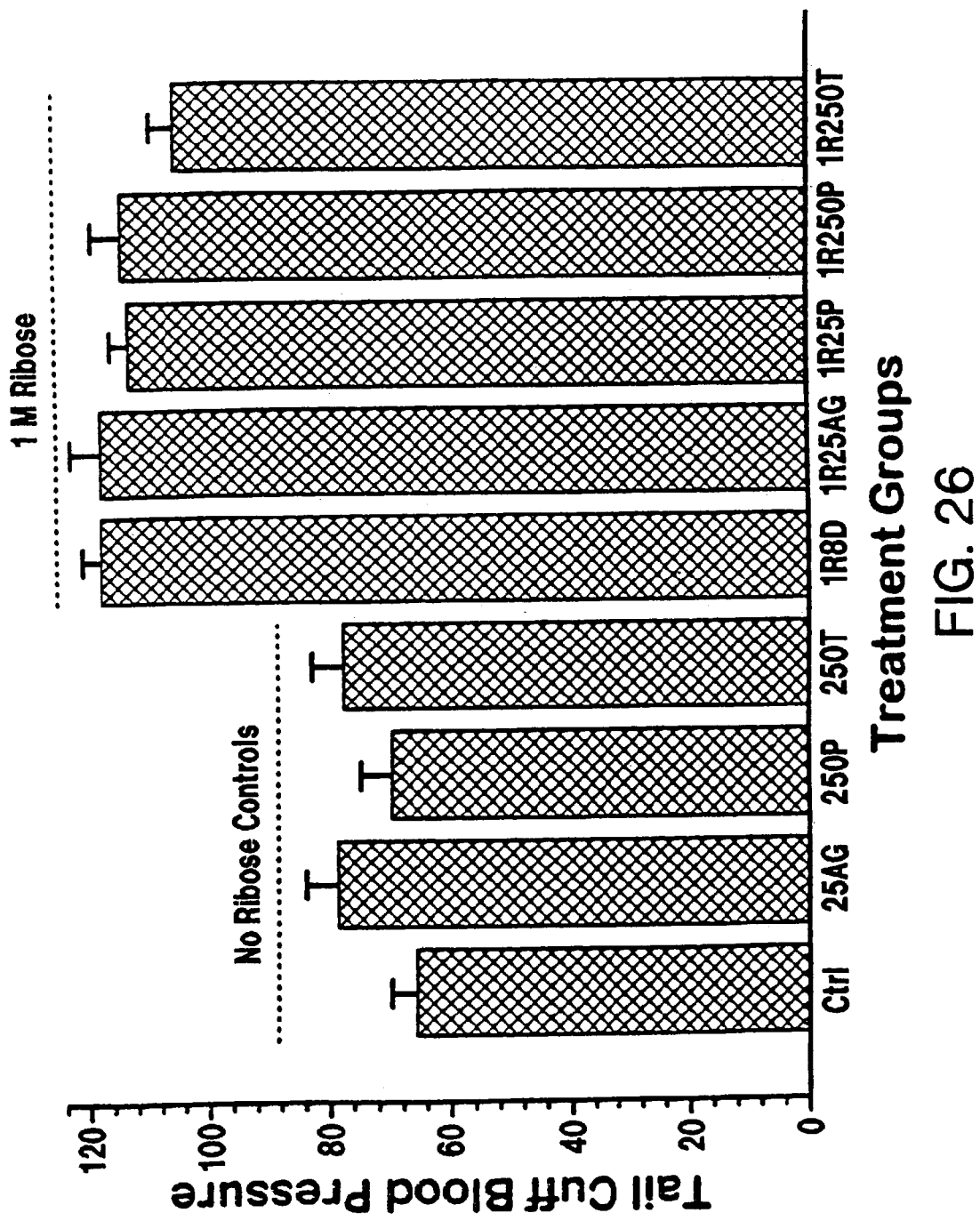
FIG. 26 is a bar graph showing the effects of inhibitor treatment in vivo, with or without ribose, on rat tail-cuff blood pressure. Treatment groups were: 25 mg/kg body weight aminoguanidine (AG); 25 or 250 mg/kg body weight Pyridoxamine (P); 250 mg/kg body weight Thiamine pyrophosphate (T), or with 1 M Ribose (R).
Figure 27:
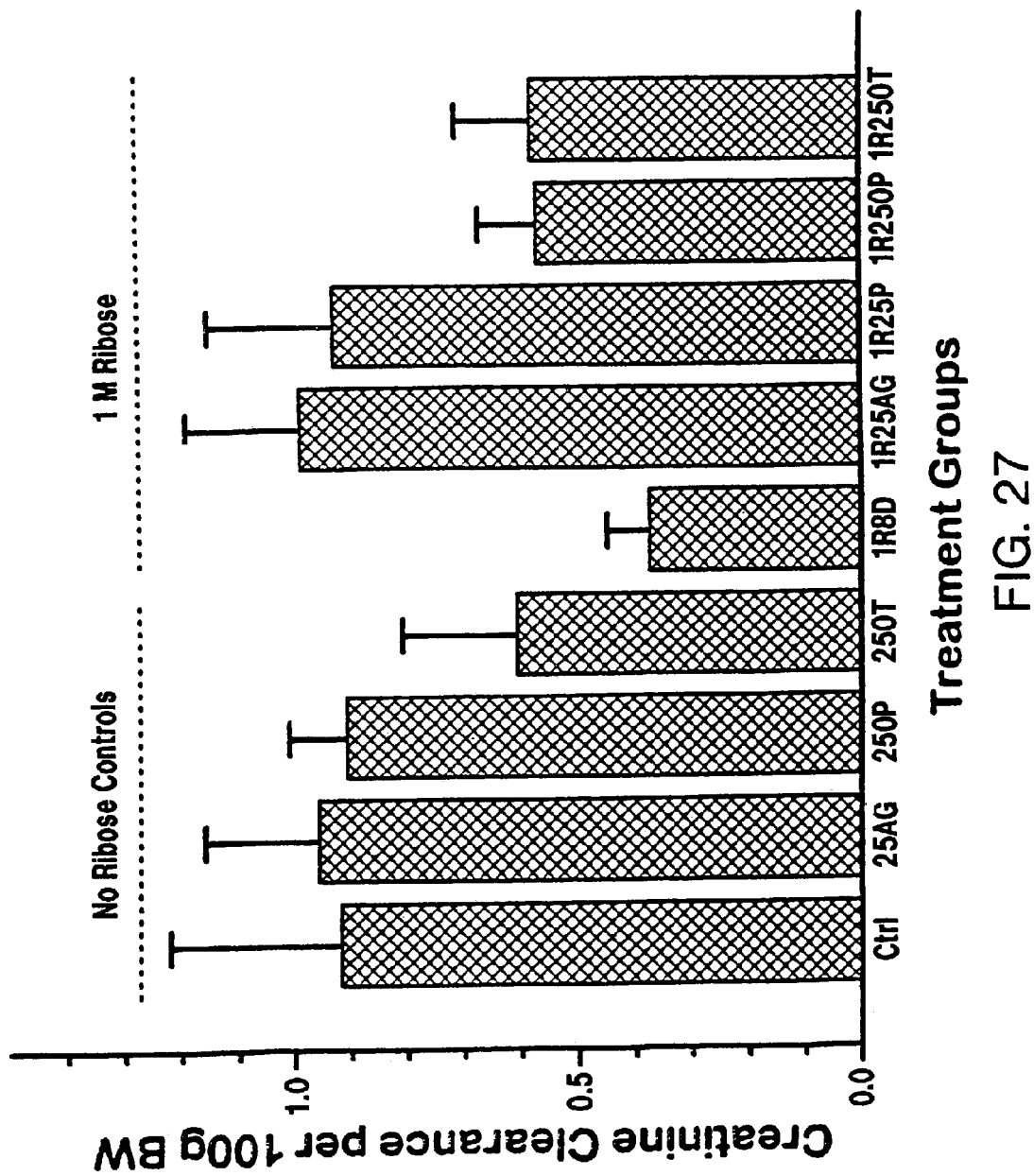
FIG. 27 is a bar graph showing the effects of inhibitor treatment in vivo, with or without ribose, on rat creatinine clearance (Clearance per 100 g body weight). Treatment groups were: 25 mg/kg body weight aminoguanidine (AG); 25 or 250 mg/kg body weight Pyridoxamine (P); 250 mg/kg body weight Thiamine pyrophosphate (T), or with 1 M Ribose (R).
Figure 28:
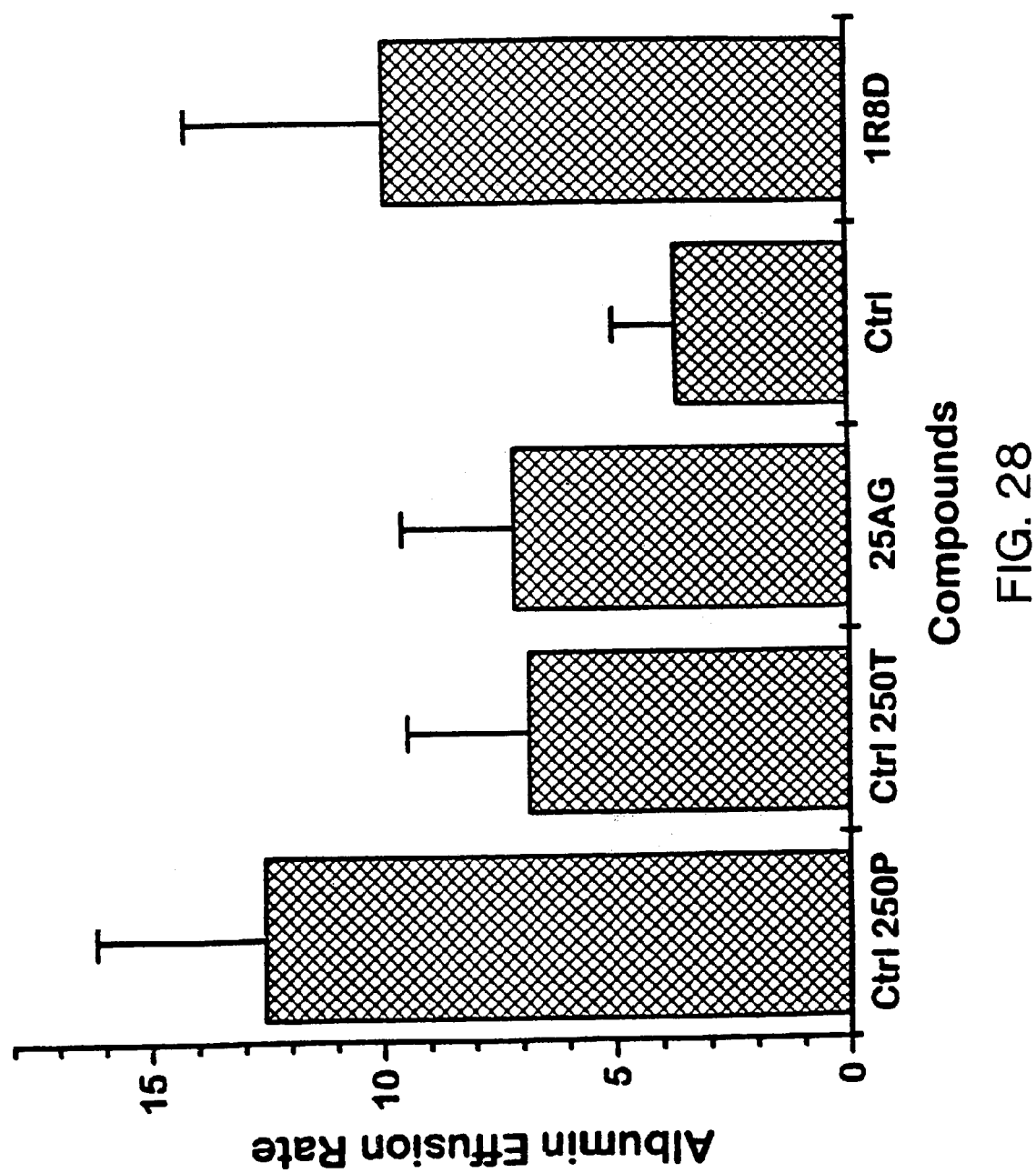
FIG. 28 is a bar graph showing the effects of inhibitor treatment in vivo without ribose, and ribose alone on rat Albuminuria (Albumin effusion rate). Treatment groups were: 25 mg/kg body weight aminoguanidine (AG); 250 mg/kg body weight Pyridoxamine (P); 250 mg/kg body weight Thiamine pyrophosphate (T), or treatment with 1 M Ribose (R) for 8 days (D). Control group had no treatment.
Figure 29:
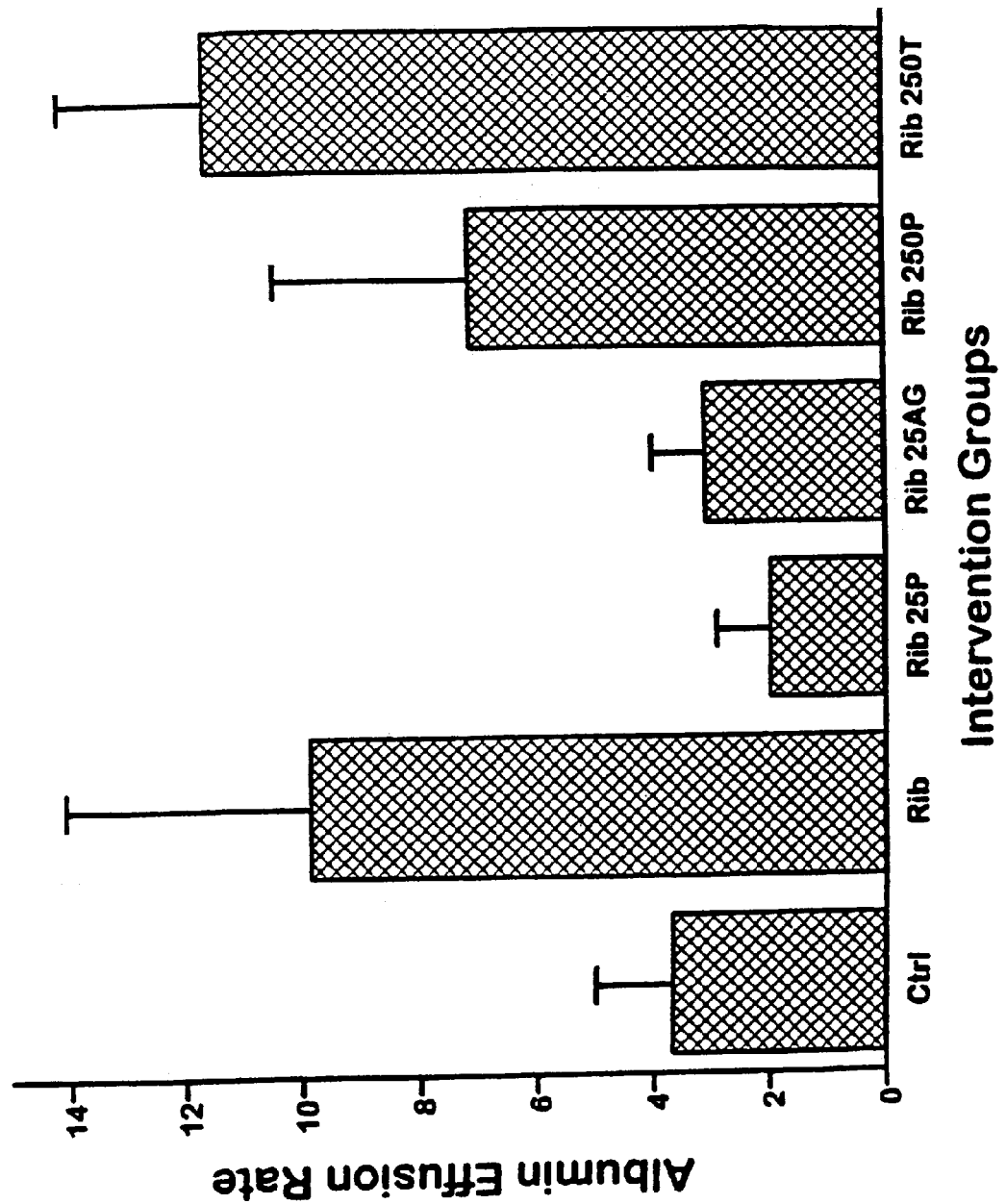
FIG. 29 is a bar graph showing the effects of inhibitor treatment in vivo, with 1 M ribose, on rat Albuminuria (Albumin effusion rate). Treatment groups were: 25 mg/kg body weight aminoguanidine (AG); 25 and 250 mg/kg body weight Pyridoxamine (P); 250 mg/kg body weight Thiamine pyrophosphate (T), or treatment with 1 M Ribose (R) for 8 days (D) alone. Control group had no treatment.
Figure 30A:
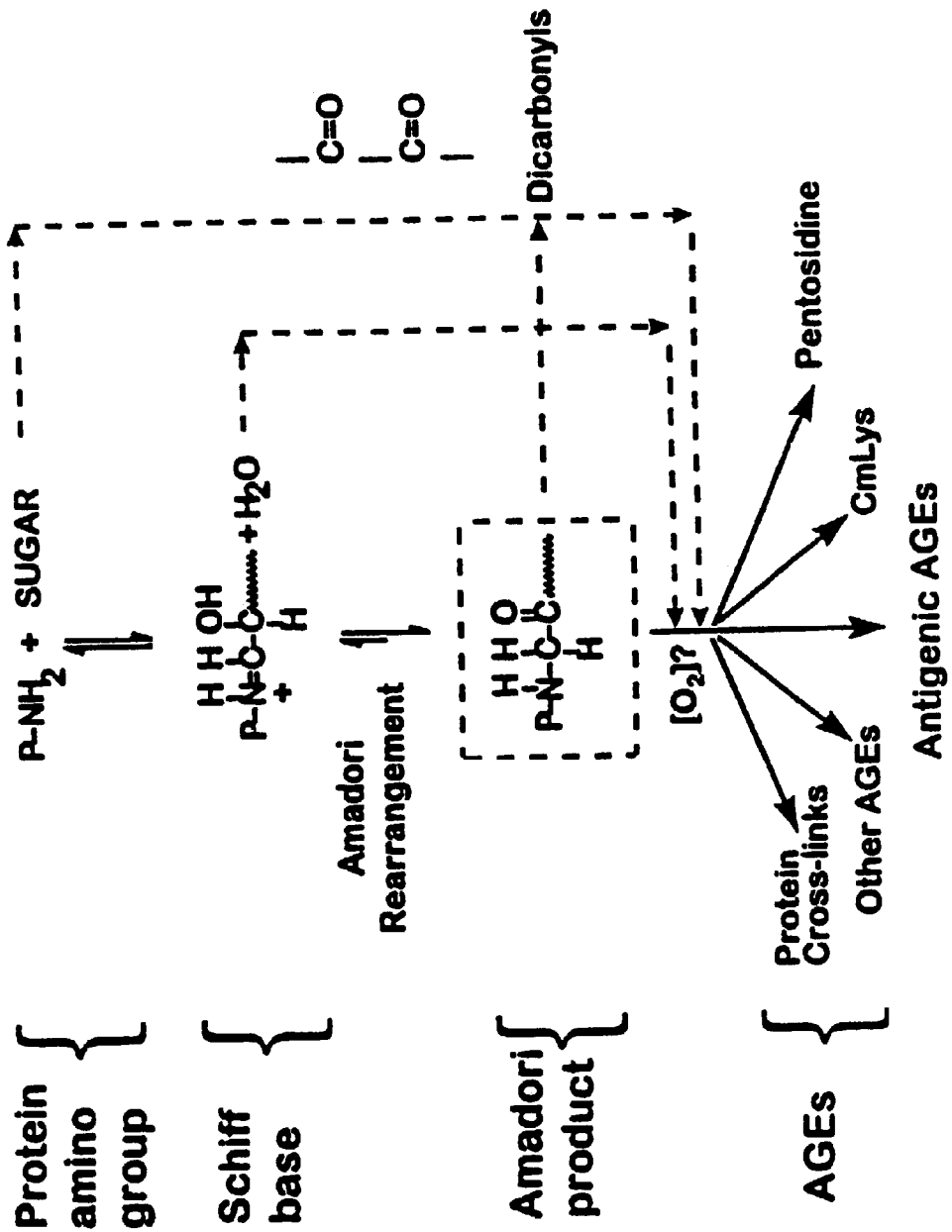
FIG. 30A depicts Scheme 1 showing a diagram of AGE formation from protein.
Figure 30B:
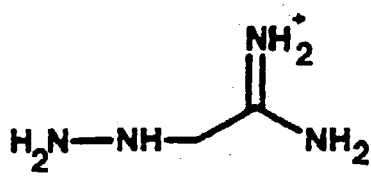
FIG. 30B depicts Scheme 2, a chemical structure of aminoguanidine.
Figure 30C:
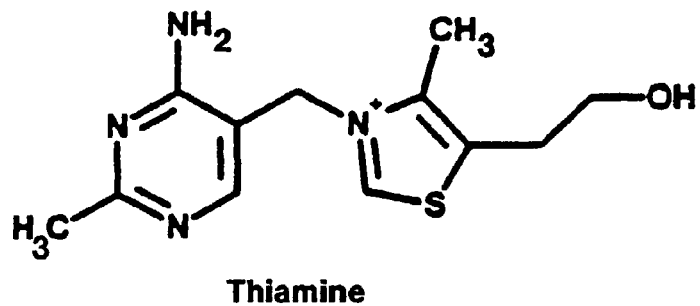
FIG. 30C depicts Scheme 3, chemical structures for thiamine, thiamine-5'-phosphate, and thiamine pyrophosphate.
Figure 30C:
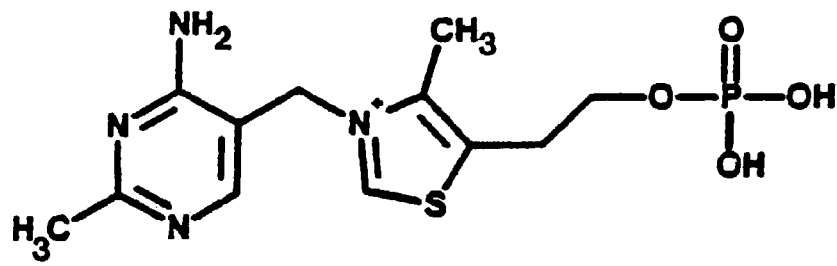
Figure 30C:
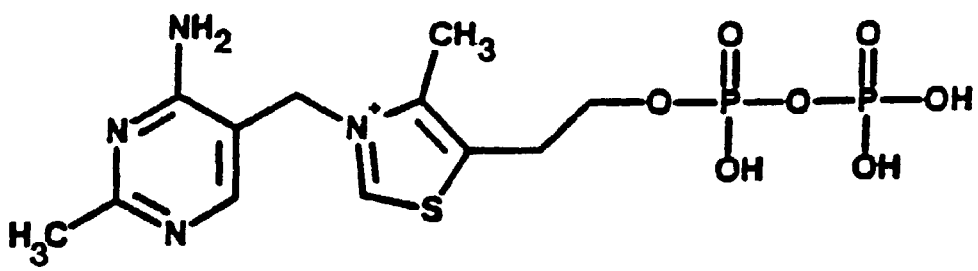
Figure 30D:
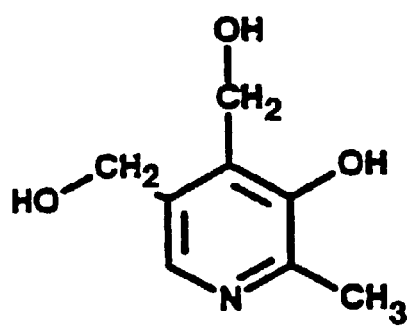
FIG. 30D depicts Scheme 4, chemical structures of pyridoxine, pyridoxamine, pyridoxal-5'-phosphate, and pyridoxal.
Figure 30D:
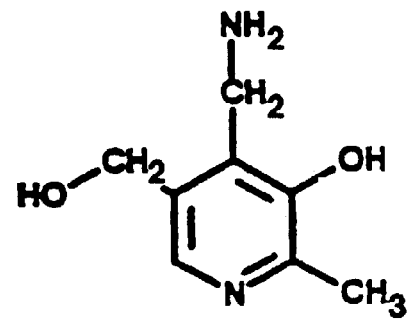
Figure 30D:
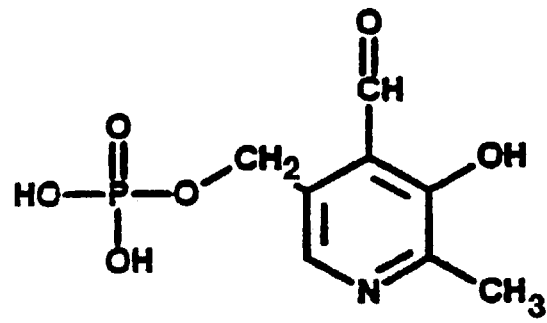
Figure 30D:
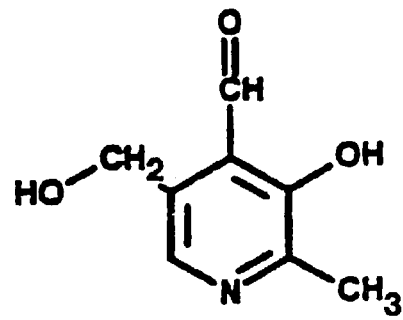

Renal Physiology Results a. Blood pressure was very slightly increased by the three compounds alone (control group); ribose-elevated BP was not ameliorated by the co-administration of compounds. These results are shown in the bar graph of FIG. 26.

b. Creatinine clearance in controls was unchanged, except for TPP which diminished it.

c. Creatinine clearance was normalized when ribose was co-administered with low dose (25 mg/kg) of either aminoguanidine or pyridoxamine. These results are shown in the bar graph of FIG. 27.

d. High concentrations (250 mg/kg) or pyridoxamine and TPP showed only partial protection against the ribose-induced decrease in creatinine clearance (FIG. 27).

e. Albumin effusion rate (AER) was elevated by ribose, as well as by high dose of pyridoxamine and TPP, and low dose of aminoguanidine in the absence of ribose. These results are shown in the bar graph of FIG. 28.

f. Albumin effusion rate was restored to normal by the co-administration of low dose of both aminoguanidine and pyridoxamine. These results are shown in the bar graph of FIG. 29.

Phase III Conclusions

As measured by two indicies of renal function, pyridoxamine and aminoguanidine, both at 25 mg/kg, were apparently effective, and equally so, in preventing the ribose-induced decrease in creatinine clearance and ribose-induced mild increase in albuminuria.

(i) Thiamine pyrophosphate was not tested at 25 mg/kg;
(ii) thiamine pyrophosphate and pyridoxamine at 250 mg/kg were partially effective in preventing creatinine clearance decreases but possibly not in preventing mild proteinuria;
(iii) at these very high concentrations and in the absence of ribose, thiamine pyrophosphate alone produced a decrease in creatinine clearance, and both produced mild increases in albuminuria.

SUMMARY

Renal Function and Diabetes

Persistent hyperglycemia in diabetes mellitus leads to diabetic nephropathy in perhaps one third of human patients. Clinically, diabetic nephropathy is defined by the presence of:

1. decrease in renal function (impaired glomerular clearance)
2. an increase in urinary protein (impaired filtration)
3. the simultaneous presence of hypertension Renal function depends on blood flow (not measured) and the glomerular clearance, which can be measured by either inulin clearance (not measured) or creatinine clearance. Glomerular permeability is measured by albumin filtration rate, but this parameter is quite variable. It is also a log-distribution function: a hundred-fold increase in albumin excretion represents only a two-fold decrease in filtration capacity.

Ribose Diabetic Rat Model

By the above criteria, ribose appears to very rapidly induce manifestations of diabetic nephropathy, as reflected in hypertension, creatinine clearance and albuminuria, even though the latter is not large. In the established STZ diabetic rat, hyperglycemia is rapidly established in 1–2 days, but clinical manifestations of diabetic nephropathy arise very late, perhaps as much as 40 weeks for albuminuria. In general, albuminuria is highly variable from day to day and from animal to animal, although unlike humans, most STZ rats do eventually develop nephropathy.

Intervention by Compounds

Using the ribose-treated animals, pyridoxamine at 25 mg/kg body weight appears to effectively prevent two of the three manifestations usually attributed to diabetes, namely the impairment of creatinine clearance and albumin filtration. It did so as effectively as aminoguanidine. The effectiveness of thiamine pyrophosphate was not manifest, but it should be emphasized that this may be due to its use at elevated concentrations of 250 mg/kg body weight. Pyridoxamine would have appeared much less effective if only the results at 250 mg/kg body weight are considered.

Effect of Compounds Alone

Overall, the rats appeared to tolerate the compounds well. Kidney weights were not remarkable and little hypertension developed. The physiological effects of the compounds were only tested at 250 mg/kg. Thiamine pyrophosphate, but not pyridoxamine, appeared to decrease creatinine clearance at this concentration. Both appeared to slightly increase albuminuria, but these measurements were perhaps the least reliable.

Human Administration

A typical adult human being of average size weighs between 66–77 Kg. Typically. diabetic patients may tend to be overweight and can be over 112 Kg. The Recommended dietary allowances for an adult male of between 66–77 Kg, as revised in 1989, called for 1.5 mg per day of thiamine, and 2.0 mg per day of Vitamin $B_6$ (Merck Manual of Diagnosis and Therapy, 16th edition (Merck & Co., Rathaway, N.J., 1992) pp 938–939).

Based upon the rat model approach, a range of doses for administration of pyridoxamine or thiamine pyrophosphate that is predicted to be effective for inhibiting post-Amadori AGE formation and thus inhibiting related pathologies would fall in the range of 1 mg/100 g body weight to 200 mg/100 g body weight. The appropriate range when co-administered with aminoguanidine will be similar. Calculated for an average adult of 75 Kg, the range (at 10 mg/1 Kg body weight) can be approximately 750 mg to upwards of 150 g (at 2 g/l Kg body weight). This will naturally vary according to the particular patient.

EXAMPLE 5

In Vivo Inhibition of the Formation of Advanced Glycation End-Products (AGES) by Derivatives of Vitamins $B_1$ and $B_6$ and Aminoguanidine. Inhibition of Diabetic Nephropathy The interrupted glycation method, as described in the examples above, allows for the rapid generation of stable well-defined protein Amadori intermediates from ribose and other pentose sugars for use in in vivo studies.

The effects of 25 mg/kg/day pyridoxamine (PM) and aminoguanidine (AG) on renal pathology induced by injecting Sprague-Dawley rats daily with 50 mg/kg/day of ribose-glycated Amadori-rat serum albumin (RSA), AGE-RSA, and unmodified RSA for 6 weeks. Hyperfiltration (increased creatinine clearance) was transiently seen with rats receiving Amadori-RSA and AGE-RSA, regardless of the presence of PM and AG.

Individuals from each group receiving Amadori-RSA and AGE-RSA exhibited microalbuminuria, but none was seen if PM was co-administered. Immunostaining with anti-RSA revealed glomerular staining in rats treated with AGE-RSA and with Amadori-RSA; and this staining was decreased by treatment with PM but not by AG treatment. A decrease in glomerular sulfated glycosaminoglycans (Alcian blue pH 1.0 stain) was also found in rats treated with glycated (Amadori and AGE) RSA. This appears to be due to reduced heparan sulfate proteoglycans (HSPG), as evidenced by diminished staining with mAb JM-403 that is specific for HSPG side-chain. These HSPG changes were ameliorated by treatment with PM, but not by AG treatment.

Thus we conclude that pyridoxamine can prevent both diabetic-like glomerular loss of heparan sulfate and glomerular deposition of glycated albumin in SD rats chronically treated with ribose-glycated albumin.

Materials and Methods

Chemicals

Rat serum albumin (RSA) (fraction V, essentially fatty acid-free 0.005%; A2018), D-ribose, pyridoxamine, and goat alkaline phosphatase-conjugated anti-rabbit IgG were all from Sigma Chemicals. Aminoguanidine hydrochloride was purchased from Aldrich Chemicals.

Preparation of Ribated RSA

Rat serum albumin was passed down an Affi-Gel Blue column (Bio-Rad), a heparin-Sepharose CL-6B column (Pharmacia) and an endotoxin-binding affinity column (Detoxigel, Pierce Scientific) to remove any possible contaminants. The purified rat serum albumin (RSA) was then dialyzed in 0.2 M phosphate buffer (pH 7.5). A portion of the RSA (20 mg/ml) was then incubated with 0.5 M ribose for 12 hours at 37° C. in the dark. After the 12 hour incubation the reaction mixture was dialyzed in cold 0.2 M sodium phosphate buffer over a 36 hour period at 4° C. (this dialysis removes not only the free ribose, but also the Schiff-base intermediaries). At this stage of the glycation process, the ribated protein is classified as Amadori-RSA and is negative for antigenic AGEs, as determined by antibodies reactive with AGE protein (as described previously; R618, antigen: glucose modified AGE-Rnase). The ribated protein is then divided into portions that will be injected either as: a)Amadori-RSA, b)NaBH$_4$-reduced Amadori-RSA, c)AGE-RSA.

The ribated protein to be injected as Amadori-RSA is simply dialyzed against cold PBS at 4° C. for 24 hours. A portion of the Amadori-RSA in 0.2 M sodium phosphate is reduced with NaBH$_4$ to form NaBH$_4$-reduced Amadori-RSA. Briefly, aliquots were reduced by adding 5 uL of NaBH$_4$ stock solution (100 mg/ml in 0.1 M NaOH) per mg of protein, incubated for 1 hour at 37° C., treated with HCl to discharge excess NaBH$_4$, and then dialyzed extensively in cold PBS at 4° C. for 36 hours. The AGE-RSA was formed by reincubating the Amadori-RSA in the absence of sugar for 3 days. The mixture was then dialyzed against cold PBS at 4° C. for 24 hours. All solutions were filtered (22 um filter) sterilized and monitored for endotoxins by a limulus amoebocyte lysate assay (E-Toxate, Sigma Chemical) and contained <0.2 ng/ml before being frozen (−70° C.) down into individual aliquots until it was time for injection.

Animal Studies

Male Sprague-Dawley rats (Sasco, 100 g) were used. After a 1 week adaptation period, rats were placed in metabolic cages to obtain a 24 hour urine specimen for 2 days before administration of injections. Rats were then divided into experimental and control groups and given tail vein injections with either saline, unmodified RSA (50 mg/kg), Amadori-RSA (50 mg/kg), NaBH$_4$-reduced Amadori-RSA (50 mg/kg), or AGE-RSA (50 mg/kg).

Rats injected with Amadori-RSA and AGE-RSA were then either left untreated, or further treated by the administration of either aminoguanidine (AG; 25 mg/kg), pyridoxamine (PM; 25 mg/kg), or a combination of AG and PM (10 mg/kg each) through the drinking water. Body weight and water intake of the rats were monitored weekly in order to adjust dosages. At the conclusion of the experimental study the rats were placed in metabolic cages to obtain 24 hour urine specimen for 2 days prior to sacrificing the animals.

Total protein in the urine samples was determined by Bio-Rad assay. Albumin in urine was determined by competitive ELISA using rabbit anti-rat serum albumin (Cappell) as primary antibody (1/2000) and goat anti-rabbit IgG (Sigma Chemical) as a secondary antibody (1/2000). Urine was tested with Multistix 8 SG (Miles Laboratories) for glucose, ketone, specific gravity, blook, pH, protein, nitrite, and leukocytes. Nothing remarkable was detected other than some protein.

Creatinine measurements were performed with a Beckman creatinine analyzer II. Blood samples were collected by heart puncture before termination and were used in the determination of creatinine clearance, blood glucose (glucose oxidase, Sigma chemical), fructosamine (nitroblue tetrazolium, Sigma chemical), and glycated Hb (columns, Pierce chemicals). Aorta, heart, both kidneys and the rat tail were. visually inspected and then quickley removed after perfusing with saline through the night ventricle of the heart. One kidney, aorta, rat tail, and the lower 2/3 of the heart were snap-frozen and then permanently stored at −70° C. The other kidney was sectioned by removing both ends (cortex) to be snap-frozen, with the remaining portions of the kidney being sectioned into thirds with two portions being placed into neutral buffered formalin and the remaining third minced and placed in 2.5% glutaraldehyde/2% paraformaldehyde.

Light Microscopy

After perfusion with saline, kidney sections were fixed in ice-cold 10% neutral buffered formalin. Paraffin-embedded tissue sections from all rat groups (n=4 per group) were processed for staining with Harris' alum hematoxylin and eosin (H&E), perodic acid/Schiff reagent (PAS), and alcian blue (pH 1.0 and pH 2.5) stains for histological examination. The alcian blue sections were scored by two investigators in a blinded fashion.

Electron Microscopy

Tissues were fixed in 2.5% glutaraldehyde/2% paraformaldehyde (0.1 M sodium cacodylate, pH 7.4), post-fixed for 1 hour in buffered osmium tetroxide (1.0%), prestained in 0.5% uranyl acetate for 1 hour and embedded in Effapoxy resin. Ultrathin sections were examined by electron microscopy.

Immunofluorescence

Parrafin-embedded sections were deparaffinized and then blocked with 10% goat serum in PBS for 30 min at room temperature. The sections were then incubated for 2 hour at 37° C. with primary antibody, either affinity purified polyclonal rabbit anti-AGE antibody, or a polyclonal sheep anti-rat serum albumin antibody (Cappell). The sections were then rinsed for 30 min with PBS and incubated with secondary antibody, either affinity purified FITC-goat anti-rabbit IgG (H+L) double stain grade (Zymed) or a Rhodamine-rabbit anti-sheep IgG (whole) (Cappell) for 1 hour at 37° C. The sections were then rinsed for 30 min with PBS in the dark mounted in aqueous mounting media for immunocytochemistry (Biomeda), and cover slipped. Sections were scored in a blinded fashion. Kidney sections were evaluated by the number and intensity of glomerular staining in 5 regions around the periphery of the kidney. Scores were normalized for the immunofluorescent score per 100 glomeruli with a scoring system of 0–3.

Preparation of Polyclonal Antibodies to AGE-Proteins

Immunogen was prepared by glycation of BSA (R479 antibodies) or Rnase (R618 antibodies) at 1.6 g protein in 15 ml for 60–90 days using 1.5 M glucose in 0.4 M phosphate containing 0.05% sodium azide at pH 7.4 and 37° C. New Zealand white rabbit males of 8–12 weeks were immunized by subcutaneous administration of a 1 ml solution containing 1 mg/ml of glycated protein in Freund's adjuvant. The primary injection used the complete adjuvant and three boosters were made at three week intervals with Freund's incomplete adjuvant. The rabbits were bled three weeks after the last booster. The serum was collected by centrifugation of clotted whole blood. The antibodies are AGE-specific, being unreactive with either native proteins or with Amadori intermediates.

ELISA Detection of AGE Products

The general method of Engvall (21) was used to perform the ELISA. Glycated protein samples were diluted to approximately 1.5 ug/ml in 0.1 M sodium carbonate buffer of pH 9.5 to 9.7. The protein was coated overnight at room temperature onto a 96-well polystyrene plate by pippetting 200 ul of protein solution into each well (about 0.3 ug/well). After coating, the excess protein was washed from the wells with a saline solution containing 0.05% Tween-20. The wells were then blocked with 200 ul of 1% casein in carbonate buffer for 2 hours at 37° C. followed by washing. Rabbit anti-AGE antibodies were diluted at a titer of 1:350 in incubation buffer and incubated for 1 hour at 37° C., followed by washing. In order to minimize background readings, antibody R618 used to detect glycated RSA was generated by immunization against glycated Rnase. An alkaline phosphatase-conjugated antibody to rabbit IgG was then added as the secondary antibody at a titer of 1:2000 and incubated for 1 hour at 37° C., followed by washing. The p-nitrophenolate being monitored at 410 nm with a Dynatech MR4000 microplate reader.

Results

The rats in this study survived the treatments and showed no outward signs of any gross pathology. Some of the rats showed some small weight changes and tail scabbing.

Initial screening of kidney sections with PAS and H&E stains did not reveal any obvious changes, and some EM sections did not reveal any gross changes in the glomerular basement membrane (GBM). However, upon Alcian Blue staining, striking differences were discovered. Alcian blue staining is directed towards negatively charged groups in tissues and can be made selective via changes in the pH of staining. At pH 1.0 Alcian blue is selective for mucopolysaccharides, and at pH 2.5 detects glucoronic groups. Thus negative charges are detected depending upon the pH of the stain.

Figure 33:
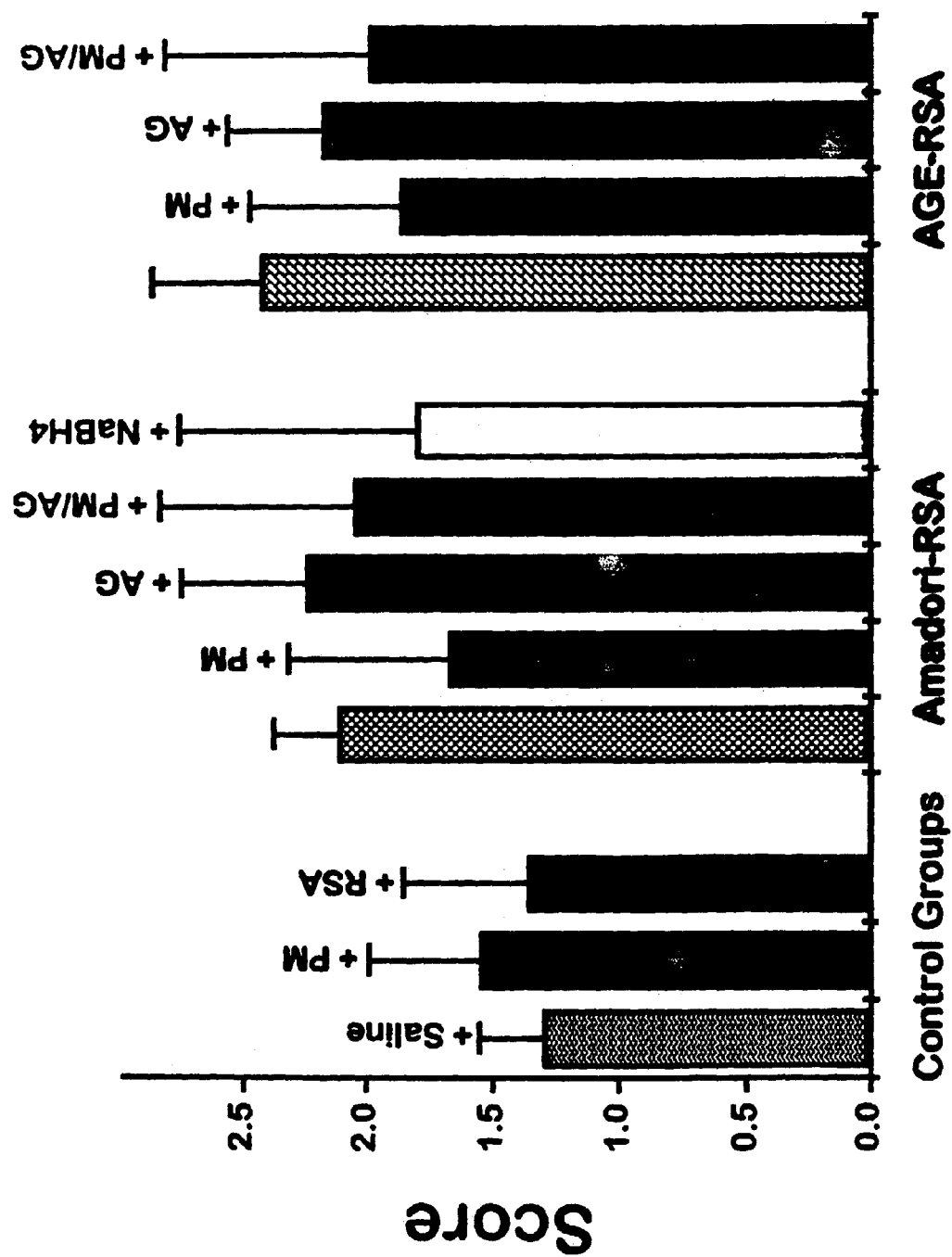
FIG. 33 is a graph showing the results of glomeruli staining at pH 2.5 with Alcian blue.

At pH 2.5 Alcian blue staining showed that Amadori-RSA (p<0.05) and AGE-RSA (p<0.01) induced increased staining for acidic glycosaminoglycans (GAG) over control levels (FIG. 33). For both AGE-RSA and Amadori-RSA, treatment with pyridoxamine (PM) prevented the increase in staining (p<0.05 as compared with controls). In contrast, treatment with aminoguanidine (AG) or combined PM and AG at 10 mg/kg each, did not prevent the increase.

Figure 34:
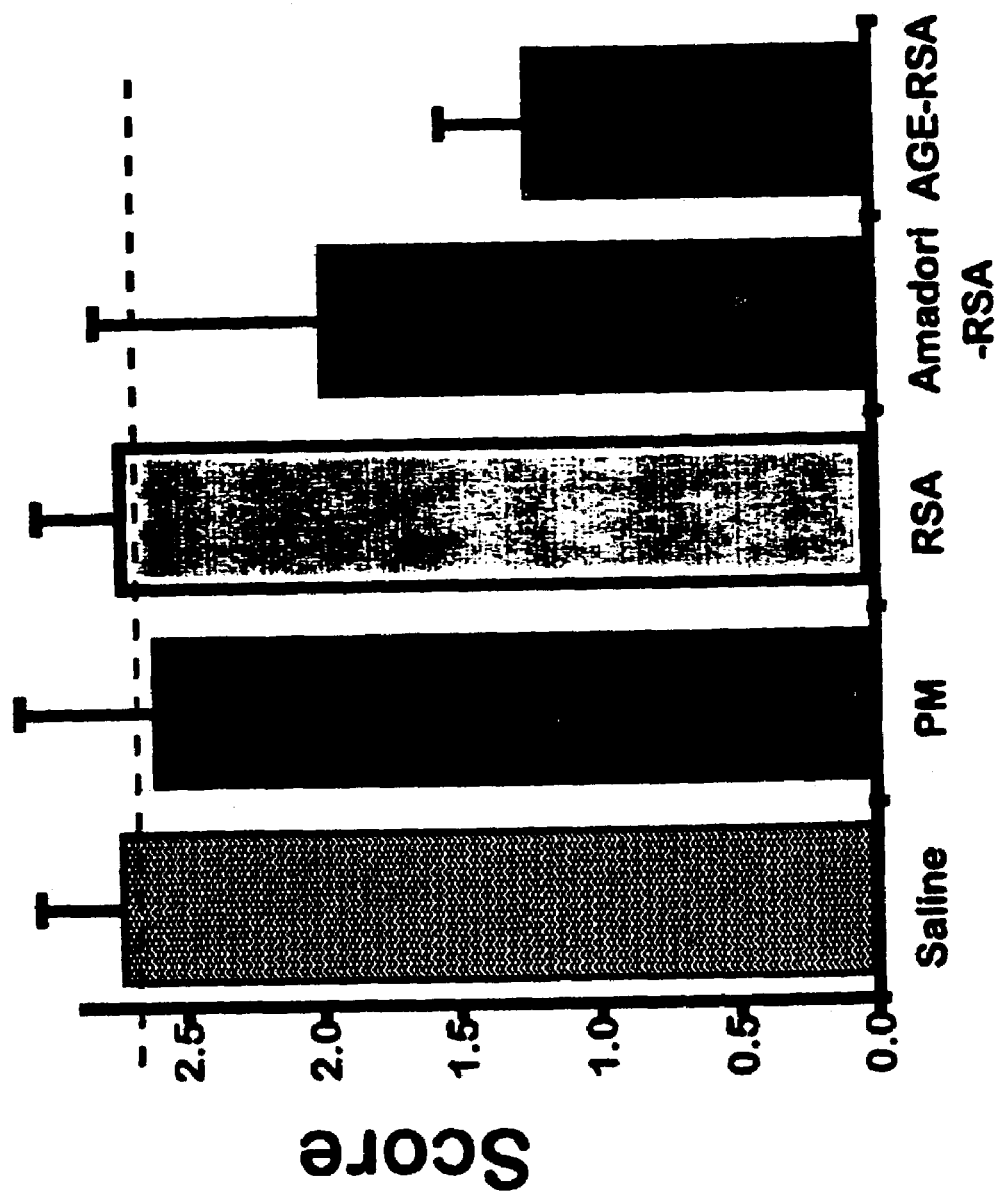
FIG. 34 is a graph showing the results of glomeruli staining at pH 1.0 with Alcian blue.

At pH 1.0 Alcian blue staining was significantly decreased by AGE-RSA (p<0.001) (FIG. 34). However, no significant difference was seen with Amadori-RSA. Due to faint staining, treatment with PM, AG and combined could not be quantitated.

Figure 35:
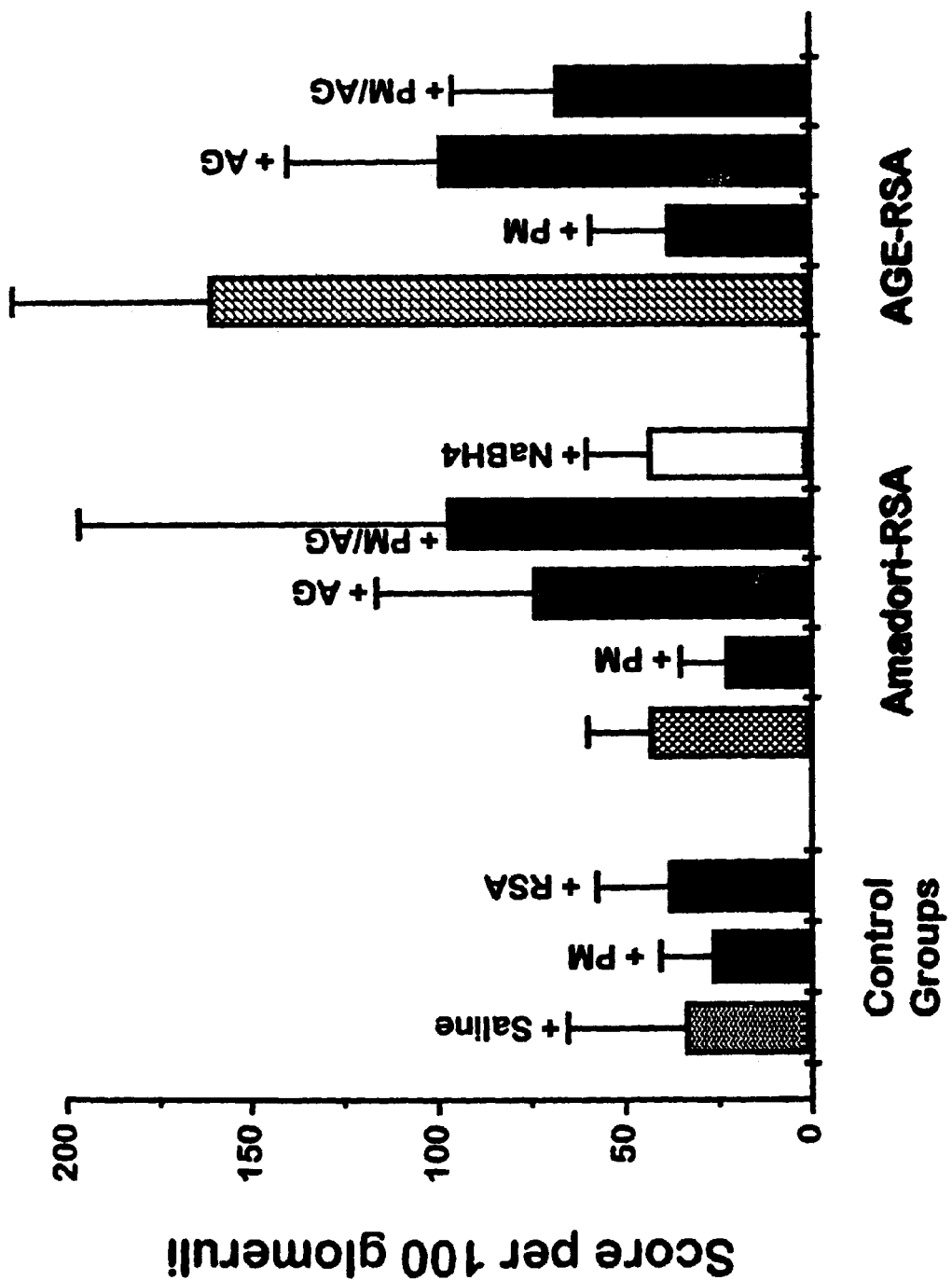
FIG. 35 is a graph showing the results of immunofluroescent glomeruli staining for RSA.

Immunofluorescent glomerular staining for RSA showed elevated staining with Amadori-RSA and AGE-RSA injected animals (FIG. 35). Significant reduction of this effect was seen in the rats treated with PM, and not with AG or combined AG & PM.

Figure 36:
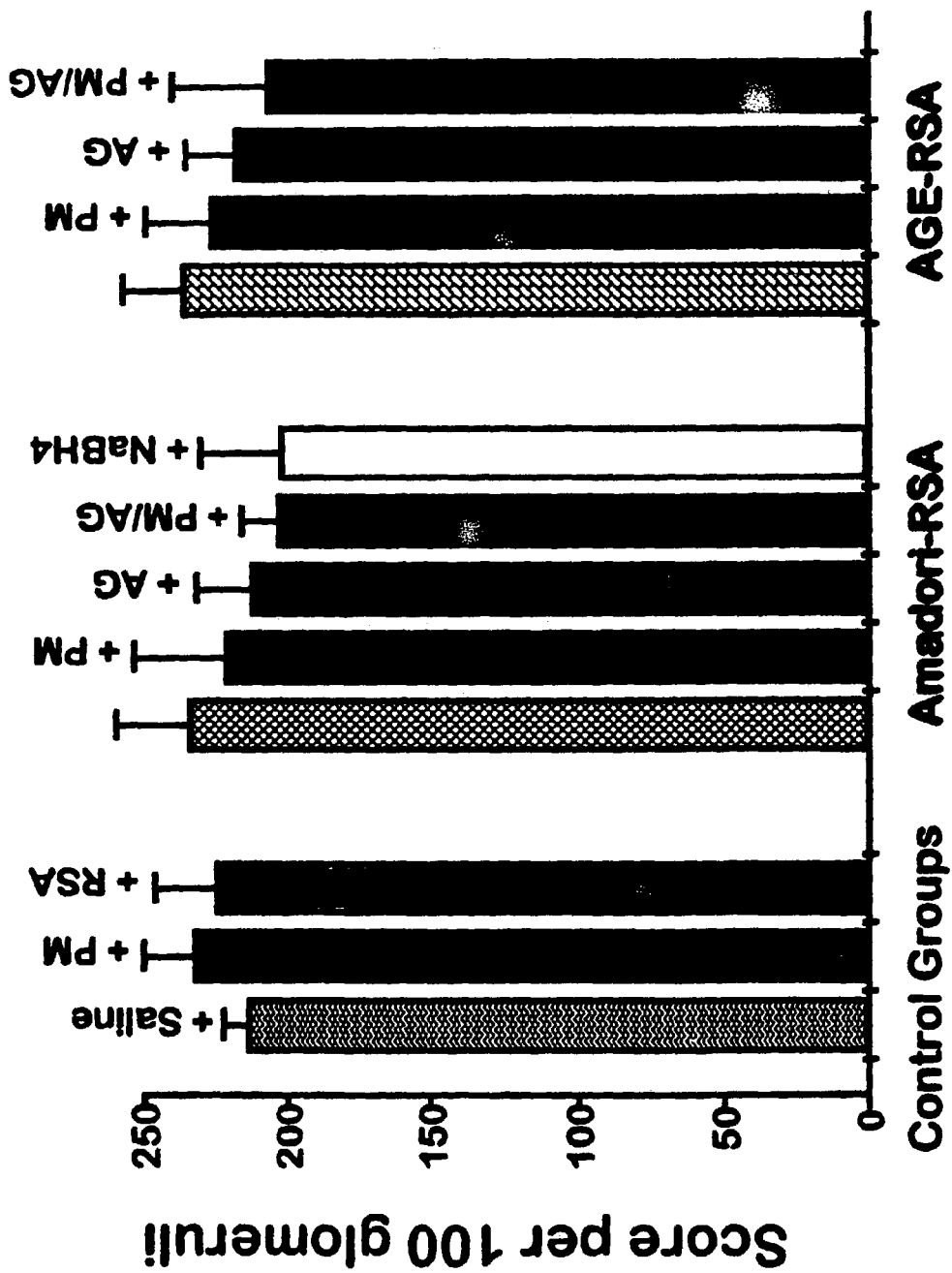
FIG. 36 is a graph showing the results of immunofluroescent glomeruli staining for Heparan Sulfate Proteoglycan Core protein.
Figure 37:
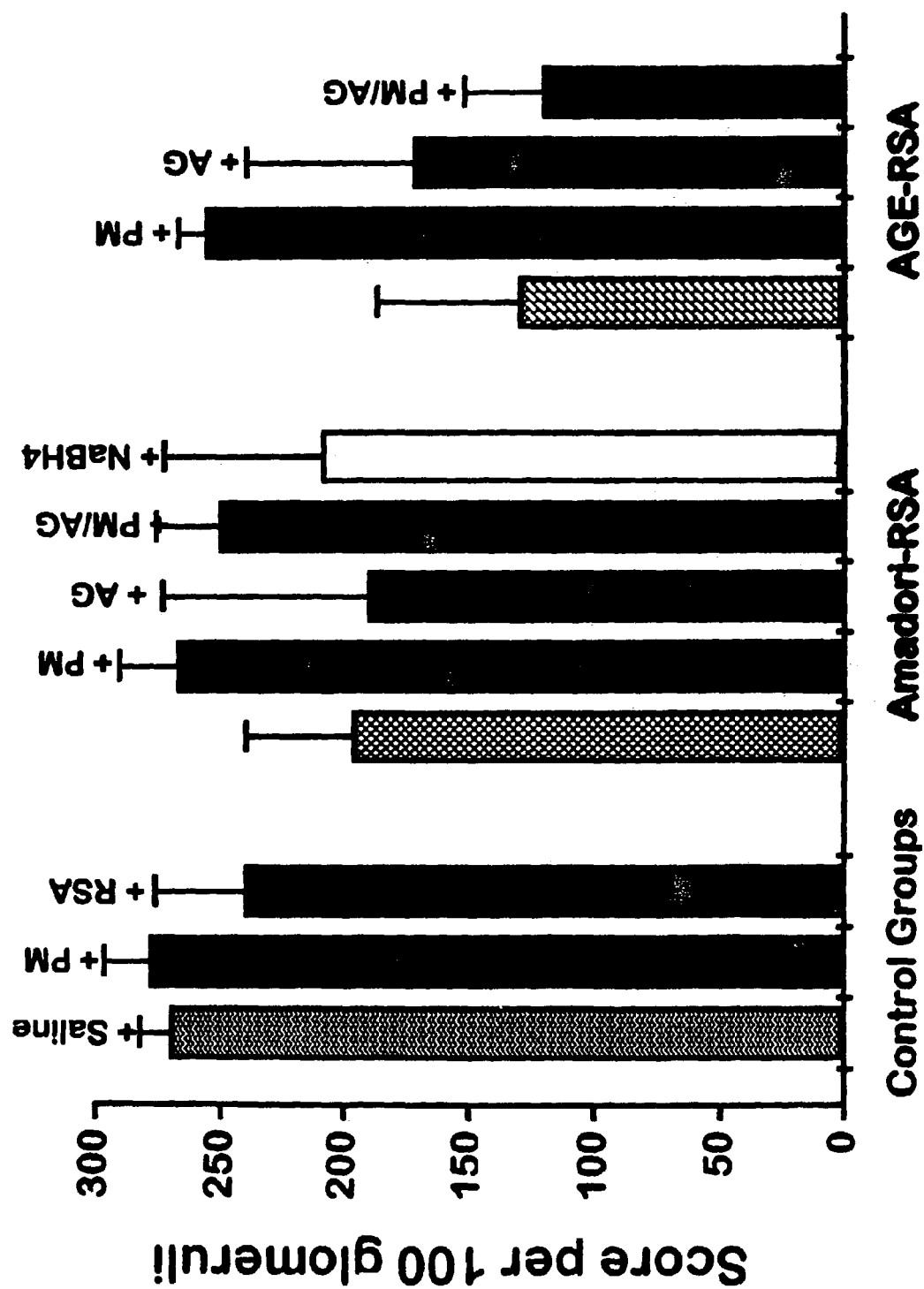
FIG. 37 is a graph showing the results of immunofluroescent glomeruli staining for Heparan Sulfate Proteoglycan side-chain.

Immunofluorescent glomerular staining for Heparan Sulfate Proteoglycan Core protein showed slightly reduced staining with Amadori-RSA and AGE-RSA injected animals but were not statistically significant(FIG. 36). A reduction of this effect was seen in the rats treated with PM, and not with AG or combined AG & PM. However, immunofluorescent glomerular staining for Heparan Sulfate Proteoglyean side-chain showed highly reduced staining with Amadori-RSA and AGE-RSA injected animals (FIG. 37) A significant reduction of this effect was seen in the rats treated with PM, and not with AG or combined AG & PM.

Figure 38:
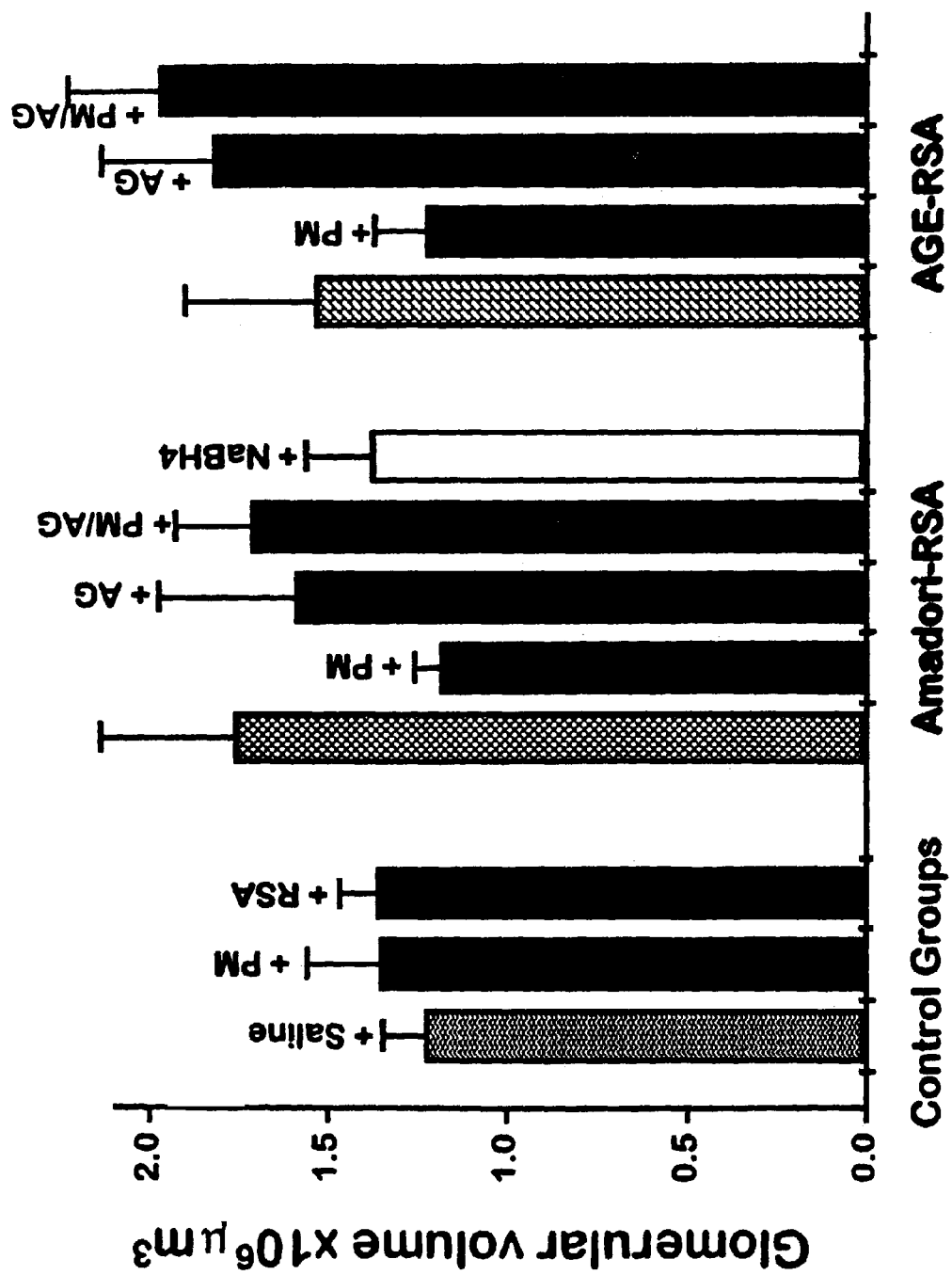
FIG. 38 is a graph showing the results of analysis of glomeruli sections for average glomerular volume.

Analysis of average glomerular volume by blinded scoring showed that Amadori-RSA and AGE-RSA caused significant increase in average glomeruli volume (FIG. 38). A significant reduction of this effect was seen with treatment of the rats with PM. No effect was seen with treatment with AG or combined AG and PM at 10 mg/kg each.

EXAMPLE 6

Inhibition of Hyperglycemia-Associated Hyperlipidemia

In an effort to inhibit the formation of AGEs and the development of diabetic nephropathy, we treated streptozotocin-induced diabetic rats with pyridoxamine. We now report that pyridoxamine inhibits the development of nephropathy in the diabetic rat, as measured by its effects on albuminuria, proteinuria and plasma creatinine; significantly corrects the dyslipidemia in diabetic rats, as measured by inhibition of the increase in plasma cholesterol and triglycerides; and corrects redox imbalances resulting from either hypoxia or pseudohypoxia, as measured by changes in the plasma lactate to pyruvate ratio. At comparable doses, pyridoxamine was more effective than the prototype AGE-inhibitor aminoguanidine in protection against diabetic nephropathy, and reversal of dyslipidemia and metabolic abnormalities of diabetes. As used herein, "diabetic mammal" encompasses both those mammals that are currently diabetic, and those that are glucose intolerant and/or have a pancreatic insufficiency, regardless of their blood sugar level. We conclude that AGE inhibitors both protect against diabetic nephropathy, and exert wide-ranging effects on lipid and carbohydrate chemistry and metabolism.

Introduction

The aim of this study was to assess the effect of PM and AG on the formation of AGEs and development of nephropathy in the diabetic rat. At the end of the 30-week experiment, we observed that the plasma from diabetic rats was visibly more lipemic than that from control rats and that there appeared to be a-decrease in lipemia in both PM- and AG-treated diabetic animals. We report that both PM and AG not only retarded the development of nephropathy in the STZ-diabetic rat, but also inhibited the increase in plasma cholesterol and triglycerides in the diabetic rats, and reversed the increase in plasma lactate and lactate/pyruvate ratio, an indicator of altered redox status in diabetes. We also discuss the origin of the increased chemical modification of collagen in the diabetic animals and the relative importance of substrate and oxidative stress, and lipids vs. carbohydrates, in formation of AGEs. Our results suggest that PM may be an effective therapeutic agent for inhibiting the development of both nephropathy and vascular disease in diabetes.

Materials and Methods

Unless otherwise indicated, reagents and enzymes were purchase from Sigma Chemical Co., St. Louis.

Experimental design. These experiments were conducted in female, Sprague-Dawley rats, made diabetic by injection of STZ. Diabetes was induced by a single tail vein injection of 45 mg/kg of STZ in 0.1 M sodium citrate buffer, pH 4.5. Control animals were sham injected with buffer only. Diabetes was confirmed by measuring blood glucose levels at 2 and 3 days after the STZ-injection. Animals with plasma glucose higher than 16 mM were classified as diabetic. The diabetic rats were divided randomly into an untreated diabetic group (n=12) and two diabetic treatment groups, receiving either PM (n=13) or AG (n=12) at 1 g/L in drinking water. Two non-diabetic control groups were included, one receiving no treatment (n=13), the other receiving $PM(HCl)_2$ at 2 g/L in drinking water (n 12); the higher dose of PM in the PM-treated control group was designed to compensate, in part, for the lower water intake of non-diabetic, compared to diabetic animals. All animals were housed individually with a light dark cycle of 12 hours each, and had free access to food and water. To maintain body weight and to limit hyperglycemia, diabetic animals received 3 IU of ultralente insulin (Humulin U, Eli Lilly) three times per week; this was increased to 5 IU after week 15 to adjust for the increase in body weight.

Nephropathy. The progression of nephropathy was assessed by monthly measurements of albumin and total protein in urine and of creatinine in plasma. For urinary measurements, rats were housed in metabolic rat cages (Nalgene, Nalge Company, Rochester, N.Y.) for 24 hours. Several drops of toluene were added to the urine collection beaker to prevent microbial growth. All assays for proteins and metabolites in plasma and urine were performed by microplate adaptations of current methods, using a Wallac Victor Model 1420 multilabel plate reader (Wallac, Inc., Gaithersburg, Md.). Control experiments showed that neither PM nor AG, at concentrations present in plasma or urine, caused interference in any of the assays, except for urinary protein (see below).

Urinary albumin was quantified by an ELISA assay. Rabbit antiserum to rat albumin and horseradish peroxidase (HRP)-conjugated goat anti-rabbit IgG were purchased from ICN Biomedical Research Products, Costa Mesa, CA. Briefly, wells were coated with 50 ng of rat albumin (Sigma, St. Louis) in 0.1 M sodium carbonate buffer, pH 10.4, overnight at 4° C. In the competition step, 100 µL of standard or diluted urine sample was incubated with 100 µL of the rabbit anti-rat albumin antiserum for 3 hours at room temperature on a microplate shaker. After washing, horseradish peroxidase-conjugated goat anti-rabbit IgG (200 µL) was applied for 1 hour at 25° C. with shaking, and the plate was developed with 200 µL of ABTS-reagent (2,2'-azinobis(3-ethylbenzthiazoline-6-sulfonic acid) for 45 minutes at room temperature, and absorbance was measured at 405 nm.

Total urinary protein was measured at the end of the experiment using Sigma Microprotein-PR Kit. Briefly, an aliquot of sample or standard was added to the reagent solution, containing pyrogallol-red and sodium molybdate, incubated for 3 minutes at 37° C., and absorbance measured at 570 nm. A correction (<10%) was applied for the PM or AG content of the sample. Plasma creatinine concentration was measured by the Jaffe picric acid procedure, using Sigma kit #555-A. Briefly, 20 µL of sample or standard were mixed with 200 µL of picrate solution. Absorbance at 490 nm was read before and after addition of the acid reagent.

Cholesterol, triglycerides free fatty acids and glycerol in plasma. Total cholesterol and triglycerides were measured by enzymatic, colorimetric, end-point assays using Sigma kits for total cholesterol (#352) and total triglycerides (#37, GPO Trinder), including the calibrators for both assays. Free fatty acids were measured as the organic soluble copper complexes, as described by Noma et al. (1973) (Noma et al. 1973. *Clin. Chim. Acta* 43:317–320). Glycerol was measured by a spectrometric enzymatic assay using glycerol kinase and glycerol 3-phosphate dehydrogenase, as described by Bergman (Bergman 1974. Assay of glycerol-phosphate dehydrogenase. In *Methods of Enzymatic Analysis, Vol. 3*. Bergman, H. V. Berlin: Verlag Chemie. 1404–1408).

Lactate, pyruvate and ketone bodies. Lactate, pyruvate and β-hydroxybutyrate were measured spectrophotometrically, using $NADH/NAD^+$ linked assays (Sigma Kits #826, 726 and 310, respectively). Acetoacetate was measured by reversal of the β-hydroxybutyrate assay using acetoacetic acid lithium salt, O-hydroxybutyrate dehydrogenase type II and NADH, as described by Li et al. (Li, et al. 1980. *Clin. Chem.* 26:1713–1717).

Renal morphometry. One side of the right kidney was cut into 2-millimeter thick slices using a set of parallel razor blades. One half of the slices were systematically selected without bias and place in formalin. These slices were dehydrated through a series of alcohols and embedded in JB-4™ (Polysciences, Inc., Warrington Pa.). From each JB-4™ block, a five-micrometer thick section was cut, stained with toluidine blue, and used for glomerular volume determination. From the non-selected slices, small blocks of cortex were fixed in 2.5% glutaraldehyde in Millonig buffer, through a series of alcohols and embedded in PolyBed 812® (Polysciences, Inc., Warrington Pa.). In order to select glomeruli without bias, one-micrometer thick sections were cut from the PolyBed 812® blocks and stained with toluidine blue. The centermost glomerulus was selected for electron microscopy. Silver-gold sections were cut using a Reichert Ultracut E ultramicrotome, placed on formvar coated slot grids and stained with uranyl acetate and lead citrate. Images were obtained using a JEOL 100CX electron microscope. Three glomeruli from each animal were used for measuring the electron microscopy parameters.

For measurement of glomerular volume, an Olympus BH-2 microscope fitted with a small mirror attached to the monocular was used to project an image onto the bench top. Fields from the JB-4™ sections were systematically selected without bias by moving the microscope stage in 2.5 mm increments. The area of all glomerular profiles within each field was measured by superimposing a grid of points over the projected image. The number of points hitting each glomerular profile was counted. The average glomerular area was calculated by the equation, Area=$(\Sigma P/\Sigma G) \times (5000/150)^2$ where $\Sigma P$ was the sum of points hitting glomerular profiles and $\Sigma G$ was the number of profiles measured, 5000 was the distance between grid points in micrometers and 150 was the magnification of the projected images. Volume was calculated by the method of Weibel and Gomez (Weibel and Gomez, 1962 *J. Appl. Physiol.* 17:343–348) using the equation Volume=$Area^{3/2} 1.38/1.01$ where 1.38 is a correction factor for spherical particles and 1.01 is a correction factor for the variation of volume among the glomeruli. An average of 65 profiles was measured for glomerular volume determination. A calibration slice was used to confirm the magnification of the projected images was 150×.

For measurement of glomerular basement membrane (GBM) width, images were systematically obtained without bias using preset positions of the microscopes stage controls. Approximately 25 percent of each glomerular profile was imaged at a final magnification of 15,000×. Glomerular basement membrane width was measured using the orthogonal intercept method (Jensen et al. 1979 *J. Microscopy* 115:19–33). An average of 169 measurements of glomerular basement membrane was made per animal. For measurement of the volume density of mesangium per glomerulus [Vv (Mes/Glom)], images were obtained and joined together to form a montage of the entire glomerular profile at a final magnification of 3900×. A grid of coarse and fine points was placed over the montage. The number of fine points falling on the mesangium and the number of coarse points falling on the glomerulus were counted (Weibel, E. R. 1979. *Practical Methods for Biological Morphometry, Stereological Methods, Vol. I*. New York, Academic Press. 332 pp.). Vv (Mes/Glom)=$\Sigma FP/(\Sigma CP \times 4)$ where $\Sigma FP$ is the number of fine points falling on mesangium and $\Sigma CP$ is the number of coarse points falling on all three glomeruli. The grid was made such that there were 4 fine points for each coarse point. An average of 174 coarse points hit glomerulus and 164 fine points hit mesangium per animal. A calibration grid was photographed at both the high and low magnification for each roll of film to determine the exact magnification of each measured image. Total mesangial volume was calculated by multiplying glomerular volume by Vv (Mes/Glom).

Statistical analysis. Statistical analyses were performed using Sigma Stat for Windows VI.00 (SPSS, Inc., Chicago, Ill.). P-values were calculated by non-parametric Mann-Whitney Rank Sum analysis. Correlation analyses were performed by the Pearson Product Moment method.

Results

Figure 39:
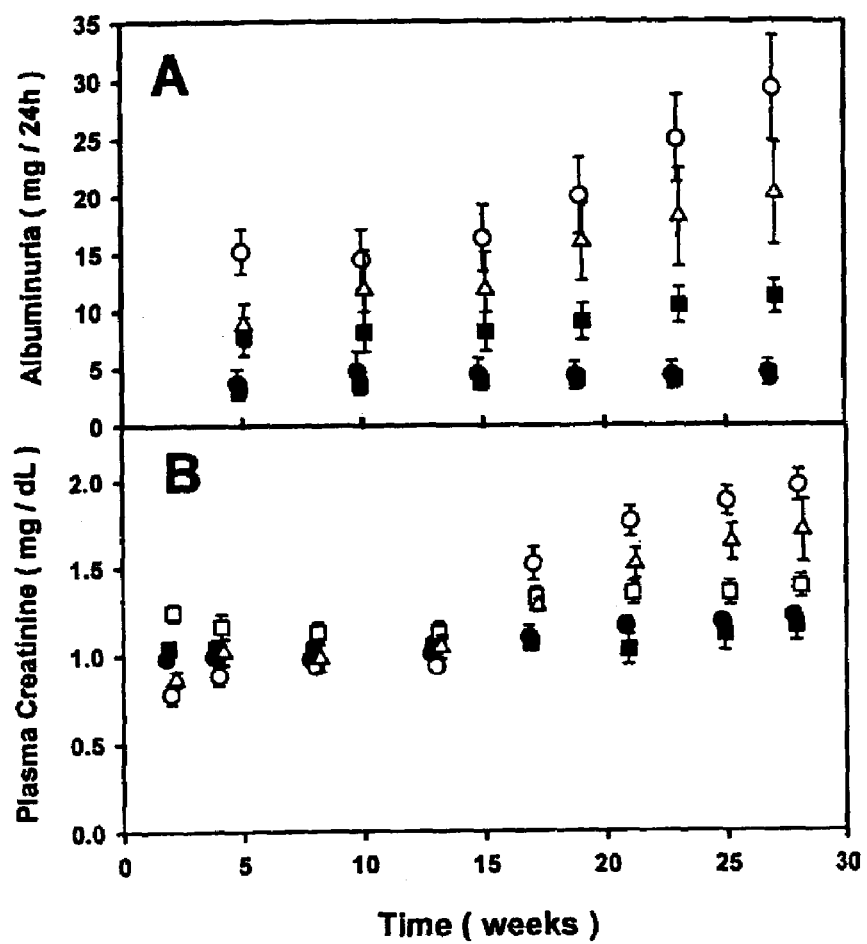
FIG. 39. Effect of AG and PM on development of nephropathy in STZ-diabetic rats. Urine (24-hour samples) and blood were collected at 4-week intervals for measurement of albuminuria (A) and plasma creatinine (B). Data are expressed as mean±SEM for non-diabetic control (●), non-diabetic control +PM (■), untreated diabetic (○), diabetic+PM (□), and diabetic+AG (Δ) groups. Proteinuria (C) was measured in a 24-hour collection at the end of the experiment (28 weeks of diabetes). Statistical summaries, determined by the Mann-Whitney Rank Sum Test: all diabetic groups vs. non-diabetic controls in A, B & C, $p \leq 0.001$. (A, albuminuria): D-PM vs. D, $p<0.0001$; D-AG vs. D, $p=0.05$; D-PM vs. D-AG, $p<0.01$. (B, creatininemia): D-PM vs. D, $p<0.0001$; D-AG vs. D, $p<0.05$; D-PM vs. D-AG, $p=0.02$. (C, proteinuria): D-PM vs. D, $p<0.001$; D-AG vs. D, $p<0.01$; D-PM vs. D-AG, NS.
Figure 39:
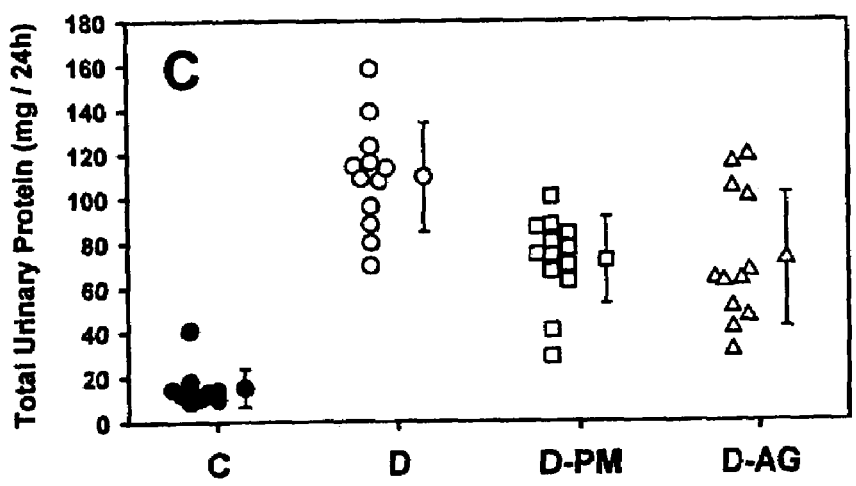

Progression of nephropathy. Urinary albumin and protein excretion, and plasma creatinine concentrations were used as measures of diabetic nephropathy (FIG. 39). PM-treated non-diabetic controls were indistinguishable from untreated, non-diabetic controls throughout the experiment, however albuminuria increased with time in all diabetic groups, with untreated diabetic animals showing the greatest increases in albuminuria. At 23 weeks of diabetes, all three diabetic groups were significantly different from one another, and from non-diabetic controls, with respect to albuminuria (FIG. 39A). PM provided significantly greater protection against albuminuria than AG. As shown in FIG. 39B, plasma creatinine values also began to rise above normal at about the 17$^{th}$ week. As observed with albuminuria and proteinuria, both PM and AG also blunted the rise in plasma creatinine, although PM was significantly more effective than AG. Effects on albuminuria were mirrored by differences in proteinuria, measured at the end of the experiment (FIG. 39C), although albuminuria appeared to be the more sensitive indicator of nephropathy.

Figure 40:
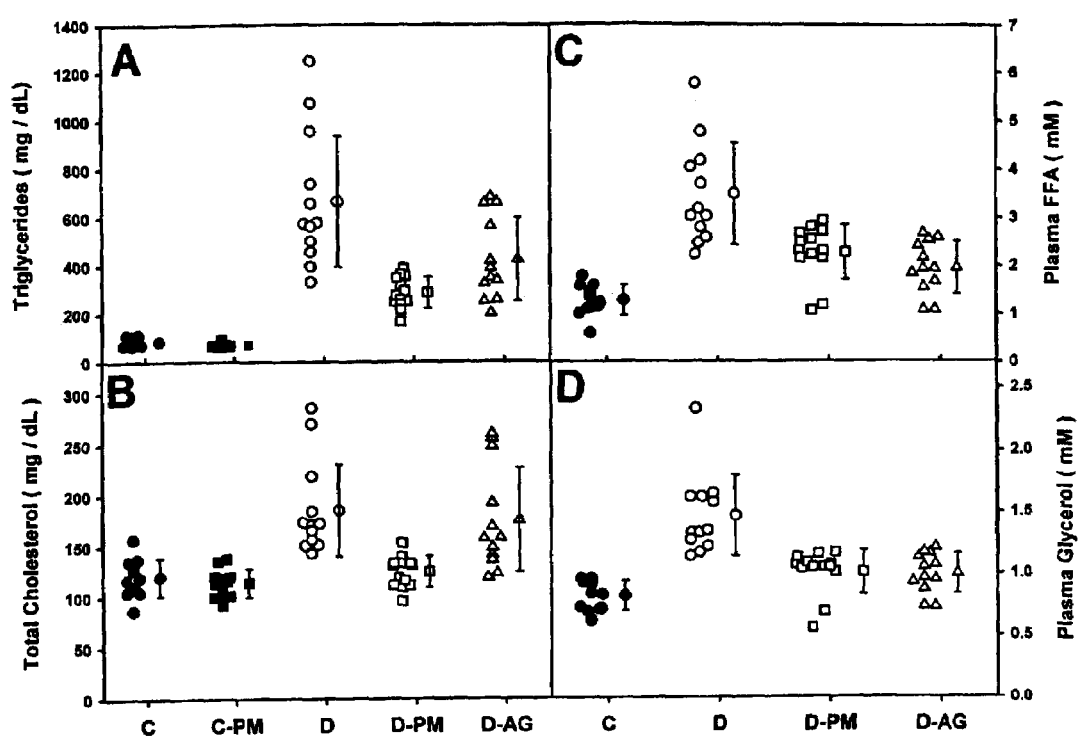
FIG. 40. Effect of AG and PM on dyslipidemia in STZ-diabetic rats. Plasma obtained at the end of the experiment (28 weeks) was analyzed for triglyceride (A), total cholesterol (B), free fatty acids (C) and glycerol (D). Data are mean±SD for non-diabetic control (●), non-diabetic control+PM (■), untreated diabetic group (○), diabetic+PM group (□), and diabetic+AG group (Δ). Statistical analysis was performed by the Mann-Whitney Rank Sum test: all diabetic groups vs. non-diabetic controls in A, B, C & D, $p<0.001$. (A): D-PM vs. D, $p=0.0001$; D-AG vs. D, $p<0.05$; D-PM vs. D-AG, $p<0.01$. (B): D-PM vs. D: D-AG vs. D, NS; D-PM vs. D-AG, $p<0.01$. (C): D-PM vs. D, $p=0.002$; D-AG vs. D, $p<0.001$; D-PM vs. D-AG, NS. (D): D vs. C, $p<0.0001$; D-PM vs. D, $p<0.0001$; D-AG vs. D, $p<0.0001$; D-PM vs. D-AG, NS.

Dyslipidemia. At necropsy we observed that the blood of untreated diabetic animals was visibly more lipemic than blood from control and PM- or AG-treated animals. Assays of plasma lipids (FIG. 40) documented a substantial increase in lipemia in untreated diabetic animals, and substantial correction of hyperlipidemia by both PM and AG. Triglycerides (FIG. 40A) increased to a mean of ~700 mg/dL in diabetic rats, compared to 100 mg/dL in non-diabetic controls, and were reduced to means of 220 and 350 mg/dL by PM and AG, respectively. Plasma cholesterol (FIG. 40B) was increased by ~50% and was normalized by PM and partially corrected by AG. Although the increase in lipemia might be attributed to decreased uptake of low density lipoprotein in peripheral tissues because of a defect in lipoprotein lipase activity in diabetes, there was also an indication of increased lipolysis, based on increases in both free fatty acids and glycerol in plasma. As shown in FIGS. 40C and 40D, plasma free fatty acid and glycerol concentrations were increased by 2–3 fold in diabetic rats and were approximately 50% normalized by treatment with either PM or AG.

Figure 41:
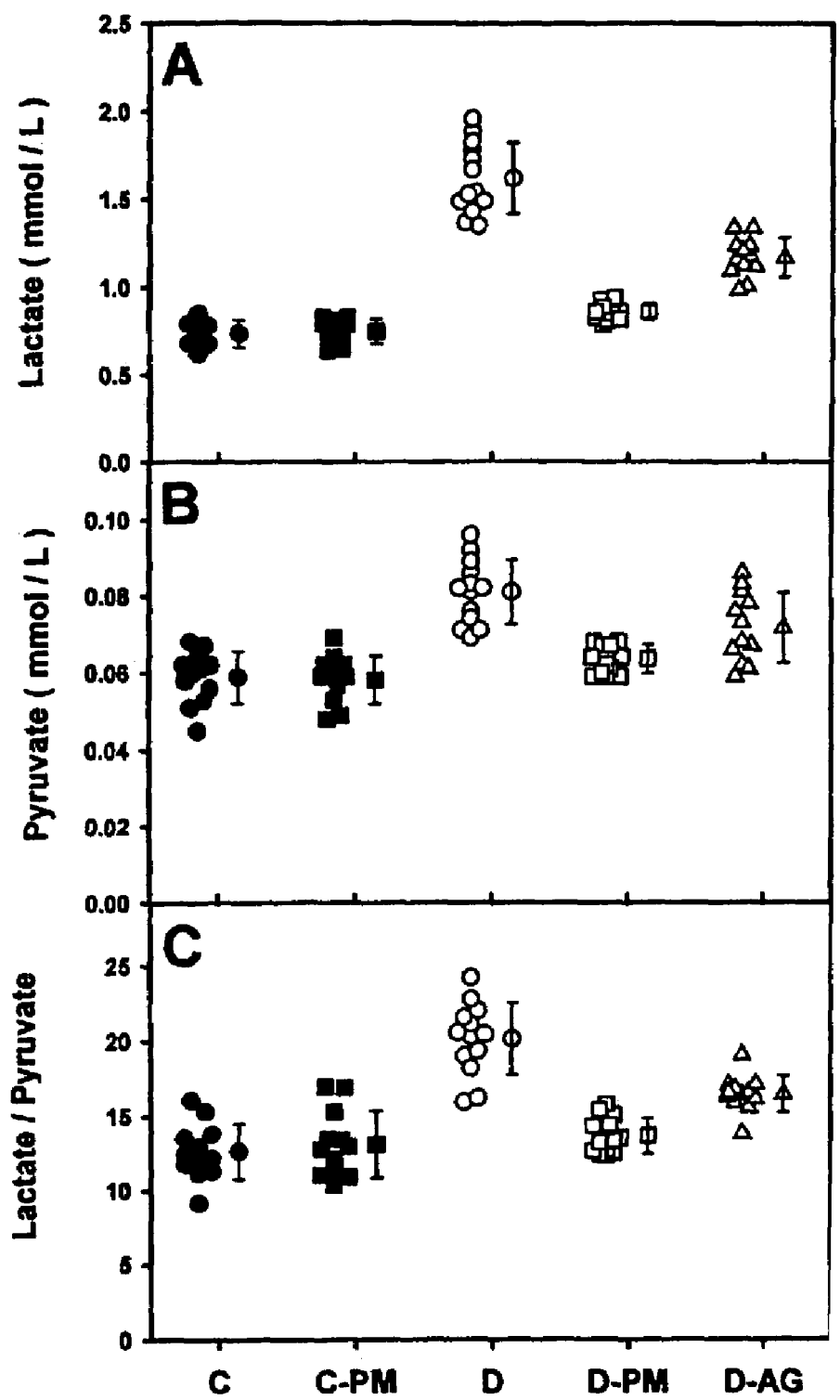
FIG. 41. Effect of AG and PM on redox imbalances in STZ-diabetic rats. Plasma obtained at the end of the experiment (28 weeks) was analyzed for lactate (A) and pyruvate (B) concentrations. Their ratio of lactate/pyruvate, an index of redox status, is shown in frame (C). Symbols are defined in legend to FIG. 2. Statistical analysis was performed by the Mann-Whitney Rank Sum test. (C, lactate/pyruvate): D vs. C, $p<0.0001$; D-PM vs. D, $p<0.001$; D-AG vs. D, $p=0.002$; D-PM vs D-AG, $p<0.01$.

Redox imbalances. Alterations in lipid metabolism may result from glucose-induced redox imbalances (pseudohypoxia) (Williamson et al. 1993, *Diabetes* 42:801–813) or decreased tissue oxygenation (Mayrovitz, and Larsen, 1996. *Microvasc. Res.* 52:115–126; Tesfaye et al. 1994. *Diabetologia* 37:847–854) (true hypoxia) in diabetes. These changes are reflected by a change in the cytosolic ratio of NADHI-NAD$^+$, which can be assessed indirectly by measuring the ratio of lactate to pyruvate in plasma. As shown in FIG. 41, diabetic animals had significantly higher levels of both lactate and pyruvate in plasma, as well an increased lactate/pyruvate ratio. PM, and to a lesser extent AG, partially corrected these deficits in oxidative metabolism of carbohydrates. We also measured plasma β-hydroxybutyrate and acetoacetate concentrations. sometimes used as an indicator of mitochondrial redox status. Concentrations of these metabolites varied greatly among the animals. While there were clear trends toward an increase in β-hydroxybutyrate and acetoacetate in diabetic animals and an indication that both PM and AG corrected these changes, the differences did not reach statistical significance.

Anatomical observations. As shown in Table 1, mean kidney and liver weights were increased in diabetic rats, both in absolute terms and as a fraction of total body mass. These changes in tissue weight were partially reversed by PM and AG. Occasional cysts were observed in kidneys of diabetic animals, but were not increased in drug-treated groups. There was no evidence of an increase in tumors in major organs, nor of other unusual pathologies associated with either PM or AG therapy. Significant changes in renal morphology were observable within the seven months' duration of diabetes in the rat, including a 30% increase in glomerular basement membrane (GBM) thickness, 60% increase in glomerular volume, 25% increase in mesangial volume fraction, and 100% increase in mesangial volume (Table 2). PM caused a significant, but partial correction of the increase in glomerular volume, and there was a trend toward reduction in GBM thickness and mesangial volume by PM. The increase in mesangial volume fraction in PM-treated rats might have resulted from a disproportionate decrease in glomerular volume in PM-treated animals. The effects of AG on these parameters were not evaluated.

TABLE 1

Effects of diabetes and drug treatment on liver and kidney weight.

| Group | Kidney (g) | Kidney (g/100 g) | Liver (g) | Liver (g/100 g) |
|---|---|---|---|---|
| Control | 0.84 ± 0.04 | 0.32 ± 0.02 | 7.96 ± 0.5 | 3.37 ± 0.22 |
| Untreated Diabetic | 1.53 ± 0.21 | 0.73 ± 0.23 | 16.7 ± 3.4 | 7.03 ± 0.94 |
| Diabetic + PM | 1.25 ± 0.30 | 0.59 ± 0.05 | 12.8 ± 2.1 | 6.00 ± 0.59 |
| Diabetic + AG | 1.31 ± 0.18 | 0.59 ± 0.07 | 14.0 ± 2.6 | 6.20 ± 0.99 |
| p-value: D + PM vs. D | NS | <0.001 | =0.0025 | =0.002 |
| p-value: D + AG vs. D | | =0.002 | <0.05 | >0.05 |

TABLE 2

Effect of diabetes and drug treatment on renal morphometry[A]

| Group | GBM width | Glomerular Volume | Mesangial Volume Fraction | Mesangial Volume |
|---|---|---|---|---|
| Non-diabetic (n = 12) | 201 ± 14.9[B] | 1.30 ± 0.10[B] | 0.19 ± 0.03[C] | 0.25 ± 0.05[B] |
| Diabetic (n = 13) | 229 ± 19.4 | 2.08 ± 0.27 | 0.24 ± 0.06 | 0.52 ± 0.22 |
| Diabetic + PM (n = 13) | 225 ± 25.1 | 1.68 ± 0.08[C] | 0.27 ± 0.06 | 0.46 ± 0.12 |

[A]Glomerular basement membrane width and mesangial volume fractions were measured by electron microscopy and glomerular and mesangial volumes by light micrsocopy, as described in Materials and Methods.
[B]$p < 0.001$ vs. untreated diabetic animals.
[C]$p < 0.025$ vs. untreated diabetic animals.

Figure 42:
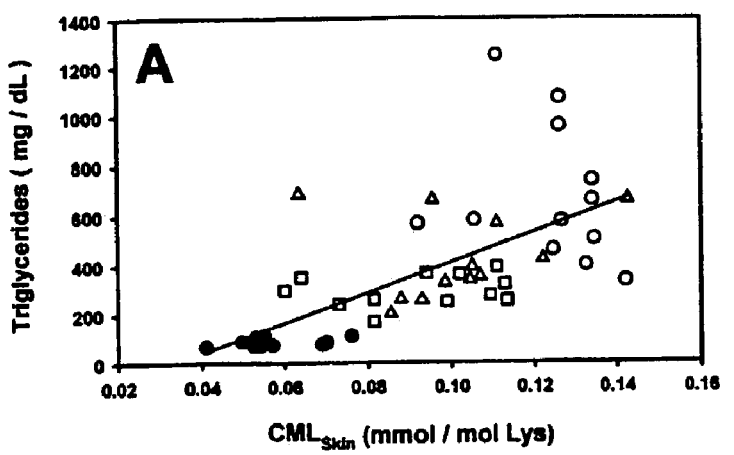
FIG. 42. Correlations between AGEs in skin collagen and -biochemical and physiological parameters. Correlation are shown between CML and plasma triglycerides (A), urinary albumin and plasma triglyceride concentrations (B), and CML and urinary albumin concentration (C). Statistical analysis was performed by Pearson Product Moment calculations. Symbols are defined in legend to FIG. 2. Correlation coefficients and p-values are summarized in Table 3.
Figure 42:
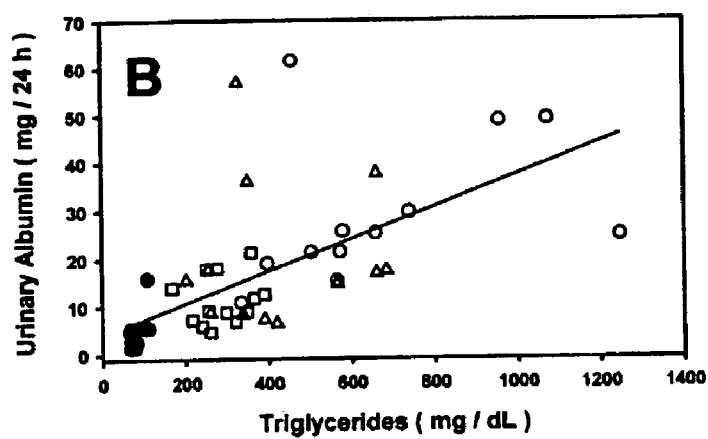
Figure 42:
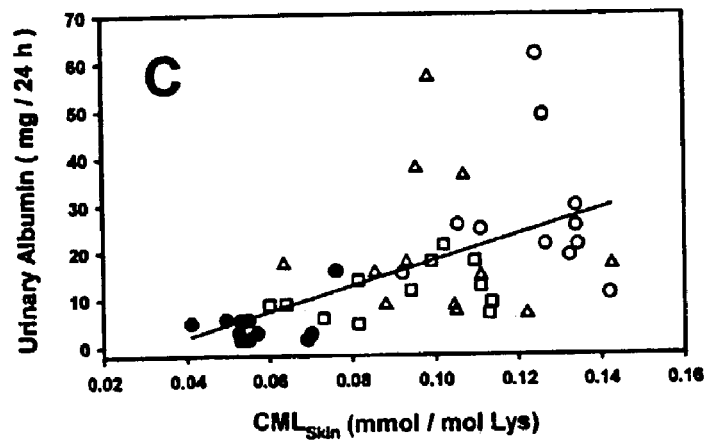

Relationship among biochemical parameters and AGEs. Because lipids were significantly increased in the diabetic rats and also lowered by PM and AG, and because lipids are recognized as sources of CML (13), CEL (14) and fluorescent products, e.g. in lipofuscin, and crosslink structures (except for pentosidine) in tissue proteins, we examined the relationship between plasma lipids, diabetic nephropathy and chemical modification of proteins in the diabetic rat. As shown in FIG. 42, there was a strong correlation between CML in skin collagen and plasma triglycerides, and both CML and triglycerides also correlated with microalbuminuria. Other correlations are summarized in Table 3. None of these measures correlated with glycemia or protein glycation, since these parameters were unaffected or, in the case of glycation of collagen, only slightly affected by drug therapy.

diabetic rats. These therapeutic effects were achieved without significant changes in glycemia or glycated hemoglobin in the diabetic rats.

All diabetic animals exhibited characteristic changes in renal structure, including renal hypertrophy (Table 1), accelerated thickening of glomerular basement membranes (GBM), increased glomerular volume and mesangial expansion (Table 2). Although PM (and AG) partially inhibited the gain in kidney weight, PM had limited effects on the ultrastructural changes in the kidney (Table 2). Effects of AG on renal morphology were not measured in this study, but other studies on AG treatment of the STZ-diabetic rat have yielded mixed results. One study reported inhibition of GBM thickening in the Lewis rat (Ellis and Good, 1991. *Metabolism* 40:1016–1019), while there are two reports that AG had no effect on GBM thickening in Sprague Dawley

TABLE 3

Relationships among various markers of oxidative stress, lipemia and renal function.[A]

| | CML Skin (n = 48) | Urinary Albumin (n = 49) | Plasma Creatinine (n = 49) | Plasma Triglycerides (n = 50) | Plasma Cholesterol (n = 50) |
|---|---|---|---|---|---|
| Urinary Albumin | $p < 0.0001$<br>$r = 0.54$ | — | | | |
| Plasma Creatinine | $p < 0.0001$<br>$r = 0.65$ | $p < 0.0001$<br>$r = 0.55$ | — | | |
| Plasma Triglycerides | $p < 0.0001$<br>$r = 0.66$ | $p < 0.0001$<br>$r = 0.62$ | $p < 0.0001$<br>$r = 0.56$ | — | |
| Plasma Cholesterol | $p = 0.001$<br>$r = 0.46$ | $p = 0.0001$<br>$r = 0.82$ | $p = 0.0013$<br>$r = 0.45$ | $p < 0.0001$<br>$r = 0.71$ | — |
| Urinary Protein (n = 29) | $p < 0.0001$<br>$r = 0.73$ | $p < 0.0001$<br>$r = 0.77$ | $p < 0.0001$<br>$r = 0.61$ | $p < 0.0001$<br>$r = 0.80$ | $p < 0.0001$<br>$r = 0.74$ |

[A]Statistics derived from Pearson Product Moment calculation.

Discussion

Effect of pyridoxamine on diabetic nephropathy. These studies were designed to evaluate the effectiveness of PM on the formation of AGEs and development of nephropathy in STZ-diabetic rats. In the present report we show that PM retarded the development of nephropathy in diabetic rats, as measured by decreases in both urinary albumin and plasma creatinine concentrations. Proteinuria, measured at the end of the study, was also significantly decreased in PM-treated rats. Similar effects were observed for both PM and AG, although PM was significantly more effective in inhibiting the increases in microalbuminuria and creatininemia, and correcting the dyslipidemia and redox imbalances in the rats (Oturai et al. 1996. *APMIS* 104:259–264; Soulis-Liparota et al. 1991. *Diabetes* 40:1328–1334).

In one of the latter studies, however, AG did partially inhibit mesangial expansion (Soulis-Liparota et al. 1991. *Diabetes* 40:1328–1334). In a related report, AG inhibited the increase in glomerular basement membrane thickening and fractional mesangial volume in Otsuka Long-Evans Tokushima fatty rats, a model for type 2 diabetes (Yamauchi et al. 1997. *Diab. Res. Clin. Pract.* 34:127–133). The potent effects of AGE inhibitors on diabetic nephropathy, but variable effects on renal morphology, suggest that renal morphological changes may be driven by hyperfiltration or hypertension (not measured) or other aspects of renal hemodynamics that were not measured in these experiments.

Future studies on cellular changes in the diabetic kidney, e.g. changes in podocyte and mesangial cell number, may provide better insight into the relationship between the structural and functional changes in the diabetic kidney.

Metabolic effects of AGE inhibitors. Although lipid lowering effects of AG in diabetic humans have been reported previously (Bucala et al. 1994. *Proc. Natl. Acad. Sci.* 91:9441–9445), the magnitude of the effects of PM and AG on plasma cholesterol and triglycerides in the STZ-diabetic rats was surprising. These changes, together with effects on plasma free fatty acids and glycerol, indicate that, in addition to their AGE-inhibitory activity, AG and PM affect central pathways of lipid metabolism. Since there is little structural resemblance between AG and PM, it is unlikely that the effects of PM are derived from its conversion to pyridoxal phosphate or other $B_6$ vitamers.

Hyperglycemia is known to induce shifts in intracellular ratios of redox coenzymes, both in vitro and in vivo, leading to a state of pseudohypoxia (Williamson et al. 1993. *Diabetes* 42:801–813). The magnitude of the increase in plasma lactate and the lactate:pyruvate ratio in the diabetic rats suggests a redox shift or true hypoxia in major tissues in the body, e.g. muscle or nerve. These changes may result from decreased perfusion and oxygenation of peripheral tissue and play an important role in development of diabetic microangiopathy and neuropathy in both humans and animal models (Mayrovitz and Larsen, 1996. *Microvasc. Res.* 52:115–126; Tesfaye et al. 1994. *Diabetologia* 37:847–854; Cameron, and Cotter, 1994. *Diab. Metab. Rev.* 10:189–224; Boulton and Malik, 1999. Organ specific vascular changes. In *Diabetic Angiopathy*. Tooke, J. E., editor. New York: Oxford University Press. pp. 267–275).

A recent report (Pyke et al. 1999. *Diabetes* 48 (Suppl. 1) 593(Abstr.)) that the diabetic kidney is also hypoxic suggests that hypoxia may be a common mechanism contributing to altered metabolism and development of pathology in diabetes. The resultant increase in anaerobic metabolism of carbohydrates suggests that aerobic metabolism of lipids may also be impaired, contributing in part to the hyperlipidemia in the diabetic rat. It is possible that all of these effects are secondary to inhibition of AGE formation in the vasculature, but we cannot exclude multiple mechanisms of action of the drugs. Evaluation of the kinetics of PM's effects on tissue oxygen tension, peripheral vascular resistance, lipid concentrations and the lactate:pyruvate ratio in plasma of the diabetic rat will yield important insights into the mechanism of drug action and the role of hypoxia in the development of metabolic and functional changes in the STZ-diabetic rat.

Mechanism of action of PM. The effects of PM and AG are consistent with the AGE hypothesis on diabetic complications. Both drugs inhibit the formation of CML, and CEL, theoretically by trapping reactive carbonyl intermediates involved in AGE formation, and they also retard the development of diabetic nephropathy. However, the failure of either PM or AG to affect pentosidine formation, combined with the strong correlations between triglycerides and CML, and between triglycerides and albuminuria or creatininemia, suggests that lipids may be important in both the formation of AGEs and development of nephropathy. Indeed, both CML and CEL are formed during lipid peroxidation reactions (unpublished results, and Fu, et al. 1996. *J. Biol. Chem.* 271: 9982–9986), and it could be argued that the decrease in their concentration in collagen could be a direct result of the decrease in plasma triglycerides effected by the AGE inhibitors. However, the fact that pentosidine, a product derived exclusively from carbohydrates (Pyke et al. 1999. *Diabetes* 48 (Suppl. 1) 593(Abstr.)) is increased in both skin and renal collagen of diabetic rats indicates that carbohydrate autoxidation and glycoxidation contribute to AGE formation. Although neither PM nor AG prevented the increase in pentosidine in skin collagen, this may reflect the fact that it is more difficult to inhibit formation of pentosidine, compared to CML, in vitro (Dyer et al. 1991. *J. Biol. Chem.* 266:11654–11660; Litchfield et al. 1999. *Int. J. Biochem.* In press). The relative increases in CML, CEL and pentosidine are also similar in diabetic compared to control rats, consistent with their origin from a common precursor, which, in the case of pentosidine, must be carbohydrate in nature. The relative levels of CML and pentosidine in skin (Degenhardt et al., in press) and renal collagen are also consistent with the relative yields of these compounds during modification of collagen by glucose in vitro (Dyer et al. 1991. *J. Biol. Chem.* 266:11654–11660; Litchfield et al. 1999. *Int. J. Biochem.* In press), i.e. 50–100 fold higher concentration of CML, compared to pentosidine. Thus, it seems most likely that all three of these products, as well as the increased fluorescence and crosslinking of diabetic collagen, are derived from glycoxidation reactions.

Dyslipidemia and diabetic complications. Dyslipidemia is recognized as a risk factor for development of diabetic nephropathy (Oda and Keane, 1997. *Kidney Internat.* 52, Suppl. 2:S36–S38; Smulders, et al. 1997. *Eur. J. Clin. Invest.* 27:997–1002), but is also commonly associated with nephropathy, independent of diabetes (Guijarro and Keane, 1993. *Curr. Opin. Nephrol. Hypertens.* 2:372–379;Saito, T. 1997. *Tohoku J. Exp. Med.* 181:321–337). It seems most likely that the abnormalities in lipid metabolism would have developed early in diabetes, in concert with the development of hyperglycemia. In this case, dyslipidemia may have accelerated the development of nephropathy, possibly through localized oxidation of lipoproteins entrapped in the kidney (or vasculature) and subsequent formation of advanced lipoxidation end-products (ALEs). Both AG (Picard et al. 1992. *Proc. Natl. Acad. Sci. USA* 89:6876–6880; Giardino et al. 1998. *Diabetes* 47:1114–1120) and PM (unpublished results) are known to inhibit modification of proteins during lipid peroxidation reactions, suggesting a mechanism, in addition to inhibition of glycoxidation reactions, by which these drugs may provide protection against diabetic nephropathy. A concerted effect on formation of both AGEs and ALEs may lead to decreased modification (thickening, stiffening) of vascular collagen, improved peripheral perfusion and oxygenation, normalization of lipid metabolism and correction of dyslipidemia. The cause-effect relationships between these pathologies cannot be determined by the present experiments and available data, however measurement of ALEs in tissues of control, diabetic and PM-treated diabetic animals may uncover a broader range of effects of AGE-inhibitors on the chemical modification of proteins and the development of complications in diabetes.

There are multiple causes of dyslipidemia, including genetics, dietary factors, and disease, as well as a complex interplay between these various causes of dyslipidemia. Methods to prevent and/or treat dyslipidemia may then be dependent of its causative factors.

Pyridoxamine has previously been reported to partially decrease elevated serum lipid levels caused by excessive lipid intake (i.e., high cholesterol diet) in a rat model. (Speck, U.S. Pat. No. 5,288,716). Speck does not discuss other causes of hyperlipidemia such as renal failure or genetic deficiencies in lipid metabolism. Prior to the data presented in the instant application, no data existed for the use of pyridoxamine to treat or prevent hyperlipidemia caused by defective lipid metabolism. Particularly, Speck et al. did not provide any guidance with respect to the effect of pyridoxamine in treating or preventing hyperlipidemia associated with diabetes, a condition known to dramatically effect numerous metabolic pathways and to have wide-ranging physiological effects.

In summary, we have demonstrated that the AGE inhibitors PM and AG inhibit the chemical modification of tissue proteins, retard the development of nephropathy, and substantially reverse dyslipidemia in the STZ-diabetic rat. We have also demonstrated that PM and AG substantially reverse redox imbalances in the STZ-diabetic rat. Systemic redox imbalances are indicative of pseudohypoxia, hypoxia, and ischemia in tissues, conditions which play an important role in many disease states, including but not limited to diabetic complications, neurodegenerative diseases such as Alzheimer's and amyotrophic lateral sclerosis; shock, inflammatory injuries and diseases, aging, and tissue ischemia. (See for example, Andrus et al., J. Neurochem. 71:2–41–2048 (1998); Hall et al., J. Neurosci. Res. 53:66–77 (1998); Smith et al., J. Histochem. Cytochem. 46:731–735 (1998); Smith et al., J. Neurochem. 70:2212–2215 (1998); Russell et al., Arch. Biochem. Biophys. 370:236–239 (1999); Flowers and Zimmerman, New Horizons 6:169–180 (1998); Piedimonte et al., J. Infect. Disease 176:655–664 (1997) Thus, methods for treating and preventing redox imbalances are useful in treating these conditions.

In general, PM appeared to be comparable to AG in inhibition of nonenzymatic modifications of collagen, but significantly more effective in inhibiting the biochemical and physiological changes in the diabetic rats. Our results suggest a complex web of interactions between the altered chemistry and biochemistry of both carbohydrates and lipids in diabetes. Animal toxicology studies have shown that PM has low toxicity and a good safety profile, and Phase I clinical trials are now in progress in an effort to evaluate the efficacy of PM for treatment of diabetic complications.

The plasma levels of cholesterol and triglycerides were also lowered by PM in the diabetic rat studies. The mechanism by which PM would lower cholesterol and triglycerides is not known, but suggests that PM may affect certain enzymatic pathways of cholesterol synthesis and degradation. For example, PM may inhibit hydroxymethylglutaryl-coenzyme A (HMG-CoA) reductase or angiotension converting enzyme (ACE). The lowering of plasma creatinine and urinary albumin, of AGE formation in skin, and of total cholesterol and triglycerides in a diabetic animal model supports the hypothesis that PM is a versatile drug capable of inhibiting several altered metabolic processes and protein damage associated with the development of complications arising from both diabetes and dyslipidemia.

We have also provided evidence suggesting that administration of PM may prove useful for the treatment of vascular disease, as well for the prevention of complications of diabetes associated with vascular dysfunction, including neuropathy, retinopathy, and wound healing deficits in diabetes, as well as treatment of vascular disease, tissue hypoxia, and ischemia in patients without diabetes.

EXAMPLE 7

Compounds for Inhibiting Oxidative Protein Modification

The present invention encompasses compounds, and pharmaceutical compositions containing compounds having the general formula:

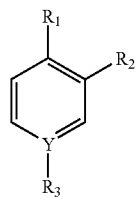

Formula I wherein $R_1$ is $CH_2NH_2$, $CH_2SH$, $COOH$, $CH_2CH_2NH_2$, $CH_2CH_2SH$, or $CH_2COOH$;
$R_2$ is OH, SH or $NH_2$;
Y is N or C, such that when Y is N $R_3$ is nothing, and when Y is C, $R_3$ is $NO_2$ or another electron withdrawing group;

and salts thereof.

The present invention also encompasses compounds of the general formula

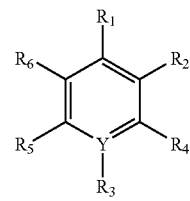

Formula II

Formula II
wherein $R_1$ is $CH_2NH_2$, $CH_2SH$, $COOH$, $CH_2CH_2NH_2$, $CH_2CH_2SH$, or $CH_2COOH$;
$R_2$ is OH, SH or $NH_2$;
Y is N or C, such that when Y is N $R_3$ is nothing, and when Y is C, $R_3$ is $NO_2$ or another electron withdrawing group;
$R_4$ is H, or C 1–18 alkyl;
$R_5$ and $R_6$ are H, C 1–18 alkyl, alkoxy or alkane;

and salts thereof.

In addition, the instant invention also envisions compounds of the formulas

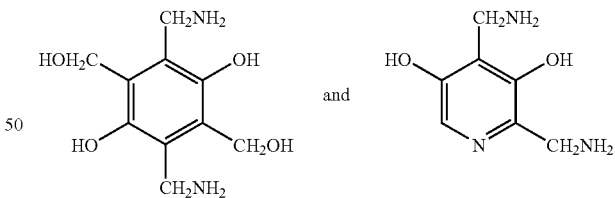

The compounds of the present-invention can embody one or more electron withdrawing groups, such as and not limited to —$NH_2$, —NHR, —$NR_2$, —OH, —$OCH_3$, —OCR, and —NH—$COCH_3$ where R is C 1–18 alkyl.

By "alkyl" and "lower alkyl" in the present invention is meant straight or branched chain is alkyl groups having from 1–18 carbon atoms, such as, for example, methyl, ethyl, propyl isopropyl, n-butyl, sec-butyl,tert-butyl, pentyl, 2-pentyl, isopentyl, neopentyl, hexyl, 2-hexyl, 3-hexyl, and 3-methylpentyl. Unless indicated otherwise, the alkyl group substituents herein are optionally substituted with at least one group independently selected from hydroxy, mono- or dialkyl amino, phenyl or pyridyl.

By "alkoxy" and "lower alkoxy" in the present invention is meant straight or branched chain alkoxy groups having 1–18 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By "alkene" and "lower alkene" in the present invention is meant straight and branched chain alkene groups having 1–18 carbon atoms, such as, for example, ethlene, propylene, 1-butene, 1-pentene, 1-hexene, cis and trans 2-butene or 2-pentene, isobutylene, 3-methyl-1-butene, 2-methyl-2-butene, and 2,3-dimethyl-2-butene.

By "salts thereof" in the present invention is meant compounds of the present invention as salts and metal complexes with said compounds, such as with, and not limited to, Al, Zn, Mg, Cu, and Fe.

One of ordinary skill in the art will be able to make compounds of the present invention using standard methods and techniques.

The instant invention encompasses pharmaceutical compositions which comprise one or more of the compounds of the present invention, or salts thereof, in a suitable carrier. The instant invention encompasses methods for administering pharmaceuticals of the present invention for therapeutic intervention of pathologies which are related to AGE formation in vivo. In one preferred embodiment of the present invention the AGE related pathology to be treated is related to diabetic nephropathy.

The instant invention may be embodied in other forms or carried out in other ways without departing from the spirit or essential characteristics thereof. The present disclosure and enumerated examples are therefore to be considered as in all respects illustrative and not restrictive, the scope of the invention being indicated by the appended claims, and all equivalency are intended to be embraced therein. One of ordinary skill in the art would be able to recognize equivalent embodiments of the instant invention, and be able to practice such embodiments using the teaching of the instant disclosure and only routine experimentation.

We claim:

1. A method for treating diabetic neuropathy in a mammal consisting of administering to a diabetic mammal an amount effective to treat diabetic neuropathy of pyridoxamine or a salt thereof.

2. The method of claim 1 wherein the mammal is a human.

* * * * *